United States Patent [19]

Nishikawa et al.

[11] Patent Number: 5,666,434

[45] Date of Patent: Sep. 9, 1997

[54] COMPUTER-AIDED METHOD FOR IMAGE FEATURE ANALYSIS AND DIAGNOSIS IN MAMMOGRAPHY

[75] Inventors: Robert M. Nishikawa, Chicago; Takehiro Ema, Westmont; Hiroyuki Yoshida, Westmont; Kunio Doi, Willowbrook, all of Ill.

[73] Assignee: Arch Development Corporation, Chicago, Ill.

[21] Appl. No.: 536,794

[22] Filed: Sep. 29, 1995

Related U.S. Application Data

[62] Division of Ser. No. 235,530, Apr. 29, 1994, abandoned.
[51] Int. Cl.$^6$ ........................................ G06K 9/00
[52] U.S. Cl. ................ 382/128; 382/130; 382/132; 382/199; 382/257; 382/260
[58] Field of Search ........................ 382/128, 130, 382/131, 132, 199, 257, 260, 275, 308; 364/413.23

[56] References Cited

PUBLICATIONS

Yoshimura et al, "Computerized Scheme for the Detection of Pulmonary Nodules A Nonlinear Filtering Technique", Reprinted from Investigative Radiology, Feb. 1992, vol. 27, No. 2, pp. 124–129.

Barba et al, "Edge detection in cytology using morphological filters", SPIE vol. 1075, 1989, pp. 311–318.

Bartoo et al, "Mathematical Morphology techniques for image processing applications in biomedical imaging", 1988, 10 pages.

*Primary Examiner*—Leo Boudreau
*Assistant Examiner*—Phuoc Tran
*Attorney, Agent, or Firm*—Oblon, Spivak, McClelland, Maier & Neustadt, P.C.

[57] ABSTRACT

A method for automated detection of abnormal anatomic regions, wherein a mammogram is digitized to produce a digital image and the digital image is processed using local edge gradient analysis and linear pattern analysis in addition to feature extraction routines to identify abnormal anatomic regions. Noise reduction filtering and pit-filling/spike-removal filtering techniques are also provided. Multiple difference imaging techniques are also used in which difference images employing different filter characteristics are obtained and processing results logically OR'ed to identify abnormal anatomic regions. In another embodiment the processing results with and without noise reduction filtering are logically AND'ed to improve detection sensitivity. Also, in another embodiment the wavelet transform is utilized in the identification and detection of abnormal regions. The wavelet transform is preferably used in conjunction with the difference imaging technique with the results of the two techniques being logically OR'ed.

15 Claims, 37 Drawing Sheets

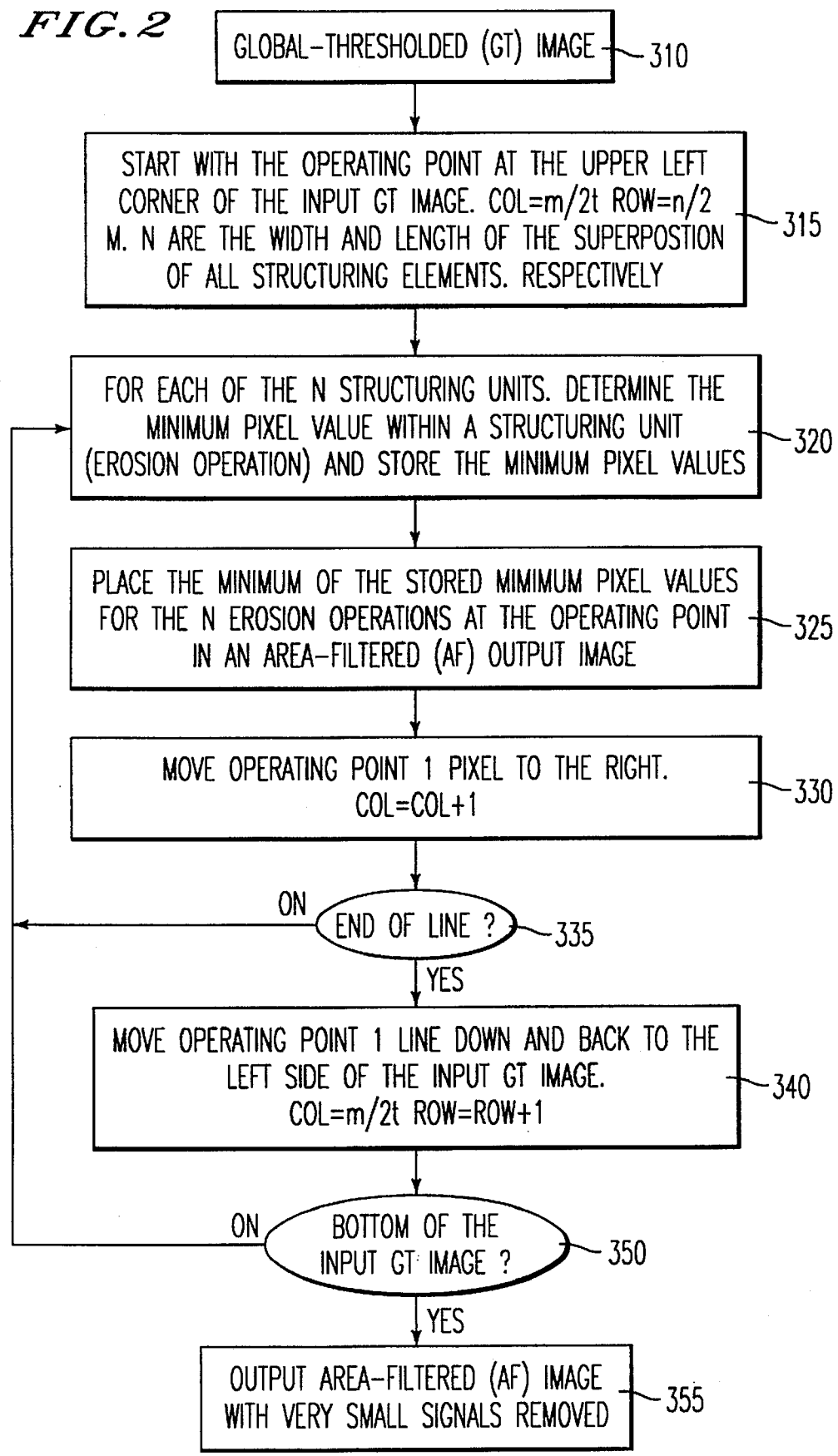

SIGNAL-PERIMETER PIXEL
SIGNAL-CORE PIXEL
PIXEL OUTSIDE THE SIGNAL

| 496 | 511 | 528 | 512 | 511 | 513 | 511 | 511 |
|-----|-----|-----|-----|-----|-----|-----|-----|
| 498 | 512 | 513 | 511 | 518 | 528 | 522 | 513 |
| 511 | 511 | 523 | 528 | 559 | 543 | 519 | 512 |
| 544 | 519 | 552 | 564 | 537 | 543 | 512 | 511 |
| 512 | 515 | 539 | 543 | 544 | 517 | 501 | 512 |
| 511 | 512 | 524 | 527 | 528 | 528 | 504 | 490 |
| 522 | 503 | 512 | 515 | 527 | 512 | 500 | 503 |

ORIGINAL IMAGE

| 503 | 512 | 513 | 511 | 512 | 513 | 512 | 512 |
|-----|-----|-----|-----|-----|-----|-----|-----|
| 503 | 511 | 513 | 513 | 518 | 522 | 519 | 513 |
| 511 | 512 | 523 | 528 | 537 | 543 | 519 | 512 |
| 514 | 519 | 539 | 537 | 544 | 537 | 512 | 512 |
| 512 | 515 | 524 | 512 | 527 | 528 | 512 | 511 |
| 512 | 512 | 512 | 525 | 522 | 517 | 504 | 503 |
| 511 | 512 |     |     |     |     | 504 | 500 |

AFTER MEDIAN FILTERING

| 496 | 511 | 528 | 512 | 511 | 513 | 512 | 512 |
|-----|-----|-----|-----|-----|-----|-----|-----|
| 498 | 512 | 513 | 511 | 518 | 528 | 522 | 513 |
| 511 | 511 | 523 | 528 | 552 | 543 | 519 | 512 |
| 519 | 519 | 552 | 522 | 537 | 543 | 512 | 511 |
| 512 | 515 | 539 | 543 | 544 | 517 | 501 | 512 |
| 511 | 512 | 524 | 527 | 528 | 528 | 504 | 500 |
| 512 | 511 | 512 | 515 | 527 | 512 | 500 | 503 |

AFTER NOISE REDUCTION FILTER
USING 60 STRUCTURING ELEMENTS

| 503 | 511 | 512 | 512 | 512 | 513 | 512 | 512 |
|-----|-----|-----|-----|-----|-----|-----|-----|
| 503 | 512 | 513 | 512 | 518 | 528 | 522 | 513 |
| 511 | 513 | 523 | 528 | 543 | 543 | 519 | 512 |
| 519 | 519 | 543 | 543 | 543 | 543 | 512 | 512 |
| 512 | 515 | 539 | 543 | 543 | 517 | 504 | 504 |
| 511 | 512 | 524 | 527 | 528 | 528 | 504 | 503 |
| 511 | 511 | 512 | 512 | 515 | 527 | 503 | 503 |

AFTER NOISE REDUCTION FILTER
USING 18 STRUCTURING ELEMENTS

*FIG. 23A*

| 519 | 575 | 558 | 545 | 520 | 526 | 543 | 542 | 567 | 536 |
|---|---|---|---|---|---|---|---|---|---|
| 565 | 558 | 540 | 567 | 551 | 525 | 539 | 528 | 552 | 543 |
| 559 | 560 | 579 | 619 | 583 | 575 | 584 | 566 | 560 | 544 |
| 538 | 548 | 554 | 617 | 582 | 592 | 581 | 560 | 567 | 559 |
| 549 | 542 | 543 | 549 | 546 | 581 | 543 | 567 | 559 | 531 |
| 520 | 530 | 547 | 534 | 551 | 558 | 544 | 546 | 531 | 568 |
| 539 | 512 | 534 | 551 | 558 | 544 | 546 | 531 | 541 |  |

ORIGINAL IMAGE

| 544 | 558 | 558 | 558 | 545 | 525 | 542 | 543 | 543 |
|---|---|---|---|---|---|---|---|---|
| 558 | 560 | 558 | 560 | 551 | 539 | 539 | 539 | 543 |
| 559 | 559 | 560 | 583 | 582 | 583 | 566 | 552 | 544 |
| 548 | 543 | 554 | 617 | 583 | 575 | 566 | 559 | 551 |
| 540 | 543 | 547 | 549 | 560 | 567 | 559 | 559 | 559 |
| 530 | 530 | 543 | 547 | 558 | 559 | 546 | 559 | 568 |
| 520 | 530 | 547 | 546 | 547 | 546 | 544 | 531 | 541 |

AFTER MEDIAN FILTERING

| 533 | 560 | 558 | 545 | 525 | 526 | 543 | 542 | 567 | 539 |
|---|---|---|---|---|---|---|---|---|---|
| 560 | 558 | 545 | 567 | 551 | 525 | 539 | 539 | 552 | 543 |
| 559 | 560 | 579 | 583 | 583 | 575 | 583 | 566 | 560 | 544 |
| 540 | 548 | 554 | 583 | 582 | 583 | 560 | 544 | 559 | 571 |
| 548 | 542 | 543 | 549 | 546 | 581 | 544 | 567 | 559 | 568 |
| 520 | 530 | 547 | 534 | 551 | 558 | 544 | 546 | 531 | 541 |
| 536 | 520 | 534 | 551 | 558 | 544 | 546 | 531 | 541 |  |

AFTER NOISE REDUCTION FILTER
USING 60 STRUCTURING ELEMENTS

| 543 | 558 | 558 | 545 | 526 | 526 | 543 | 542 | 567 | 539 |
|---|---|---|---|---|---|---|---|---|---|
| 559 | 558 | 560 | 567 | 551 | 526 | 539 | 539 | 552 | 543 |
| 559 | 560 | 579 | 583 | 583 | 575 | 575 | 566 | 560 | 544 |
| 543 | 560 | 554 | 583 | 582 | 582 | 560 | 544 | 559 | 568 |
| 542 | 530 | 543 | 549 | 547 | 581 | 547 | 547 | 559 | 541 |
| 527 | 530 | 546 | 547 | 547 | 547 | 544 | 531 | 531 |  |
| 527 | 530 | 534 | 551 | 546 | 534 | 531 | 541 |  |  |

AFTER NOISE REDUCTION FILTER
USING 18 STRUCTURING ELEMENTS

FIG. 23B

FIG. 27A
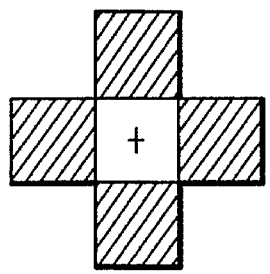
FIG. 27B
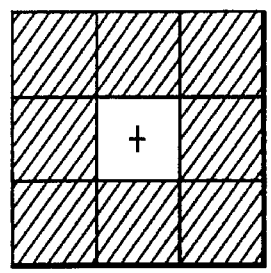

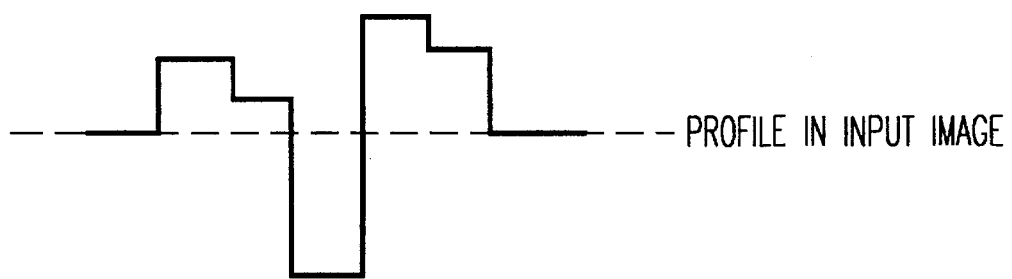
PIT-FILLING OPERATION
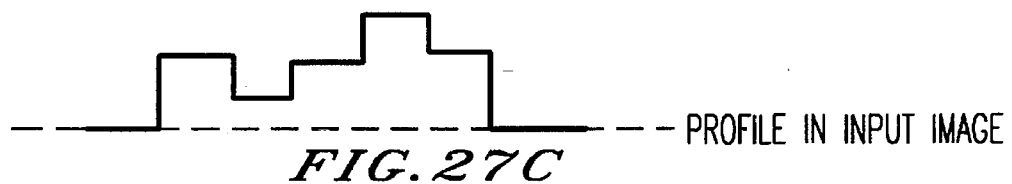
FIG.27C
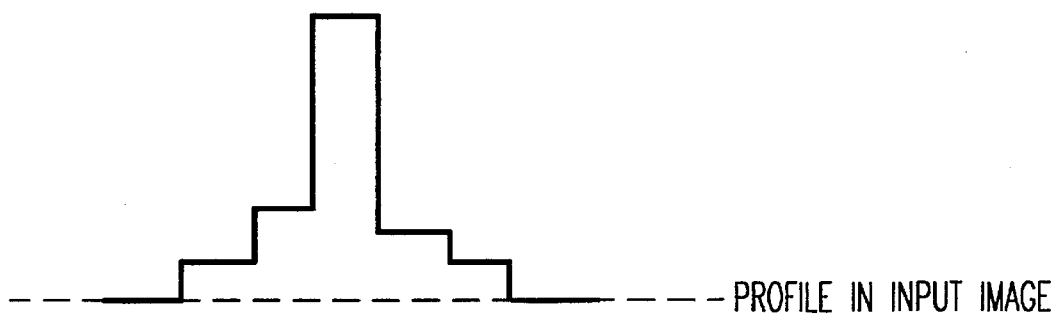
SPIKE-REMOVAL OPERATION
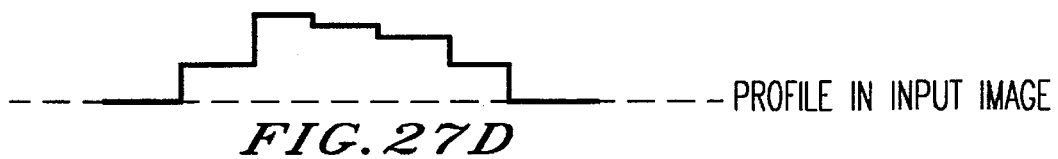
FIG.27D

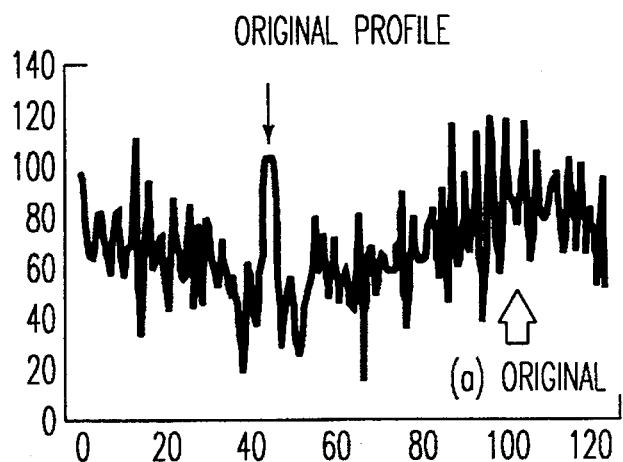
FIG. 29A (a) ORIGINAL
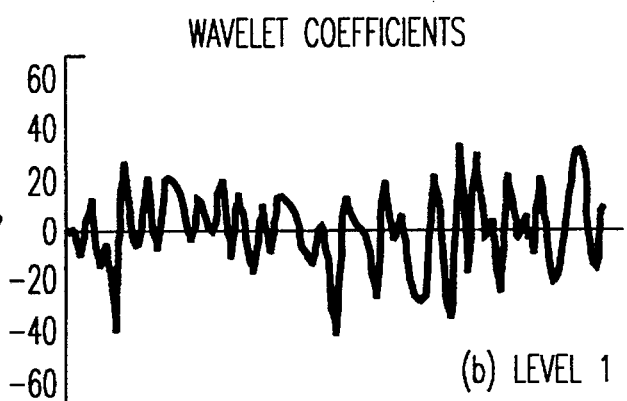
FIG. 29B (b) LEVEL 1
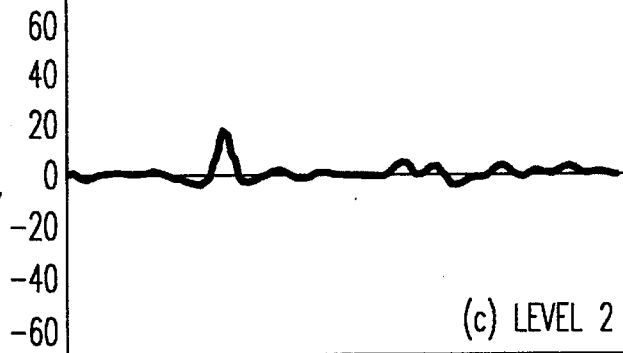
FIG. 29C (c) LEVEL 2
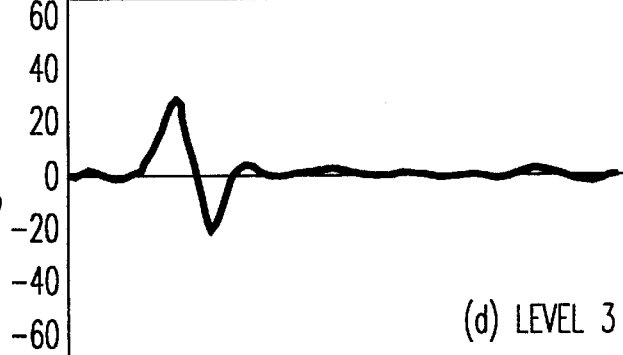
FIG. 29D (d) LEVEL 3

WAVELET COEFFICIENTS
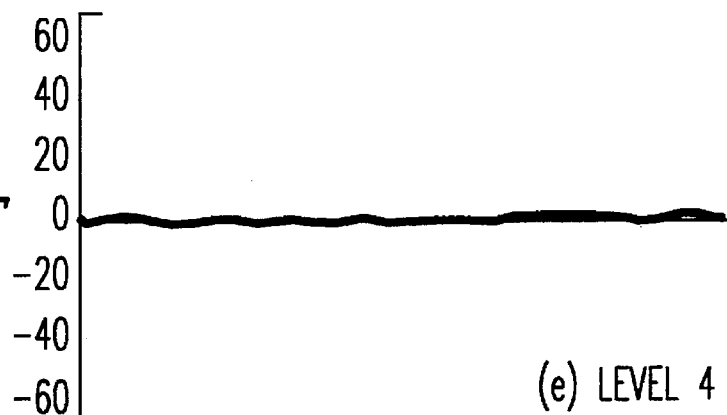
FIG. 29E (e) LEVEL 4
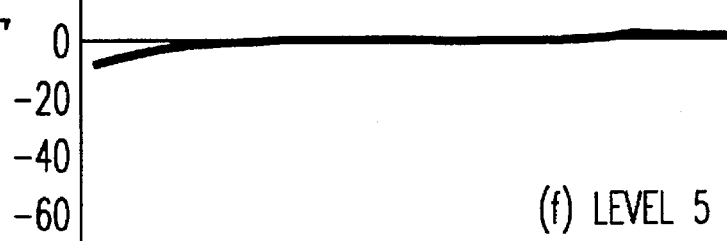
FIG. 29F (f) LEVEL 5
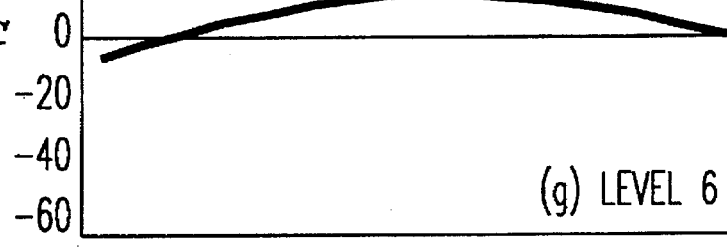
FIG. 29G (g) LEVEL 6

RECONSTRUCTED PROFILE (h) LEVEL 1

(i) LEVEL 2

(j) LEVEL 3

RECONSTRUCTED PROFILE
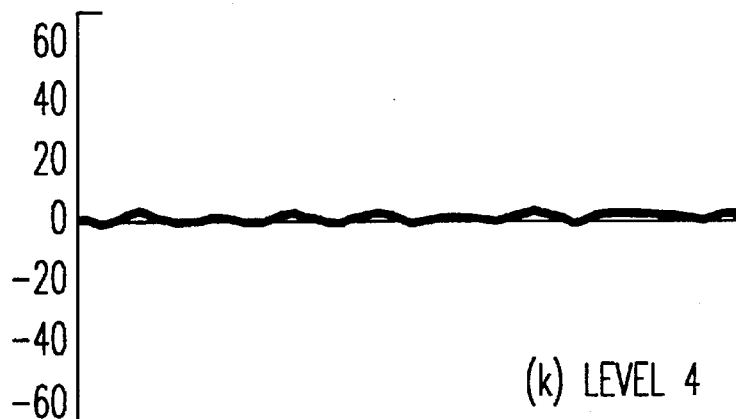
FIG. 29K (k) LEVEL 4
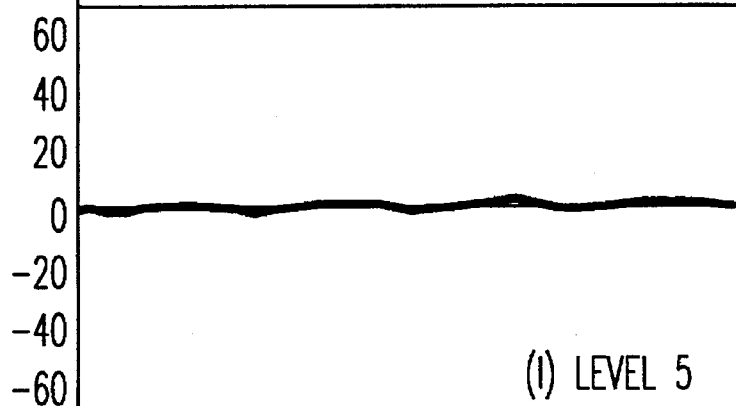
FIG. 29L (l) LEVEL 5
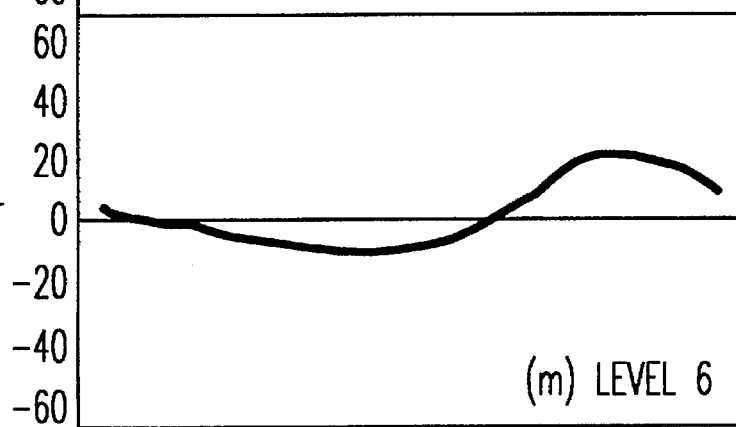
FIG. 29M (m) LEVEL 6

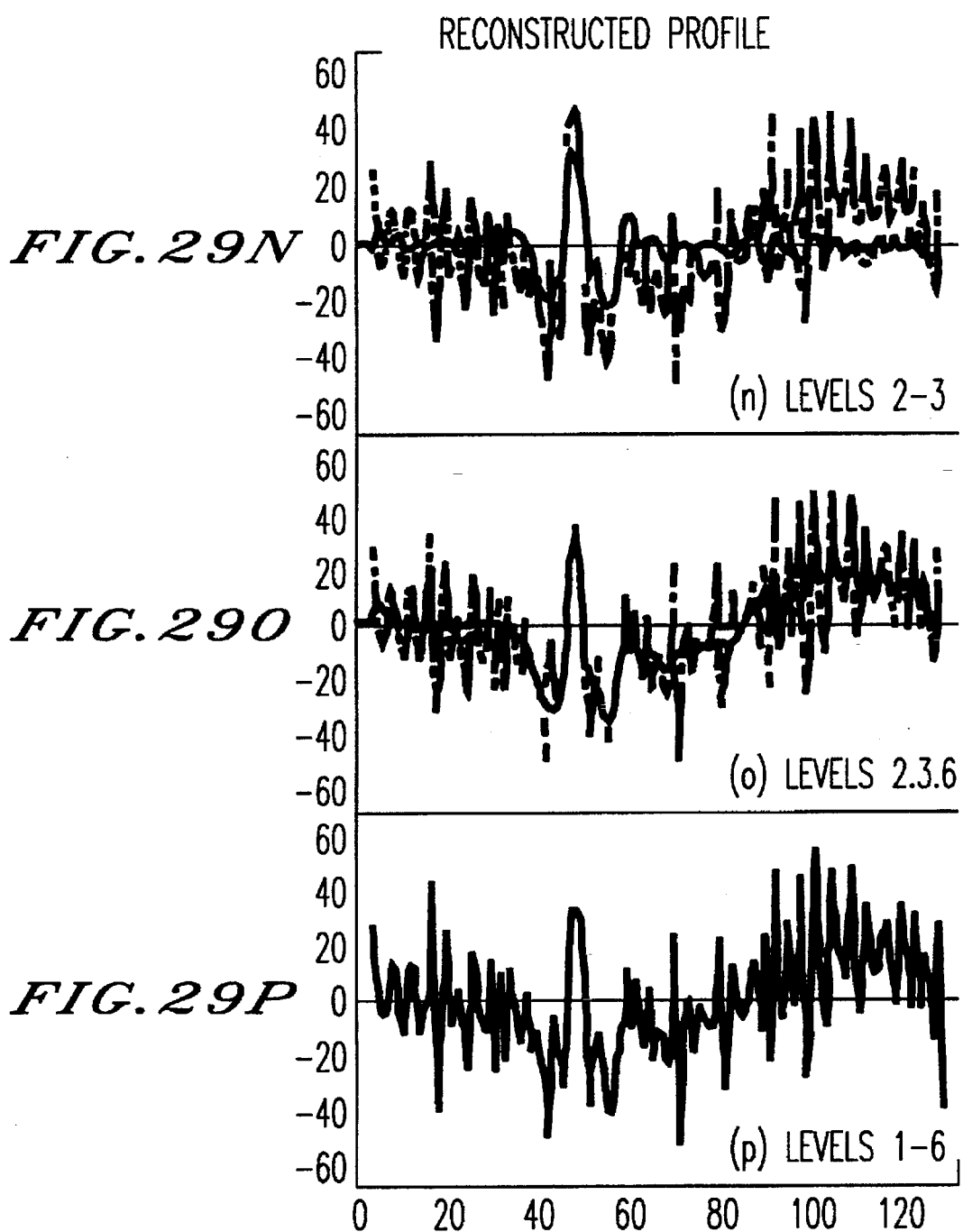

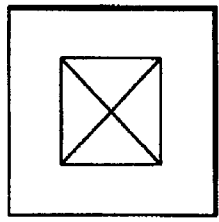
FIG. 35A
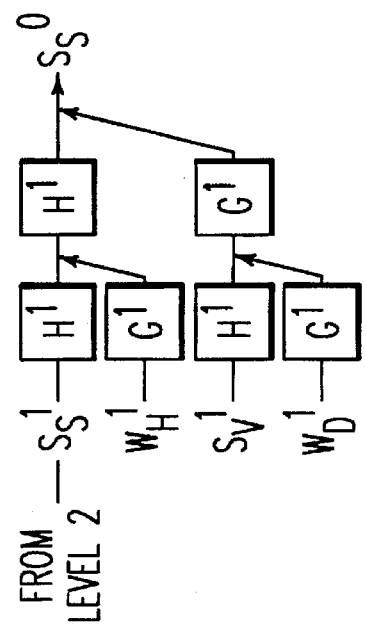
FIG. 35B
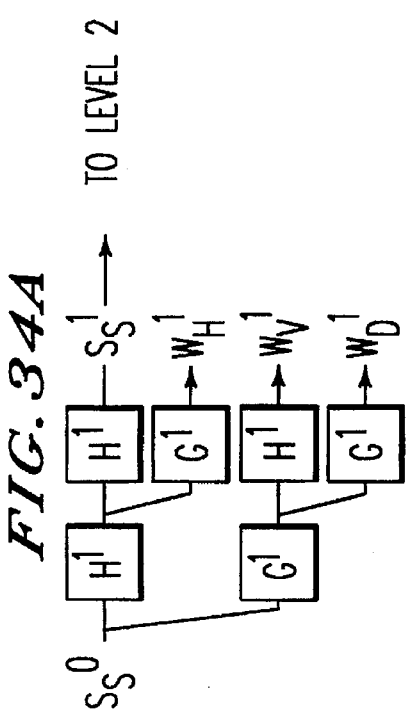
FIG. 34A
FIG. 34B

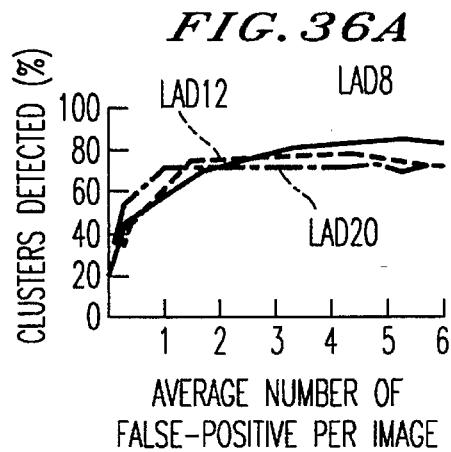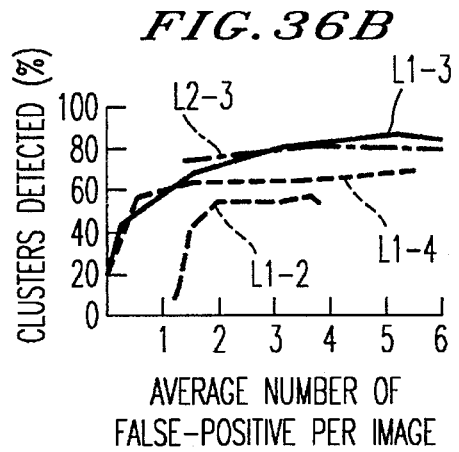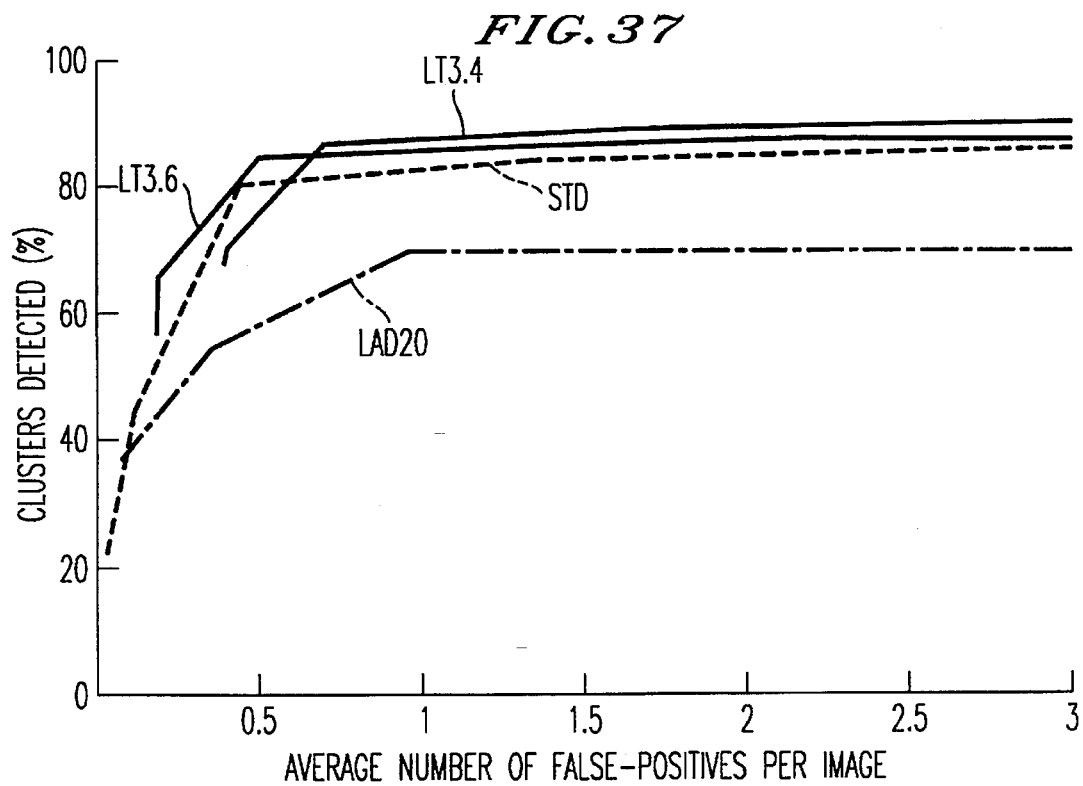

COMPUTER-AIDED METHOD FOR IMAGE FEATURE ANALYSIS AND DIAGNOSIS IN MAMMOGRAPHY

This is a division, of application Ser. No. 08/235/530 filed on Apr. 29, 1994, abandoned.

This invention was made in part with U.S. Government support under grant numbers USPHS CA24806, 47043, 48985 and 60187 from N.C.I., N.I.H. and D.H.H.S. and under grant number DAMD 17-93-J-3021 from the U.S. Army. The U.S. Government has certain rights in the invention.

BACKGROUND OF THE INVENTION

1. Field of the Invention

This invention relates generally to a method for automated processing of medical images, and more particularly to an automated method for the detection and classification of abnormal regions, particularly microcalcifications in digital mammographic images. The present invention further relates to the subject matter described in commonly owned U.S. Pat. Nos. 5,289,374, 5,133,020 and 4,907,156 and pending U.S. patent applications Ser. Nos. 07/843,721, now U.S. Pat. No. 5,343,390, and 07/915,631, now U.S. Pat. No. 5,537,485.

2. Discussion of the Background

Detection and diagnosis of abnormal anatomical regions in radiographs, such as cancerous lung nodules in chest radiographs and microcalcifications in women's breast radiographs, so called mammograms, are among the most important and difficult task's performed by radiologists.

Recent studies have concluded that the prognosis for patients with lung cancer is improved by early radiographic detection. In one study on lung cancer detection, it was found that, in retrospect, 90% of subsequently diagnosed peripheral lung carcinomas were visible on earlier radiographs. The observer error which caused these lesions to be missed may be due to the camouflaging effect of the surrounding anatomical background on the nodule of interest, or to the subjective and varying decision criteria used by radiologists. Underreading of a radiograph may be due to a lack of clinical data, lack of experience, a premature discontinuation of the film reading because of a definite finding, focusing of attention on another abnormality by virtue of a specific clinical question, failure to review previous films, distractions, and "illusory visual experiences".

Similarly, early diagnosis and treatment of breast cancer, a leading cause of death in women, significantly improves the chances of survival.

X-ray mammography is the only diagnostic procedure with a proven capability for detecting early-stage, clinically occult breast cancers. Between 30 and 50% of breast carcinomas detected radiographically demonstrate microcalcifications on mammograms, and between 60 and 80% of breast carcinomas reveal microcalcifications upon microscopic examination. Therefore any increase in the detection of microcalcifications by mammography will lead to further improvements in its efficacy in the detection of early breast cancer. The American Cancer Society has recommended the use of mammography for screening of asymptomatic women over the age of 40 with annual examinations after the age 50. For this reason, mammography may eventually constitute one of the highest volume X-ray procedures routinely interpreted by radiologists.

A computer scheme that alerts the radiologist to the location of highly suspect lung nodules or breast microcalcifications should allow the number of false-negative diagnoses to be reduced. This could lead to earlier detection of primary lung and breast cancers and a better prognosis for the patient. As more digital radiographic imaging systems are developed, computer-aided searches become feasible. Successful detection schemes could eventually be hardware implemented for on-line screening of all chest radiographs and mammograms, prior to viewing by a physician. Thus, chest radiographs ordered for medical reasons other than suspected lung cancer would also undergo careful screening for nodules.

Several investigators have attempted to analyze mammographic abnormalities with digital computers. However, the known studies failed to achieve an accuracy acceptable for clinical practice. This failure can be attributed primarily to a large overlap in the features of benign and malignant lesions as they appear on mammograms.

The currently accepted standard of clinical care is such that biopsies are performed on 5 to 10 women for each cancer removed. Only with this high biopsy rate is there reasonable assurance that most mammographically detectable early carcinomas will be resected. Given the large amount of overlap between the characterization of abnormalities may eventually have a greater impact in clinical care. Microcalcifications represent an ideal target for automated detection, because subtle microcalcifications are often the first and sometimes the only radiographic findings in early, curable, breast cancers, yet individual microcalcifications in a suspicious cluster (i.e., one requiring biopsy) have a fairly limited range of radiographic appearances.

The high spatial-frequency content and the small size of microcalcifications require that digital mammographic systems provide high spatial resolution and high contrast sensitivity. Digital mammographic systems that may satisfy these requirements are still under development. Digital radiographic systems with moderately high spatial resolution are made possible by fluorescent image plate/laser readout technology. Currently, digital mammograms with high resolution can be obtained by digitizing screen-film images with a drum scanner or other scanning system. The increasing practicability of digital mammography further underlines the potential ability of a computer-aided system for analysis of mammograms.

The inventors and others at the Radiology Department at the University of Chicago have been developing a computerized scheme for the detection of clustered microcalcifications in mammograms with the goal of assisting radiologists' interpretation accuracy. (See H. P. Chan et al., "Image feature analysis and computer-aided diagnosis in digital radiography. 1. Automated detection of microcalcifications in mammography", Med. Phys. 14, 538–548 (1987); H. P. Chan et al., "Computer-aided detection of microcalcifications in mammograms: Methodology and preliminary clinical study", Invest. Radiol. 23, 664–671 (1988); H. P. Chan et al., "Improvement in radiologists' detection of clustered microcalcifications on mammograms: The potential of computer-aided diagnosis", Invest. Radiol. 25, 1102–1110 (1990); R. M. Nishikawa et al., "Computer-aided detection and diagnosis of masses and clustered microcalcifications from digital mammograms", Proc. SPIE 1905, 422–432 (1993); and R. M. Nishikawa et al., "Computer-aided detection of clustered microcalcifications: An improved method for grouping detected signals", Med. Phys. 20, 1661–1666 (1993).)

The computer outputs from this scheme, which involves quantitative analysis of digitized mammograms, indicate possible locations of clustered microcalcifications. These locations can be marked by arrows superimposed on mammograms displayed on the monitor of a workstation. (See U.S. Pat. No. 4,907,156.) If the computer output is presented to radiologists as a "second opinion" (see K. Dei et al., "Digital radiography: A useful clinical tool for computer-aided diagnosis by quantitative analysis of radiographic images", Acta Radiol. 34, 426–439 (1993); and M. L. Giger, "Computer-aided diagnosis", RSNA Categorical Course in Physics, 283–298 (1993)), it is expected that the accuracy in detecting clustered microcalcifications in mammograms would be improved by reducing false-negative detection rate. The prior computer-aided diagnosis (CAD) scheme has a sensitivity of approximately 85% with 2.5 false-positive clusters per mammogram. Since the sensitivity is at a relatively high level, a reduction of false-positive detection rate is desired before beginning clinical testing. The prior scheme uses the first moment of the power spectrum and the distribution of microcalcification signals to eliminate false-positive microcalcification signals. To reduce further the false-positive rate, new techniques, including application of an artificial neural network (see pending U.S. patent applications Ser. Nos. 08/053,345, now U.S. Pat. No. 5,463,548 and 08/060,531, now U.S. Pat. No. 5,491,627) and an area-thickness analysis (see Y. Jiang et al., "Method of extracting microcalcifications' signal area and signal thickness form digital mammograms", Proc SPIE 1778, 28–36 (1992)) have been investigated and have been shown to be effective.

However, further improvement in microcalcification detection sensitivity and diagnostic accuracy is desired.

SUMMARY OF THE INVENTION

Accordingly, an object of the invention is to provide an automated method and system for detecting and displaying abnormal anatomic regions existing in a digital X-ray image.

Another object of this invention is to provide an automated method and system for providing reliable early diagnosis of abnormal anatomic regions.

Yet another object of this invention is to minimize patient exposure to X-ray radiation by providing an automated method and system for detecting and displaying abnormal anatomic regions based on the digital information provided in a single X-ray image of the anatomy under diagnosis.

Yet another object of this invention is to determine causes of detected false-positive microcalcification signals and processing a digital image taking into account the causes of false-positive detections, thereby to decrease false-positive detections with little loss in sensitivity of true positive detections.

A further object of this invention is in general to decrease false-positive detections in a computer-implemented method for detecting abnormal anatomic regions.

Still a further object of this invention is to provide improved filtering techniques for filtering digital images to improve anatomic abnormality detection accuracy.

Another object of this invention is to provide a new and improved method of computer-aided detection of clustered microcalcifications on mammograms, whereby the accuracy of diagnosis can be improved by reducing the number of false-positive detections without decreasing the sensitivity for detecting true-positive microcalcifications.

These and other objects of this invention have been achieved according to the present invention by means of several advances in image-data processing and filtering as developed in a number of studies conducted by the inventors, as hereinafter disclosed. In one study, it was recognized that noise patterns, artifacts, linear patterns, ducts, step-like ridges and ring patterns appearing in digitized mammograms are sources of false-positive signals and the present invention provides specific processing techniques to eliminate false-positive microcalcification identifications related to such sources. To that end, according to the present invention, in an edge-gradient analysis, local edge-gradient values at signal-perimeter pixels of detected microcalcification signals are determined to eliminate false-positives that look like subtle microcalcifications or are due to artifacts. In a linear-pattern analysis, the degree of linearity for linear patterns are determined from local gradient values from a set of linear templates oriented in 16 different directions. Threshold values for the edge-gradient analysis and the linear-pattern analysis are utilized to eliminate false-positive detections to eliminate false-positive microcalcifications with elimination of only a very small loss in true-positive classifications. Combining the application of thresholds from the linear pattern analysis and the edge-gradient analysis reduces the false-positive detection rate while maintaining a high level of sensitivity.

The present invention includes additional techniques for improving sensitivity and reducing false positive microcalcification detections. According to one embodiment of the method of the present invention, multiple difference images are produced with each difference image preferably being formed by means of spatial filtering using a spatial filter having an optical transfer factor in the frequency range of 1.0 to 1.5 cycle/mm. The different difference images are processed to identify in the respective difference images locations which correspond to potential abnormal regions and the results are logically OR'ed to identify as candidate abnormal regions all those first and second locations which are separated by a predetermined distance or more. In one embodiment, the OR'ing operation occurs with respect to detected microcalcifications, and in another embodiment the OR'ing occurs with respect to detected microcalcification clusters.

In another embodiment of the present invention, novel filtering techniques are also employed. A digital image is subjected to noise reduction filtering using separate morphological erosion and dilation operators using plural structuring elements to produce an eroded image and a dilated image. A first absolute difference is determined between the original digital image and the eroded image and a second absolute difference is determined between the original digital image and the dilated image. Thereafter, the noise reduction filtering includes substituting for values of pixels in the original digital image with values of corresponding pixels in the eroded image when the first absolute difference is greater than the second absolute difference, or substituting for values of pixels in the original digital image with values of corresponding pixels in the dilated image when a second absolute difference is greater than the first absolute difference. Thereafter, linear filtering is performed, such as by using different image filtering and the signal extraction and feature analysis routines are performed on the linear filtered image to identify first locations of candidate abnormal regions. Preferably, the results of the processing after noise reduction filtering are AND'ed with the results obtained without noise reduction filtering to improve detection sensitivity In another filtering technique performed according to the present invention, the original digital image is subjected to a pit-filling and spike-removal filtering, performed by overlaying a filter kernel over each pixel of the digital image, determining the average pixel value of the overlaid pixels adjacent to the operator pixel, substituting the average pixel value for the pixel value of the operating point either if the pixel value at the operating point is smaller than all of the pixel values in the overlaid kernel or larger than all of the pixel values in the overlaid kernel, and outputting a filtered image including substituted pixel values resulting from the substituting step and the original pixel values from the digital image obtained in the obtaining step when substituting does not occur. Thereafter, linear filtering on the filtered image is performed followed by signal extraction and feature identification routines.

Also utilized according to the present invention is the wavelet transform. In this embodiment, the original digital image is filtered using a wavelet decomposition and reconstruction of the digital image to produce a transformation image. In reconstruction, the first and second levels in the wavelet domain are employed. Thereafter, feature extraction routines are performed and microcalcification clusters are identified. The wavelet transform technique is preferably combined with a difference imaging technique with the results being logically OR'ed to identify microcalcification clusters.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 is a more detailed schematic flow chart illustrating the signal extraction processing steps of the method shown in FIG. 1;

FIGS. 23(a) and 23(b) are illustrations of the effect of the noise reduction filter of the present invention on pixel values of an original image before and after noise reduction and before and after conventional median filtering;

FIGS. 27(a) and 27(b) are illustrations of filter kernels employed in another filter process performed according to the present invention; FIGS. 27(c) and 27(d) are illustrations of the effect of the pit-filling and spike removal operations performed according to the further filtering technique of the present invention;

FIG. 34 is an illustration of wavelet decomposition and reconstruction of images from level 0 to level 1 and from level 1 to level 0, respectively;

FIG. 35 is an illustration of a 2-dimensional wavelet transform from (a) an original pattern to (b) a wavelet decomposition pattern;

FIGS. 36(a) and 36(b) are FROC charts comparing the effects of wavelets with different lengths and the effects of images reconstructed from different levels in detecting clustered microcalcifications in mammograms;

FIG. 37 is a FROC chart comparing performance between the standard rule-based processing technique at different wavelet transform techniques;

DESCRIPTION OF THE PREFERRED EMBODIMENTS

Figure 1:
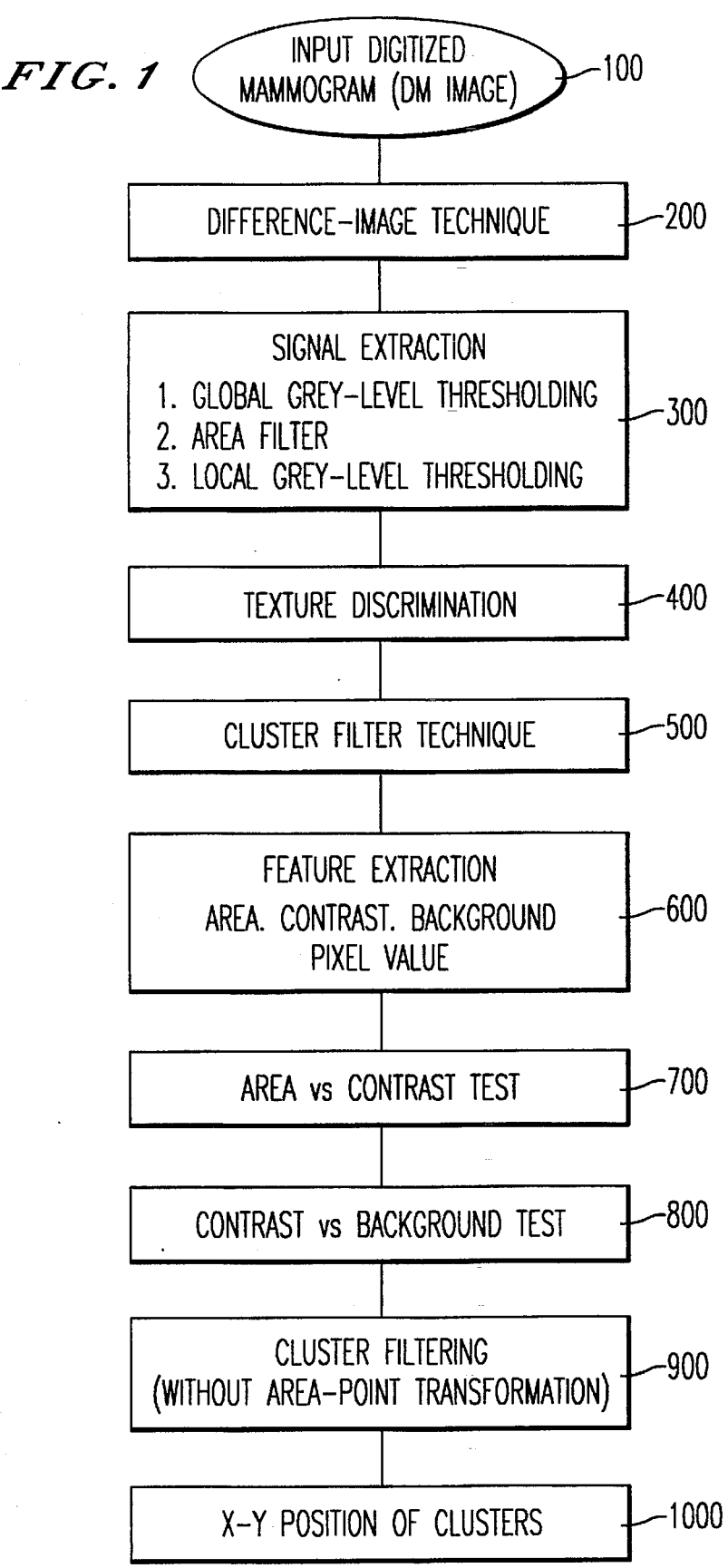
FIG. 1 is a schematic flow chart illustrating the processing steps of the method disclosed in related copending application Ser. No. 07/915,631, now U.S. Pat. No. 5,537,485, which steps are employed to identify microcalcification signal and clusters in the present invention.

Referring now to the drawings, wherein like reference numerals designate identical or corresponding parts throughout the several views, and more particularly to FIG. 1 thereof, there is shown a flow chart illustrating a sequence of initial processing steps performed as disclosed in copending commonly owned U.S. patent application Ser. No. 07/915,631, now U.S. Pat. No. 5,537,485, in order to detect the location of clusters which contain 3 or more microcalcification signals within a given region area.

In a first step 100, a digital mammogram is obtained using conventional hardware such as computed radiography systems and digitizing conventional mammograms using a laser scanner. In step 200, a difference image is produced from the digital mammogram, as described in U.S. Pat. No. 4,907,156. Thereafter, in step 300, signal extraction is performed.

In step 300, global-grey-level thresholding, utilizing histogram techniques as described in U.S. Pat. No. 4,907,156, is performed to eliminate all but 2% of the brightest pixels in the difference image data output by step 200, thereby to extract possible microcalcifications. Then area filtering utilizing morphological erosion is performed, as described in Ser. No. 07/915,631, now U.S. Pat. No. 5,537,485, to eliminate very small signals caused by image noise. Next an adaptive local grey-level threshold is used to reduce further the number of false signals. The thresholding is based on the local statistics (mean and standard deviation) of the pixel values in a 5.1×5.1-mm area in the image. The threshold is set equal to a multiple of the standard deviation plus the mean. Typically multiples of 2.8–4.2 are used. The remaining signals are subjected to texture analysis in step 400 and then are subjected to a cluster filtering process in step 500, as described in Ser. No. 07/915,631, now U.S. Pat. No. 5,537,485.

The cluster filtering technique performed in step 500 results in the identification of locations in the difference image which have potentially problematic microcalcifications. The difference image data in a region surrounding the locations identified in step 500 are then subjected to feature extraction processing in step 600 to determine the area, contrast (i.e., thickness) and background pixel values of the difference image data in the regions evaluated as identified in step 500. An area vs. contrast test is then performed in step 700 to eliminate a number of image locations of interest as corresponding to false-positives, and a contrast vs. background test is performed in step 800, again in order to eliminate image locations determined to correspond to false-positive identifications. In step 900, a cluster filtering of the remaining identified locations is performed. Clusters remaining after step 900 are then identified in step 1000 for enhancement processing according to the present invention.

Enhancement processing performed according to the present invention results from several studies conducted by the inventors. In one study, two methods for reducing the false-positive rate, based on analysis of local edge gradients, were investigated. The first method is an edge-gradient analysis and involves the determination of local edge-gradient values for the perimeter pixels of detected microcalcification signals. This analysis results in removing false-positive microcalcification signals that look like subtle or blurred microcalcifications, and other false-positive signals due to artifacts. The second method is a linear-pattern analysis, which determines local gradient values in linear arrays. This analysis results in eliminating false-positive microcalcification signals that are caused by bright linear patterns from normal breast anatomy.

In this study, two data sets were used, one including 39 mammograms for initial development (training set) and another 50 mammograms for verification (testing set). Each of the two sets contained 41 clusters of microcalcifications. Conventional screen-film mammograms were digitized on a Fuji drum scanner with a pixel size of 0.1 mm×0.1 mm. The optical density in the range from 0.2 to 2.75 was linearly quantized to 10-bit gray scales. Typical matrix size of the digitized mammograms was 800×1000 for the first database and 1000×2000 for the second database. 800×1000 region for the first database covered most of the actual breast area. The locations of "true" individual microcalcifications in the first database and only the locations of clusters in the second database were identified by an experienced radiologist. The average diameter and the average contrast in optical density of "true" microcalcifications were 0.31 mm (standard deviation, $\sigma=0.12$) and 0.11 ($\sigma=0.04$), respectively, for 39 mammograms, and 0.39 mm ($\sigma=0.21$) and 0.15 ($\sigma=0.06$), respectively, for 50 mammograms.

The locations of clusters, which contain three or more microcalcification signals within a given region area, were detected with the automated detection scheme shown in FIGS. 1 and 2 and as described in more detail in Ser. No.

07/915,631, now U.S. Pat. No. 5,537,485. For a digitized mammogram, a difference image was created by subtracting a signal-suppressed image from a signal-enhanced image. Global thresholding technique and an adaptive local thresholding technique were then employed to identify candidates of individual microcalcification signals. Feature analyses, including the first moment of the power spectrum, were applied to eliminate some false-positive microcalcification signals. After clustering (or grouping) the microcalcification signals, the locations of the centroids of clusters were obtained as the final computer output. The locations of microcalcification signals in each detected cluster was determined by the computer. The scheme correctly detected 35 true-positive clusters and 91 false-positive clusters in 39 mammograms, which consists of 169 true-positive and 311 false-positive individual microcalcification signals. For 50 mammograms, the scheme detected 37 true-positive and 294 false-positive clusters. In this study, an IBM RISC 6000 Series Powerstation 570 computer was used for all of the computations.

Based on the experience with the detection of lung nodules in chest radiographs (see T. Matsumoto, et al, "Image feature analysis of false positives produced by an automated computerized scheme for the detection of lung nodules in digital chest radiographs", Invest. Radiol. 27, 587–597 (1992), and U.S. Pat. No. 4,907,156), it is useful to examine the causes of false-positive microcalcification signals in order to devise methods for reducing them. The inventors classified the appearance of the detected false-positive microcalcification signals in 39 mammograms into four major categories: (1) microcalcification-like noise pattern, (2) artifacts, (3) linear pattern, and (4) others including false-positive signals that appeared on ducts, step-like edges or ring patterns. The percentages of the false-positive microcalcification signals in four categories are shown in Table I. In total, there are 311 false-positive microcalcification signals in 39 mammograms, detected by a computerized scheme.

TABLE I

| Cause of false positives | Number of false positives | |
| --- | --- | --- |
| Microcalcification-like noise pattern | 210 | (67.5%) |
| Linear pattern | 71* | (22.8%) |
| Artifacts | 21 | (6.8%) |
| Others | | |
| Ducts | 7* | (2.3%) |
| Step-like edges | 4 | (1.3%) |
| Ring pattern | 1 | (1.0%) |
| Total | 311 | (100.0%) |

Many of microcalcification-like noise patterns look like subtle microcalcification. With careful observation, however, these noise patterns are visually different from "true" microcalcifications because the "edges" of these noise patterns are not as sharp as those of "true" microcalcifications. Artifacts are generally caused by dusts or scratches on films as well as noise in the digitization process. False-positive microcalcification signals due to artifacts have steeper profiles (or higher contrast) than "true" microcalcifications. For linear patterns, false-positive microcalcification signals are located on or along the top of bright linear patterns, which are probably due to breast parenchyma. It is important to note that the percentage of linear patterns included in "true" microcalcification signals is only 3%, which is much smaller than that (23%) in false-positive microcalcification signals.

Figure 4:
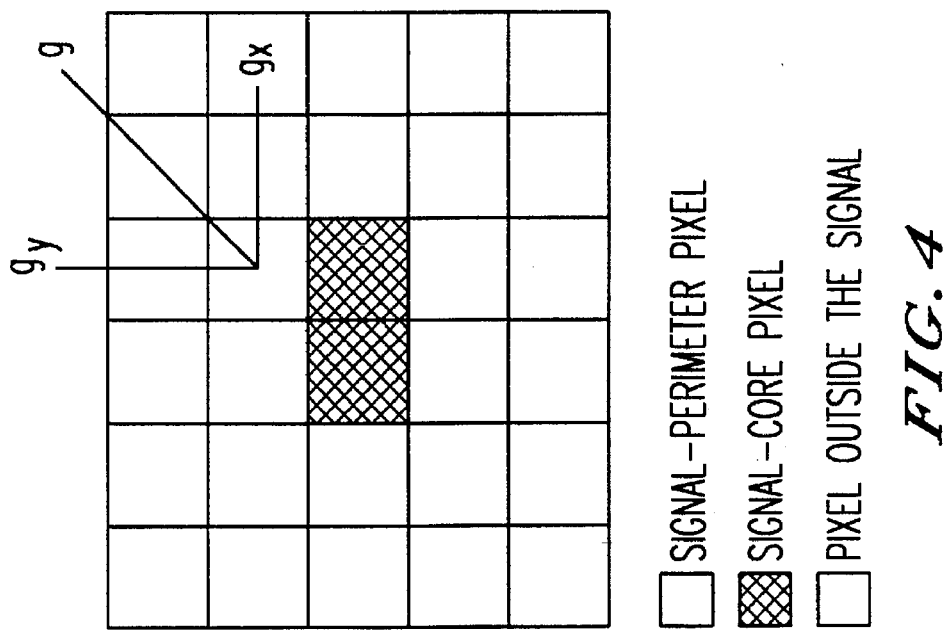
FIG. 4 is an illustration of signal-perimeter pixels (or peripheral pixels of a signal) of a microcalcification signal.
Figure 3:
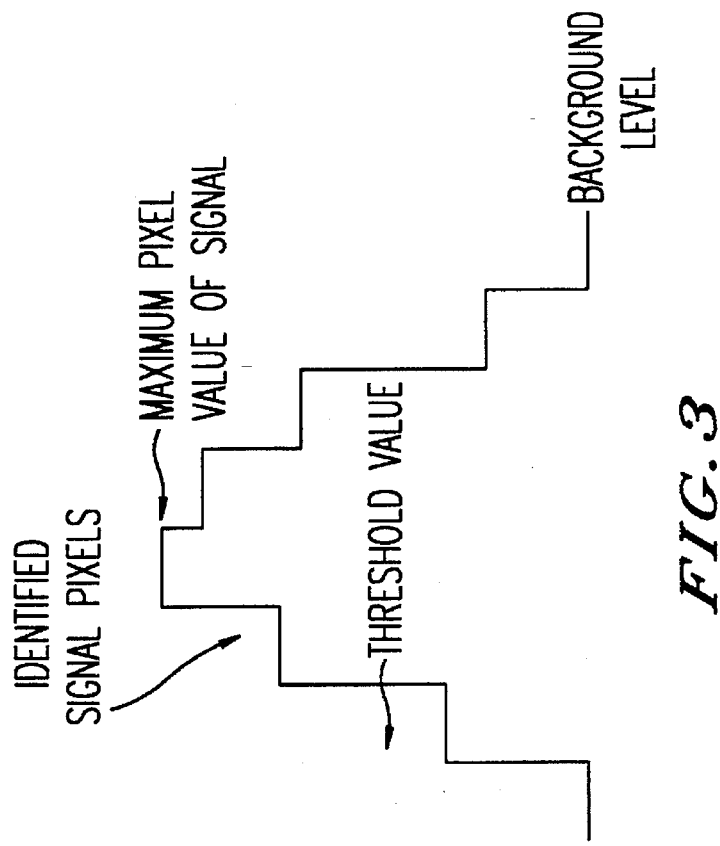
FIG. 3 is an illustration of threshold level used for determination of signal pixels due to microcalcification signal in background trend-corrected ROI.

In determining the edge-gradients according to the present invention, local edge gradients for the signal-perimeter pixels are determined for each detected microcalcification signal. First, a region of interest (ROI) with a matrix size of 32×32 is placed such that the centroid of the detected microcalcification signal is located at the center of the ROI. The non-uniform background (low spatial frequency trend) is corrected by using a two-dimensional surface-fitting technique with a third degree polynomial. (See S. Katsuragawa et al., "Image feature analysis and computer-aided diagnosis in digital radiography: Detection and characterization of interstitial lung disease in digital chest radiographs", Med. Phys. 15, 311–319 (1988).) In the background corrected ROI, a pixel having the local maximum value is searched within a small circle of three-pixel radius centered on the centroid of the signal. Gray-level thresholding is then employed to identify pixels representing the detected signal. As shown in FIG. 3, half of the local maximum pixel value are used as a threshold value for identifying pixels belonging to a signal. Signal-perimeter pixels are determined as peripheral pixels of the signal pixels, as shown in FIG. 4. Absolute values of edge gradients, g, are calculated at each signal-perimeter pixel of the signal in the digitized mammogram by using the equation $$g = \sqrt{g_x^2 + g_y^2},$$

where $g_x$ and $g_y$ correspond to the difference in pixel values between the signal-perimeter pixel and the adjacent pixel outside the signal area, in horizontal and vertical directions, respectively. In some cases, more than one edge-gradient value can be calculated for a signal-perimeter pixel. All calculated edge gradients are averaged to represent the edge gradient of the signal. Also determined is the average pixel value in a 9×9 ROI, whose center is located at the centroid of the signal, to represent the average pixel value of the microcalcification signal.

Features similar to the local edge-gradient value and the average pixel value for each microcalcification signal are also determined to represent features of each cluster. For each cluster, the edge-gradient values and the average pixel values of three microcalcification signals having the three largest edge-gradient values in the cluster are averaged and used as the average edge-gradient value and the average pixel value of the cluster, respectively. Since features of a cluster will in general be different from features of individual microcalcifications, the present invention includes use of these features to remove more false positives than either one of these features alone.

Figure 5A:
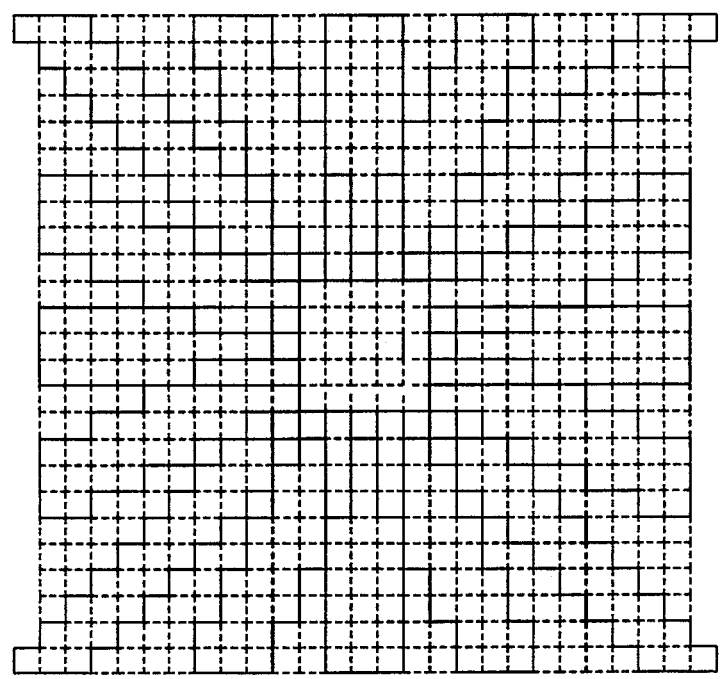
FIG. 5(a) is an illustration of different orientations of sets of templates used for calculation of local gradient values, where, for simplicity, only central templates A of FIG. 5(b) in eight orientations are illustrated.
Figure 5B:
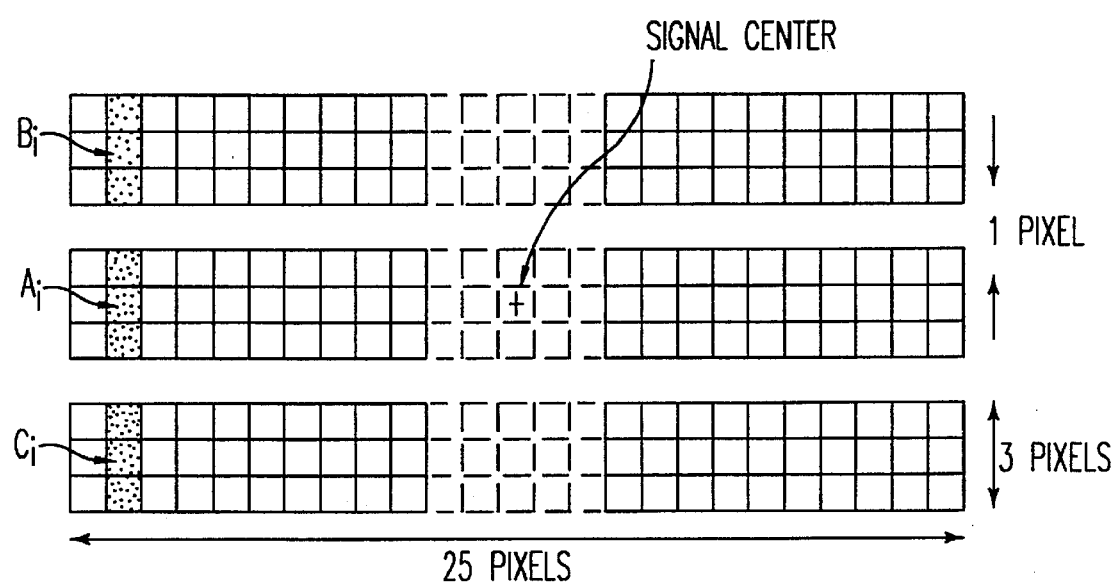
FIG. 5(b) is an illustration of a set of three templates A, B, C used for calculation of local gradient values, with the set shown oriented in a horizontal direction.
Figure 6:
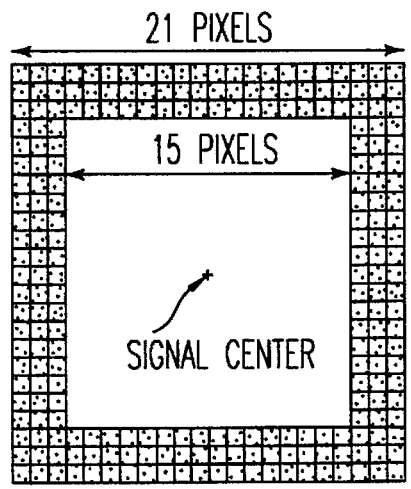
FIG. 6 is an illustration of a box-rim region used for calculation of the standard deviation of pixel values in background area adjacent to a detected microcalcification signal.

To determine a physical measure of linear patterns, three linear templates in sixteen different orientations, as illustrated in FIG. 5(a), are used. Narrow (3 pixels) and long (25 pixels) templates A, B, C are placed around each microcalcification signal such that the center of the central template, A, is located at the centroid of the signal, as shown in FIG. 5(b). A pair of two adjacent templates B, C are placed in the same orientation as that of the central template; and each template A, B, C consists of three columns, i.e., three-pixel width. Local gradient values are calculated for each set of corresponding element (or pixel) along the templates except for the five central elements. The local gradient value, $G_i$, was defined by $$G_i = 2A_i - B_i - C_i,$$

where $A_i$, $B_i$ and $C_i$ are average pixel values for the i-th element of the corresponding columns of the three templates A, B, C. Calculated local gradient values are thresholded using a threshold level equal to the standard deviation of the pixel values for the pixels in a box-rim region surrounding the signal. As shown in FIG. 6, the outer and inner size of the box-rim region is 21×21 and 15×15, respectively. This thresholding is effective in distinguishing an element that is likely to have a sharp peak, i.e., an indication of a part of a linear pattern, from noise. The fraction of the number of the $G_i$ elements, having the local gradient values above the threshold level is calculated for each set of templates in different orientations. Finally, the maximum of these fractions among all orientations is defined as the degree of linearity for a linear pattern. That is a measure of a linear pattern that may be included in the detected microcalcification signal. If the direction of a linear pattern coincides with that of a template set, then the linear pattern would be located in the central template at a certain orientation. In such a case, most of local gradient values obtained by Eq. (2) along the long axis of the template would be greater than the threshold level. Therefore, false-positive microcalcification signals due to linear patterns are expected to have relatively large measures (degree of linearity) than for "true" microcalcifications.

Of interest is that a subjective evaluation of linearity by five observers (a radiologist and four medical physicists) correlated well with the linear pattern analysis performed according to the present invention.

Figure 7:
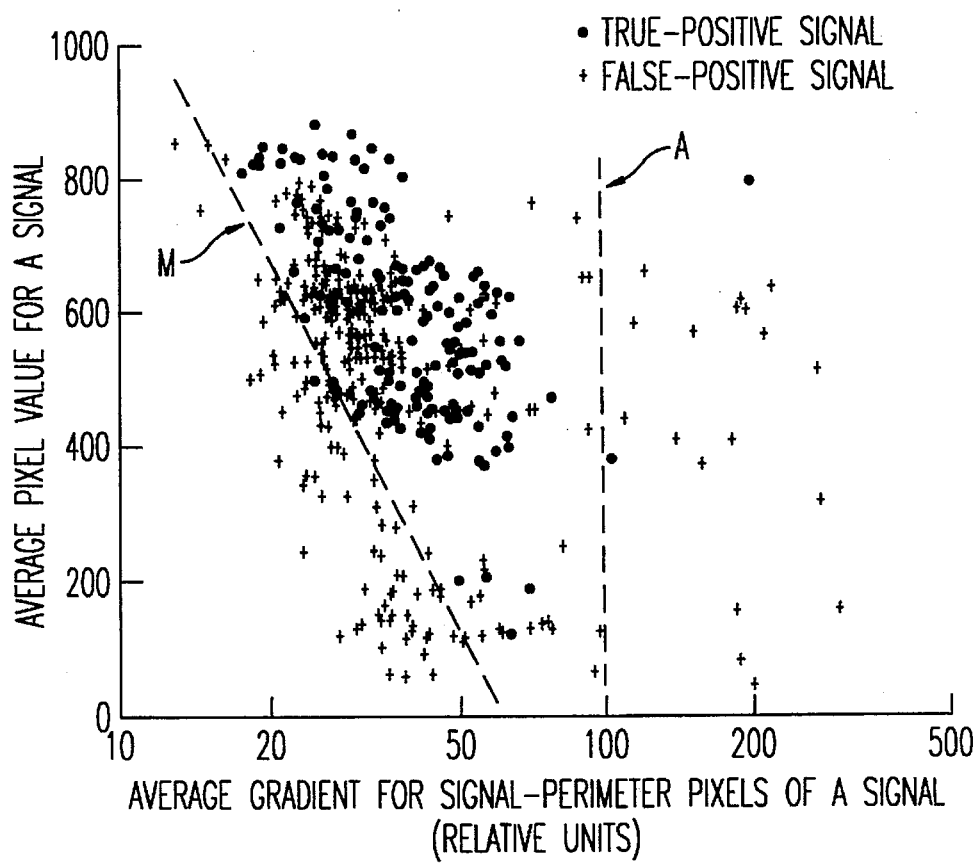
FIG. 7 is a graph illustrating the relationship between the average edge=gradient values at signal-perimeter pixels and the average pixel values for individual microcalcification signals detected in 39 mammograms, wherein threshold lines A and M are used to eliminate false-positive microcalcification signals.

FIG. 7 shows the relationship between the average edge-gradient values at signal-perimeter pixels and the average pixel values for 169 true-positive and 311 false-positive microcalcification signals that were detected in 39 mammograms of the training database. Although false-positive signals are distributed more widely than the true-positive signals, it appears that some of the false-positive signals can be divided into two groups. False-positive signals in one group have very large edge-gradient values, whereas those in the other group have small edge-gradient values. The first group contains microcalcification signals due to artifacts, which generally include very sharp edges. Many of the false-positive microcalcification signals in the second group have smaller edge-gradient values than most of the true-positive signals that have the same average pixel values. These false-positive signals are caused by microcalcification-like noise patterns.

Figure 8:
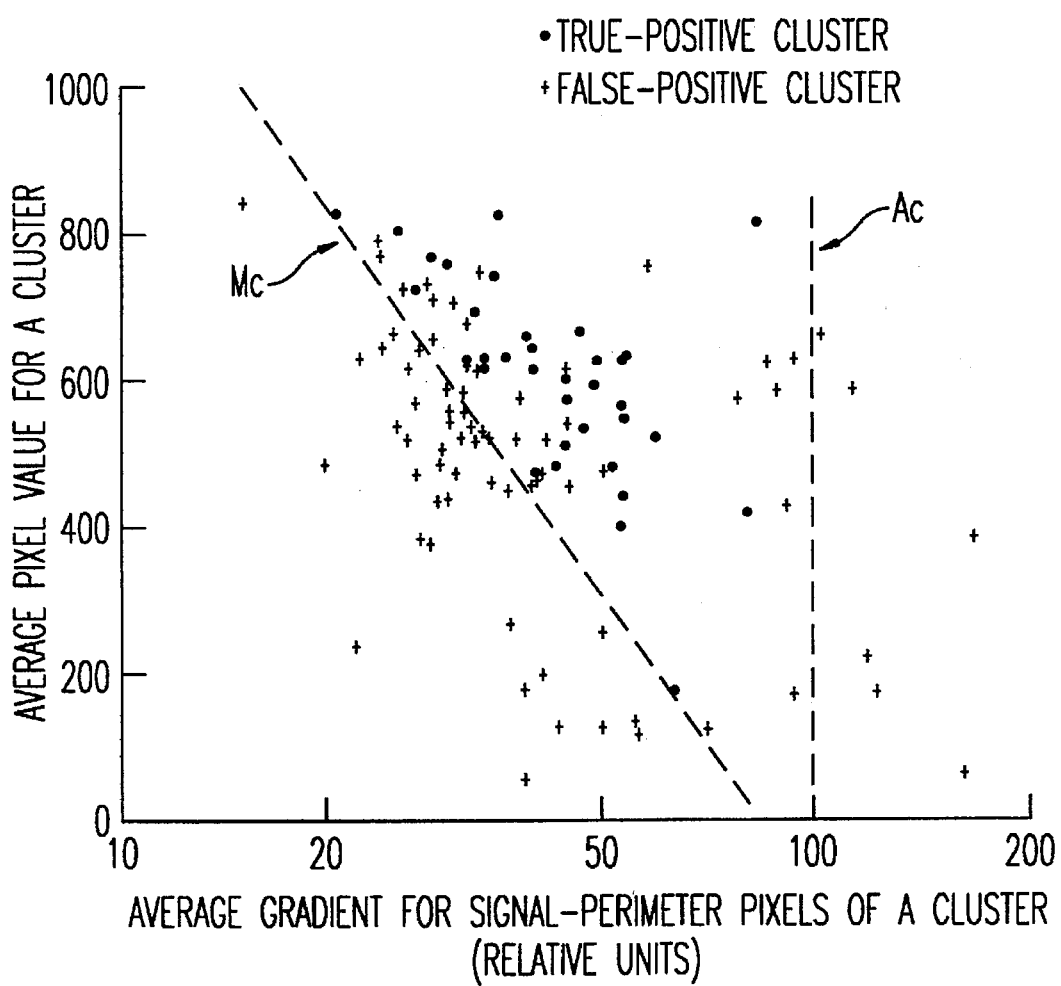
FIG. 8 is an illustration of the relationship between the average edge-gradient values and the average pixel values for clusters detected in 39 mammograms, wherein the threshold lines Ac and Mc are used to eliminate false-positive clusters.

For analysis of image features on clustered microcalcification instead of individual microcalcifications, FIG. 8 illustrates the relationship between the average edge-gradient values and the average pixel values for all of the clusters. It is apparent that the distribution of these data for clusters has a trend similar to that for individual signals shown in FIG. 7. Therefore, the characteristics of clusters generally reflect the properties of the signals that compose the clusters.

To eliminate false-positive signals, it is possible to employ three different schemes (A, B and C) using the results shown in FIGS. 7 and 8. In scheme A, only the result shown in FIG. 7 are used. First, microcalcification signals that have edge-gradient values larger than those shown by a threshold line A in FIG. 7 are eliminated, and also those which have average edge-gradient values and average pixel values smaller than those shown by another threshold line M. Subsequently, if the number of remaining microcalcification signals in each cluster become smaller than three, then the cluster is eliminated. In scheme B, cluster elimination is performed directly on clusters, instead of individual microcalcification signals, in a manner similar to scheme A by using only the thresholds shown in FIG. 8. Two threshold lines Ac and Mc in FIG. 8 are then used to eliminate false-positive clusters. In scheme C, results from scheme A and B are combined such that only those locations of clusters that remain in both schemes A and B are used as the final result. In other words, any cluster removable by either scheme A and B would be eliminated. The reduction in the number of false positives and true positives for individual microcalcification signals and clusters for the three schemes is summarized in Table II, which illustrates the reduction in the number of false positives and true positives for individual microcalcification signals and for clusters by using (a) edge-gradient analysis, (b) linear-pattern analysis, and (c) the combination of two analyses on 39 mammograms. There are 311 false-positive and 169 true-positive signals. There are 91 false-positive and 35 true-positive clusters.

TABLE II

| Analysis method (a), (b) and (c); and scheme A, B and C | | Number of individual microcalcifications eliminated | | Number of clusters eliminated | |
|---|---|---|---|---|---|
| | | False positives | True positives | False positives | True positives |
| Edge-gradient analysis | A | 104 (33.4%) | 4 (2.4%) | 40 (44.0%) | 1 (2.9%) |
| | B | — | — | 45 (49.5%) | 0 (0.0%) |
| | C | — | — | 54 (59.3%) | 1 (2.9%) |
| Linear-pattern analysis | A | 60 (19.3%) | 6 (3.6%) | 25 (27.5%) | 0 (0.0%) |
| Combined method | A | 150 (45.3%) | 10 (5.9%) | 57 (62.6%) | 1 (2.9%) |
| | B | — | — | 59 (64.8%) | 0 (0.0%) |
| | C | — | — | 66 (72.5%) | 1 (2.9%) |

Nineteen of the 104 false-positive microcalcification signals were eliminated in scheme A because they had large edge-gradient values. These 19 signals include 17 artifact signals, which correspond to 81% of all of the microcalcification signals due to artifacts. Scheme A also removed 53 false-positive microcalcification signals due to microcalcification-like noise patterns corresponding to 25% of all of the microcalcification-like noise patterns. With scheme A, 40 false-positive (44%) and one true-positive clusters were eliminated. However, scheme B provided a better performance by eliminating 45 false-positive clusters (49%) without any loss of true-positive cluster. Since scheme C is a combination of scheme A and B, it generally eliminates more false-positive and true-positive clusters. On the 39 mammograms, scheme C eliminated 54 false-positive (59%) and one true-positive clusters. These results indicate that the two schemes A and B can remove clusters in somewhat different locations and thus may be useful if the two schemes are properly combined with appropriate threshold lines.

Figure 9:
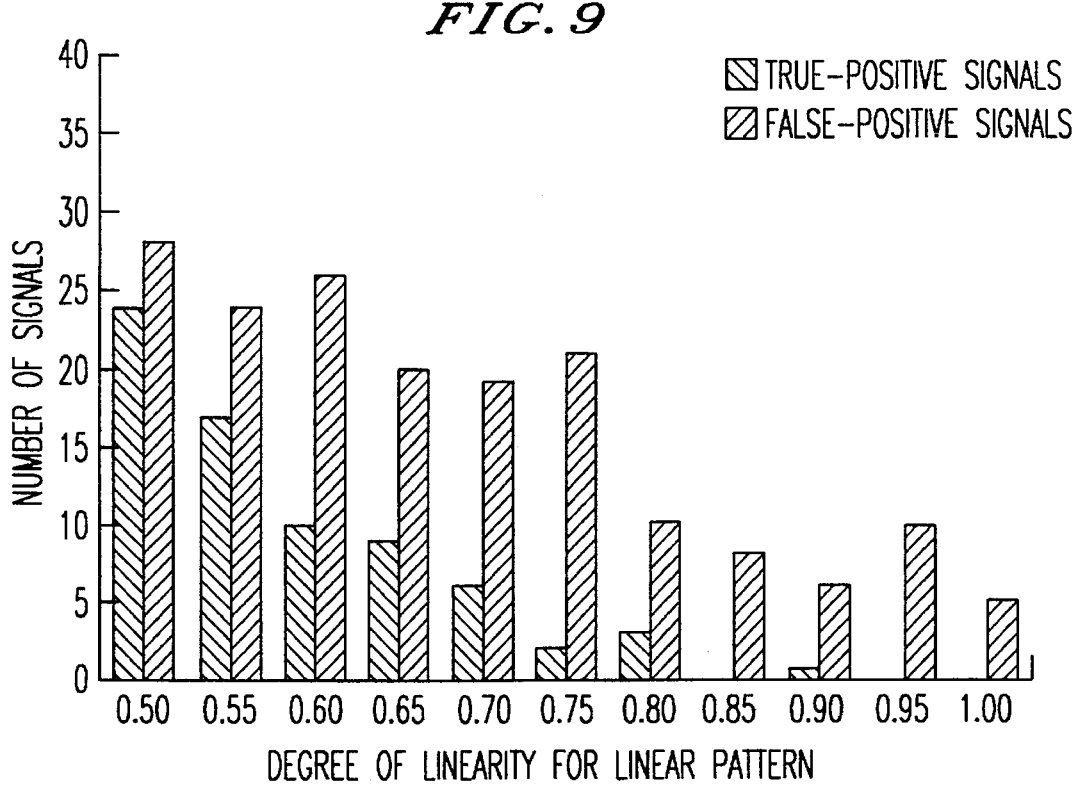
FIG. 9 is a chart illustrating histograms of physical measures of linear patterns for individual microcalcification signals detected in 39 mammograms.

Physical measures of linear patterns were also calculated for the true-positive signals detected in 39 mammograms. FIG. 9 shows histograms of the degree of linearity (shown only for 0.5 and above) of linear patterns calculated for true-positive and false-positive microcalcification signals. It is clear in FIG. 9 that most microcalcification signals with large degree of linearity are due to false-positive microcalcification signals. Therefore, it is possible to eliminate some of false-positive signals by the linear-pattern analysis, although a small number of true-positive signals may be lost.

Figure 10:
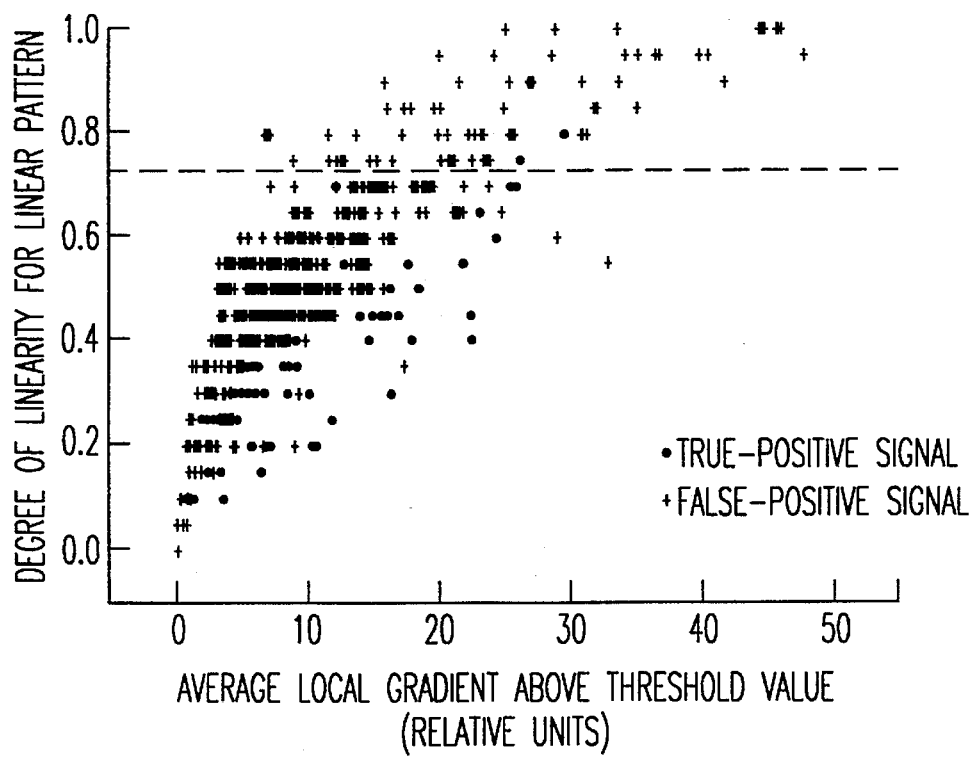
FIG. 10 is an illustration of the relationship between physical measures of linear patterns and average local gradient values above the threshold level for individual microcalcification signals detected in 39 mammograms.

FIG. 10 shows the relationship between the degree of linearity for linear patterns and the average local gradient values above the threshold level, which is equal to the standard deviation of the pixel values in box-rim regions. The average local gradient values were determined as a potential measure of the conspicuity of the linear patterns. It is apparent in FIG. 10 that the two measures are loosely related, namely, the greater the degree of linearity, the greater the average local gradient in general. Therefore, it is possible to use either one of the two measures or both in eliminating false-positive microcalcification signals due to linear patterns. However, it is apparent that the degree of linearity is a better indicator, since more false-positive microcalcification signals can be removed with this measure.

To eliminate false-positive signals and clusters, a scheme similar to scheme A used in the edge-gradient analysis is employed. Microcalcification signals having the degree of linearity equal to or larger than 0.75, which is shown by the threshold level L in FIG. 10, are eliminated. For each cluster, if the number of remaining microcalcification signals in the cluster is less than three, then the cluster is eliminated. Table II shows a summary of the reduction of false positives and true positives for individual microcalcification signals and clusters. By applying the linear-pattern analysis, 19% of the false-positive microcalcification signals and 45 of true-positive microcalcification signals are eliminated. In these eliminated signals, 55% of the false-positive microcalcification signals had an average subjective rating of 1.2 or greater. For clusters, 25 false-positive clusters (27%) are eliminated without any loss of true-positive clusters.

The inventors also applied both the edge-gradient analysis and linear-pattern analysis on the output of our current CAD scheme obtained from 39 mammograms of the training set. The results shown in the above Table II indicate that the combination of the two methods is more effective in elimination of false positives than either one of the methods. It is apparent that the false-positive signals and clusters eliminated by one method do not overlap completely with those by the other method. Therefore, a higher performance level is obtained by combining the two methods. The false-positive rate can be 0.64 cluster per mammogram with the sensitivity of 83%.

To verify the usefulness of the edge-gradient and linear-pattern analyses, these methods were applied to the second database for testing, which included 50 mammograms containing 41 clusters of microcalcifications. With this database, the prior CAD scheme detected 272 true-positive and 1242 false-positive microcalcification signals, which correspond to 37 true-positive and 294 false-positive clusters. The results of the edge-gradient and linear-pattern analyses are summarized in Table III, which illustrates the reduction in the number of false positives and true positives for individual microcalcification signals and for clusters by using (a) edge-gradient analysis, (b) linear-pattern analysis, and (c) the combination of two analyses on 50 mammograms. There are 1242 false-positive and 272 true-positive signals. There are 294 false-positive and 37 true-positive clusters.

TABLE III

| Analysis method (a), (b) and (c); and scheme A, B and C | | Number of individual microcalcifications eliminated | | Number of clusters eliminated | |
|---|---|---|---|---|---|
| | | False positives | True positives | False positives | True positives |
| Edge-gradient analysis | A | 437 (35.2%) | 3 (1.1%) | 131 (44.6%) | 0 (0.00%) |
| | B | — | — | 158 (53.7%) | 1 (2.7%) |
| | C | — | — | 182 (61.9%) | 1 (2.7%) |
| Linear-pattern analysis | A | 322 (25.9%) | 14 (5.1%) | 102 (34.7%) | 0 (0.0%) |
| Combined method | A | 680 (54.8%) | 17 (6.3%) | 207 (70.4%) | 0 (0.0%) |
| | B | — | — | 216 (73.5%) | 1 (2.7%) |
| | C | — | — | 237 (80.6%) | 1 (2.7%) |

It is apparent that each of the two methods and their combination provide results comparable to those obtained for 39 mammograms in the first database. With scheme C, the sensitivity was maintained at a high level of 88% while the false-positive rate decreased to 1.1 clusters per mammogram.

In the edge-gradient analysis, two thresholds for elimination of both individual microcalcification signals (scheme A) and clusters (scheme B) are employed. It is possible that a true-positive cluster includes one or more false-positive microcalcification signals. If such false-positive signals are due to artifacts and thus have large edge-gradient values, then the edge-gradient value of the cluster will be large because the three largest edge-gradient values of the signals are used to represent the cluster. As a result, some of the true-positive clusters will likely be eliminated. It may not be desirable to eliminate every cluster that has a large edge-gradient value in scheme B. Therefore, it might be inadequate to eliminate clusters by using their edge-gradient values. In scheme A, however, elimination of individual microcalcification signals having large edge-gradient values would not cause such problems of removing "true" clusters.

As mentioned earlier, false-positive microcalcification signals due to artifacts have very sharp edges. Therefore, it is not difficult to calculate edge-gradient values of microcalcification signals by other methods for elimination of false-positive microcalcification signals due to artifacts. One method is to use the maximum edge-gradient calculated at signal perimeter-pixels for representing the microcalcification signal, instead of the average edge-gradient. Results obtained with this alternative method on 39 mammograms were comparable.

Edge-gradient values for signal-perimeter pixels were employed for eliminating false positives in this study. The inventors examined using edge-gradient values calculated in two different types of regions: (1) small square ROIs with different sizes placed over the detected microcalcification signal and (2) a set of two ROIs, i.e., a small square ROI over the signal for analysis of signal edges and an adjacent box-rim ROI for analysis of edges in background. However, the edge-gradient values for signal-perimeter pixels provided the best result among other methods examined. This implies that features of edges of microcalcification signals might be best characterized by local edge-gradient values at signal-perimeter pixels of the signal.

The linear-patten analysis involves parameters, such as the size of templates and the number of template orientations that can affect the result. The inventors examined four different conditions which included 8, 16, 24 and 32 orientations without changing other parameters. Results indicated that the greater the number of orientations, the greater the number of individual microcalcification signals that can be removed. The numbers of signals removed with templates in 8, 16, 24 and 32 orientations are 5, 6, 9 and 7 for true-positive signals, and 40, 60, 71 and 76 for false-positive signals, respectively, in 39 mammograms. Therefore, a large number of false-positive microcalcification signals could be eliminated if a large number of orientations were used. The use of a large number of template orientations will require a long computation time, and the number of microcalcification signals removed tends to be saturated. Therefore, 16 orientations were employed. However, if a faster computer is used, a larger number of template orientations can be used. For the length of template, we examined 25-, 35- and 45-pixel-long templates were examined. The longer the template, the fewer were the number of signals removed. Six, two, and only one true-positive signals, and 60, 28 and 19 false-positive signals were removed with 25-, 35- and 45-pixel-long templates, respectively. In addition, most false-positive signals eliminated using the 45 pixel-long templates were included in those eliminated using the 25-pixel-long templates, probably because some linear patterns are not long and linear enough to overlap with the entire 45-pixel-long template.

Recapitulating, in the first study above described, the inventors analyzed and classified causes of false positives into several categories, by which methods for quantifying image features of various patterns of false positives were derived. By using these methods, the inventors were able to eliminate many false-positives including microcalcification-like noise patterns and linear patterns, which are dominant causes of false positives. By employing the combination method of the edge-gradient analysis and linear-pattern analysis, approximately 70% of detected false-positive clusters were eliminated, while maintaining a high detection rate of true-positive clusters, such that the number of false-positive clusters is now expected to be 0.9 per mammogram at the sensitivity of approximately 85% in detecting clustered microcalcifications.

In a second study performed by the inventors, as next discussed in more detail, a multiple difference-image technique was investigated to increase the sensitivity of a computerized scheme for detection of clustered microcalcifications in digitized mammograms. The technique was used in two types of schemes. In the first scheme, locations of candidates of microcalcification signals detected in two different images were merged by using logical "OR" operation after signal extraction processes. In the second scheme, locations of detected clusters were merged by also using logical "OR" operation after clustering. Three combinations of band-pass filters were examined on these two new schemes. Results indicated that the new schemes provided a higher sensitivity by approximately 5% than the current scheme on a database including 39 mammograms, although the detection rate of false-positive clusters also increased. This improvement of the sensitivity was probably caused by different sensitiveness of two different filters depending on different sizes of microcalcifications. Based on the second study the inventors determined that the multiple difference-image technique is useful to increase the sensitivity, if an appropriate combination of filters is used.

Figure 11A:
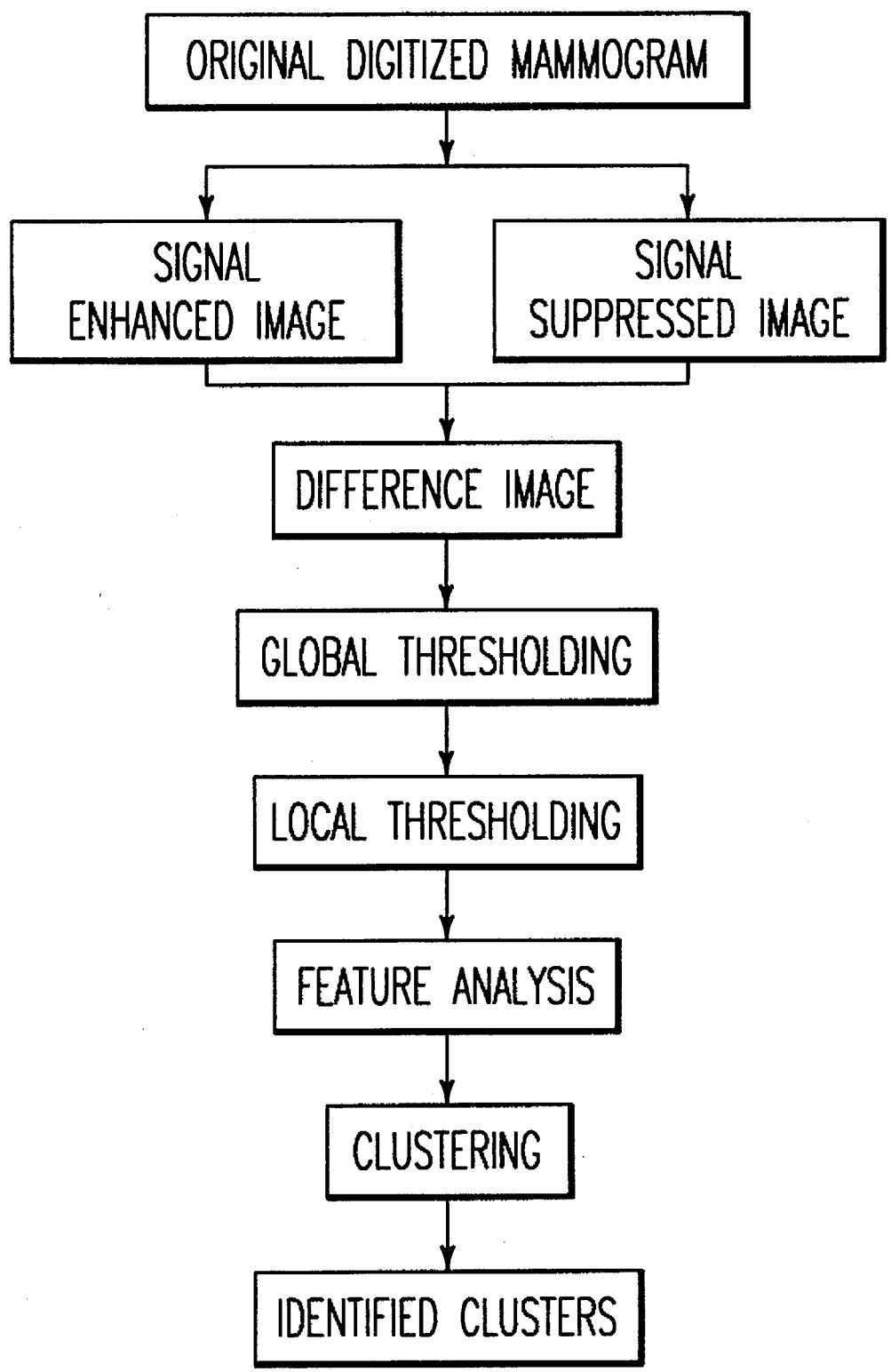
FIG. 11(a) is an abbreviated schematic flow chart illustrating the processing steps of the method shown in FIG. 1.

As above indicated, the second study investigated a multiple difference-image technique in which two or more difference images are created from a digitized mammogram. Microcalcifications with a certain range of sizes are enhanced in one of the difference images, and those with another range of sizes are enhanced in another difference image. Multiple sets of signal-enhancement filters and signal-suppression filters are designed to enhance microcalcifications of different size. These difference images are thresholded to identify candidates of microcalcification signals and then the signals are used as the input to the subsequent detection steps. Results demonstrate that this multiple-difference image technique is useful to increase the sensitivity of the CAD scheme. In the second study the first 39 mammogram database of the first study, as above described, was utilized. To investigate the multiple difference-image technique, three types of schemes for detection of clustered microcalcifications in mammograms were used. FIG. 11(a) shows an abbreviated flow chart of method of FIG. 1. A signal-enhanced image 210 and a signal-suppressed image 220 were created from an original digitized mammogram 100 using linear spatial filters. Then a difference image 230 was obtained by subtracting the signal-suppressed image from the signal-enhanced image. Signals were extracted from the difference image using two thresholding techniques, namely, global thresholding, area filtering (not shown) and local adaptive thresholding. The threshold value for global thresholding was set so that 2% of the pixels with the highest values are kept. For each signal, some local threshold values were selected to examine the performance of the CAD scheme. Each of the local threshold values is determined by using the equation shown by $$T = A + (S_d \times F),$$

where T, A, $S_d$ and F correspond to a local threshold value, the average pixel value in a 51×51 region of interest (ROI) including the signal, the standard deviation of the pixel values in the ROI, and a local threshold factor (LTF), respectively. Six local threshold factors, i.e., 4.2, 4.0 3.8, 3.6, 3.4 and 3.2 were used. Features including the first moment of the power spectrum were determined as indicators for eliminating some of the false-positive signals. Clustering (or grouping) was performed on the remaining signals in the final step to identify locations of clusters. A detected cluster was considered as a true-positive detection, if the distance between the centroid of the detected cluster and that of a "true" cluster was 6 mm or less.

Figure 11B:
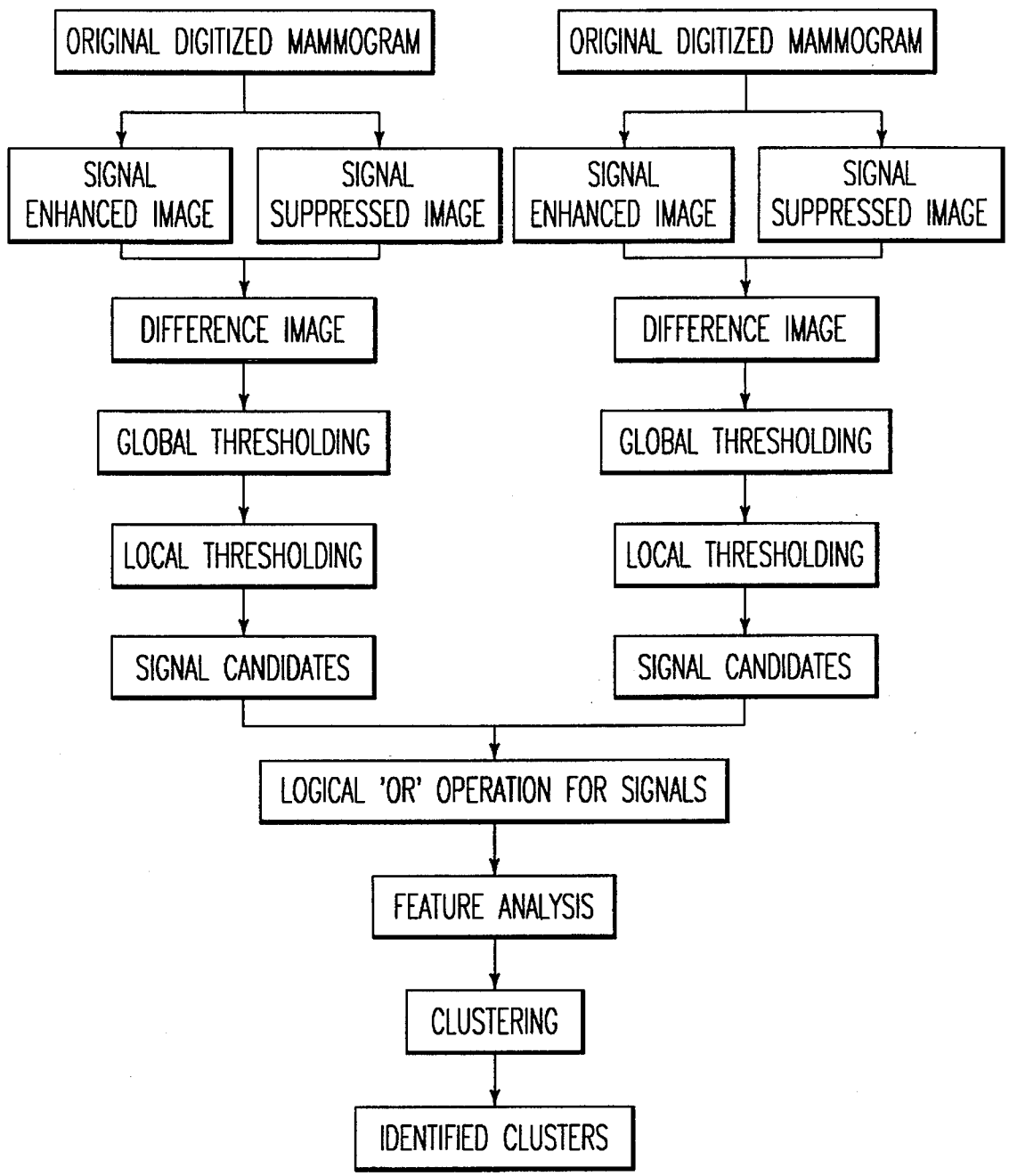
FIG. 11(b) is a schematic flow chart illustrating processing steps of a multiple difference imaging technique performed according to the present invention.

In the second scheme, denoted as M1, two difference images were employed to separately extract signals. As shown in FIG. 11(b), two sets of signal-enhanced images and signal-suppressed images were created using two sets of linear spatial filters. Two sets of locations of signal candidates identified at the local thresholding were merged into one set based on a logical "OR" operation. If the distance between a signal identified in one difference image and another identified in the other difference image is three pixels or less, one of the two signals was removed, assuming that the two are identical signals. The merged set of signal locations were subjected to the subsequent feature analysis.

Figure 11C:
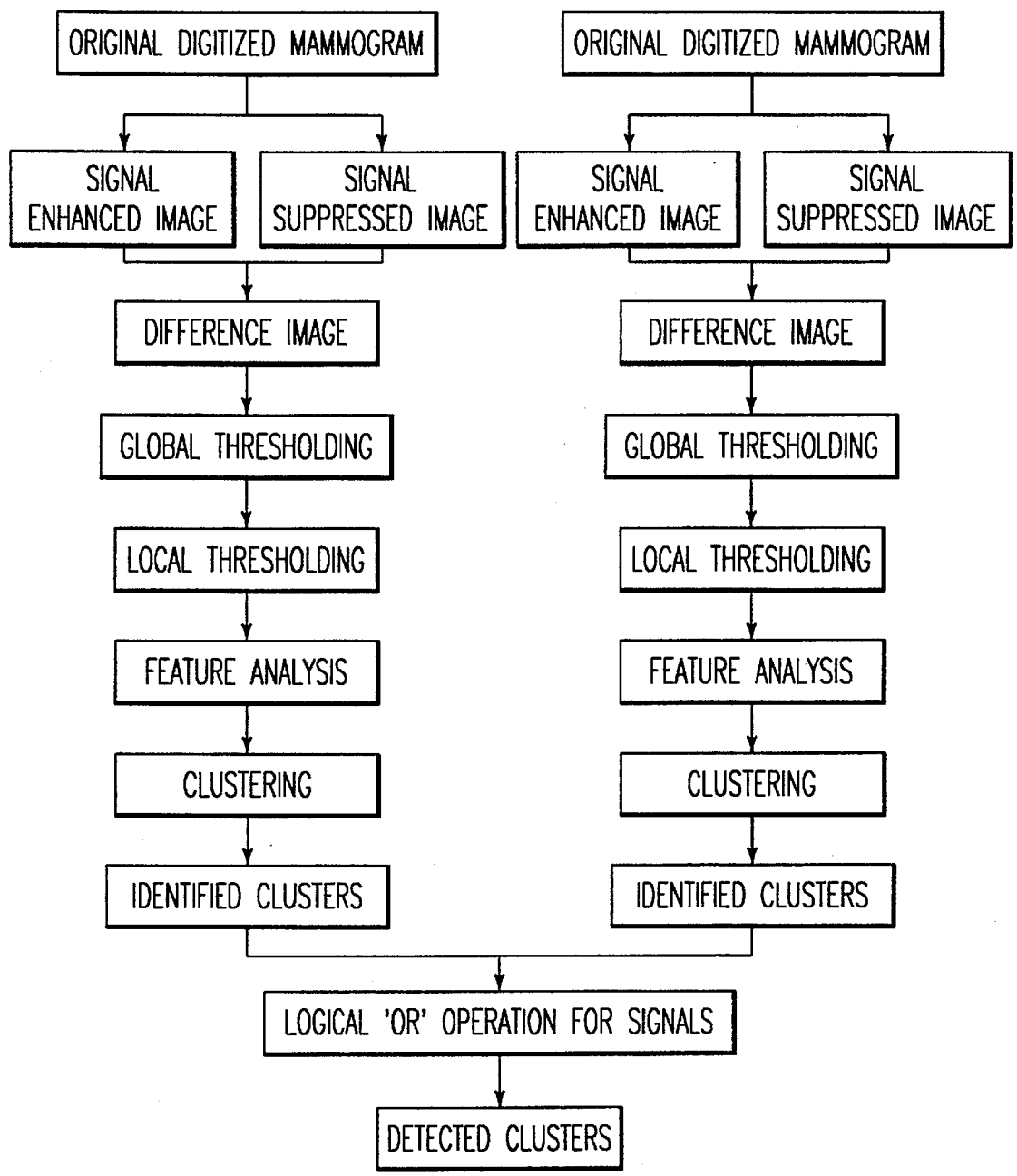
FIG. 11(c) is a schematic flow chart illustrating a variation of the multiple difference imaging technique of FIG. 11(b)

The third scheme, called M2, incorporates the entire C scheme of FIG. 11(a) twice. FIG. 11(c) illustrates the M2 scheme. The C scheme was first employed twice, each with a different set of filters. The locations of clusters identified with the first C scheme were compared with those identified with the second C scheme. If the location of the center of a cluster in the first set is 60 pixels or less from the center of another cluster in the second set, then these two clusters were regarded as the same cluster. This corresponds to logical "OR" operation for cluster locations.

Figure 12A:
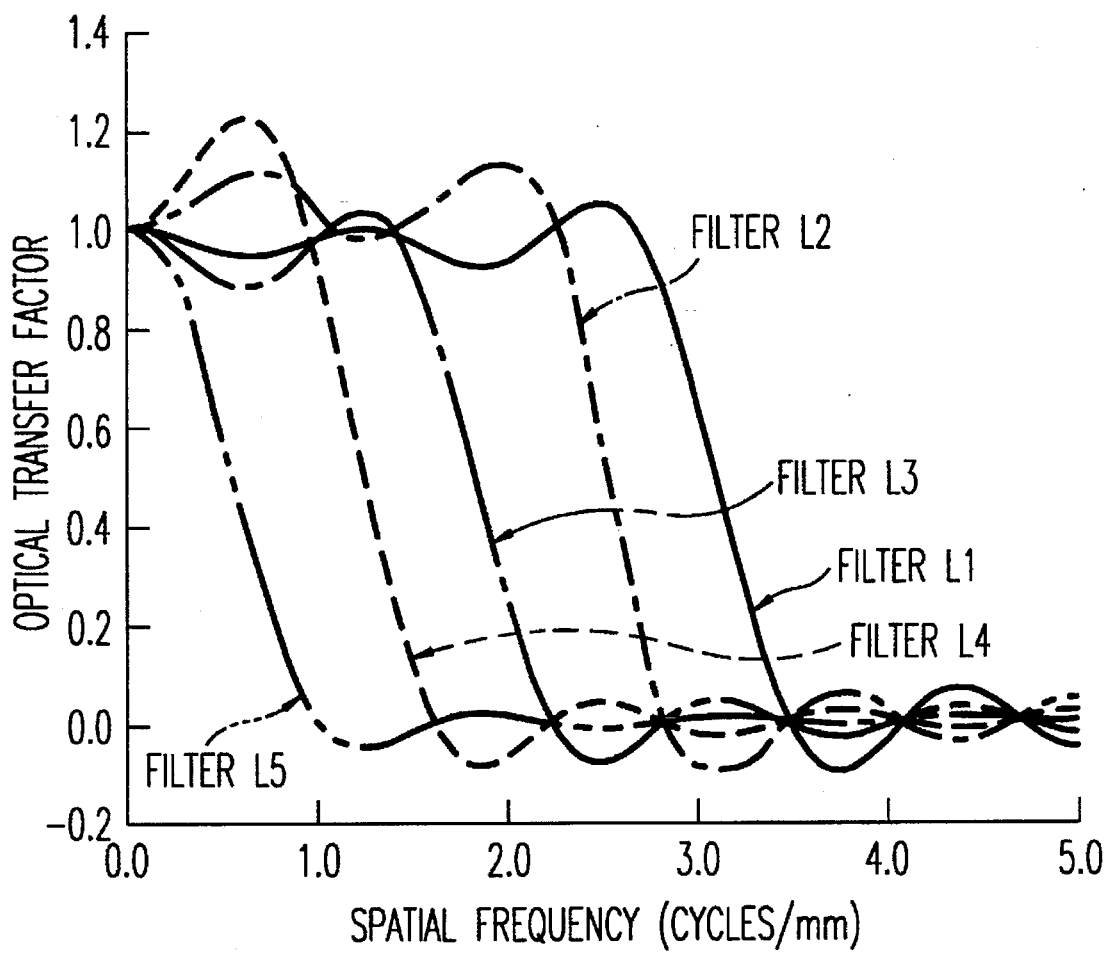
FIGS. 12(a), 12(b) and 12(c) are graphs of filter characteristics employed in the multiple difference imaging technique of the present invention.
Figure 12B:
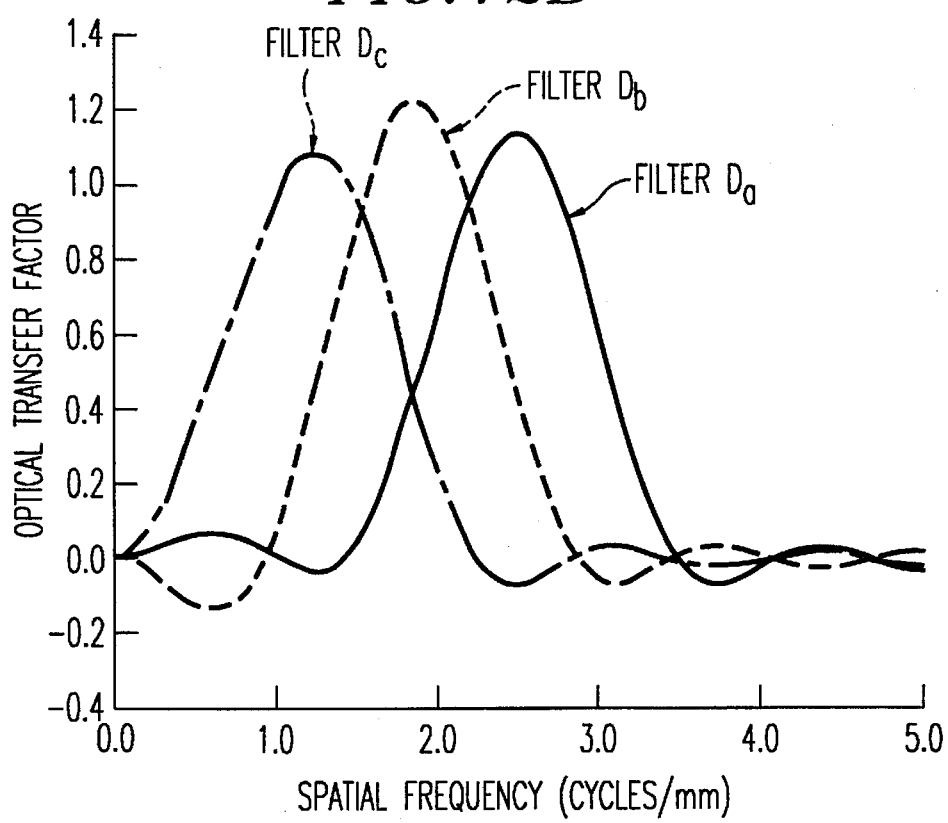
Figure 12C:
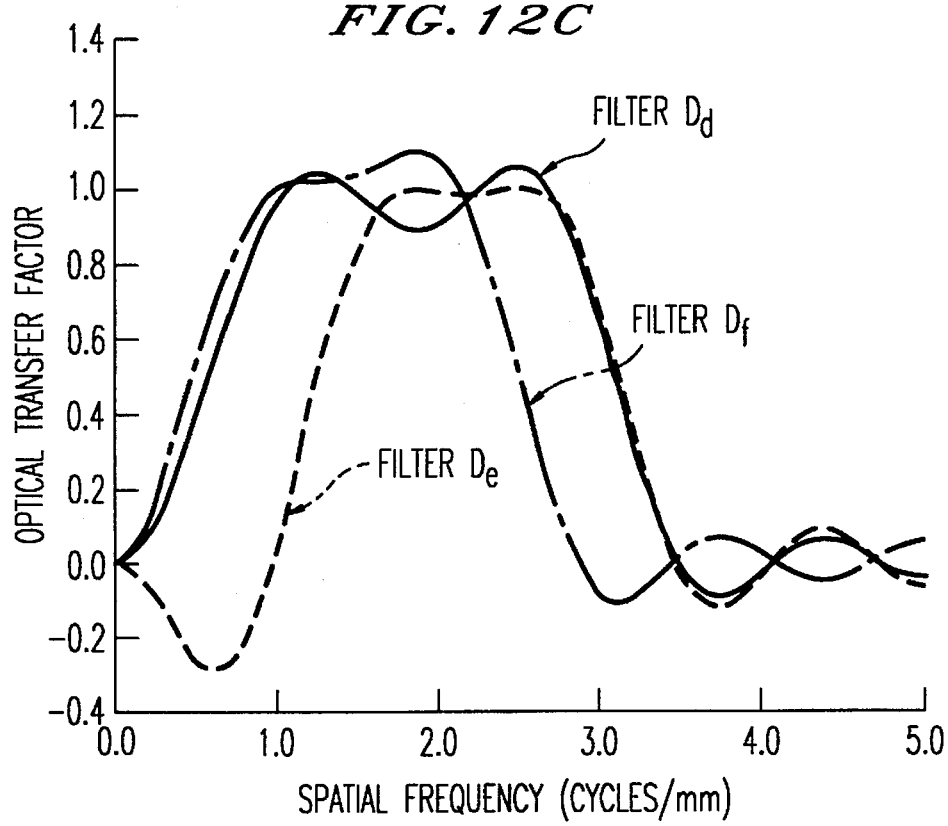
Figure 13A:
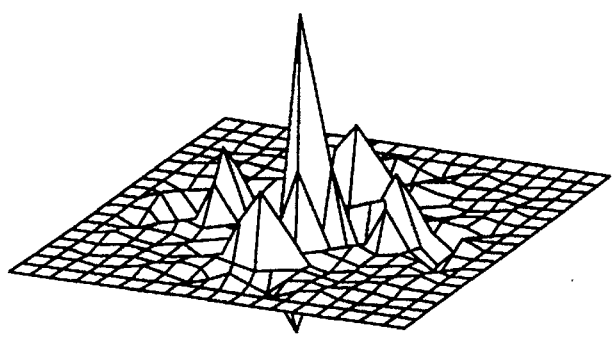
FIGS. 13(a), 13(b), 13(c), 13(d), 13(e) and 13(f) are illustrations of the shapes of the filter in the spatial domain for the filters used in the multiple difference imaging techniques of the present invention.
Figure 13B:
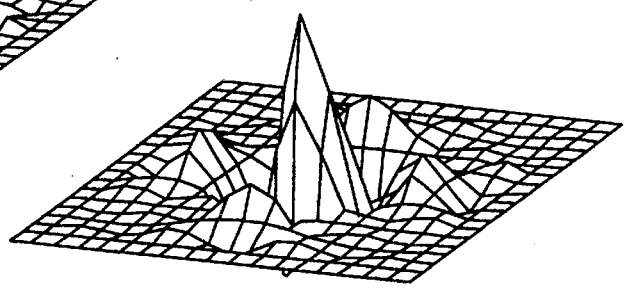
Figure 13C:
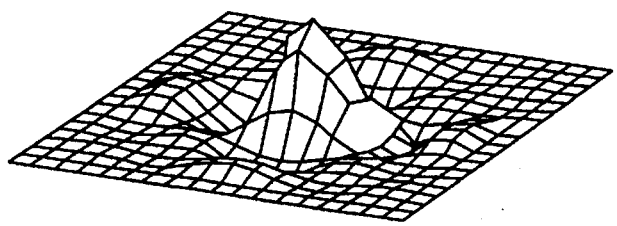
Figure 13D:
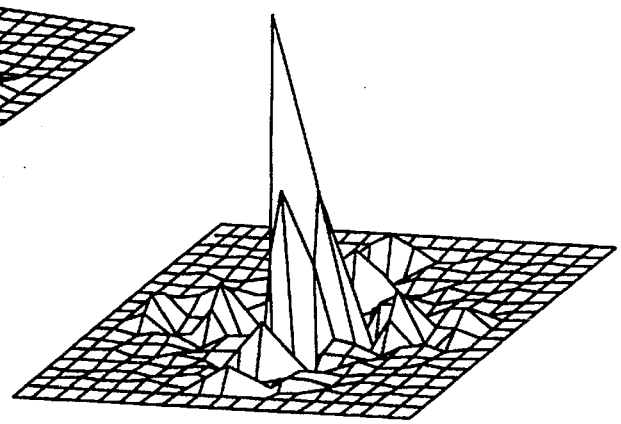
Figure 13E:
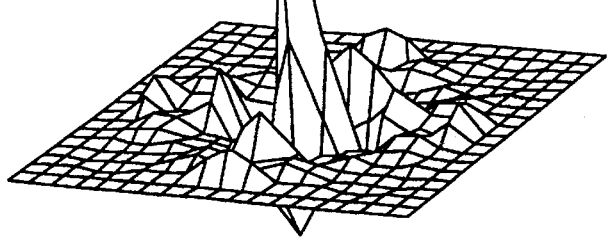
Figure 13F:
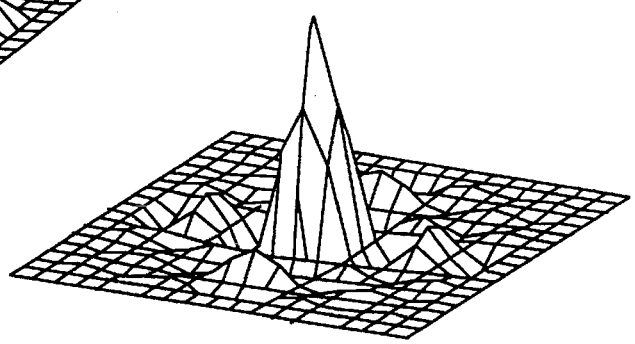

Spatial filters were designed to enhance or to suppress microcalcifications. FIG. 12(a) shows the frequency characteristics of five filters, L1, L2, L3, L4 and L5, designed in this study. The linear filters were designed based on rectangular functions in the frequency domain; however, images were processed by the convolution in the spatial domain. Since the rectangular function in the frequency domain is derived from the Fourier transform of a sine function in the spatial domain, a sinc function is sampled with different sampling distances to form the filters. In actual filtering, signal-enhancement filter and signal-suppression filters were combined into one filter that can directly produce difference images from original digitized mammograms, for a shorter computation time. Six pairs of filters were selected to form combined filters. Filters $D_a$, $D_b$, $D_c$, $D_d$, $D_e$ and $D_f$ were derived from combinations of L1 and L3, L2 and L4, L3 and L5, L1 and L5, L2 and L5, L1 and L4, respectively. FIGS. 12(b) and 12(c) illustrate the frequency characteristics of the combined filters. For all of the combined filters, 15×15 kernels were used to convolve image pixel values in the spatial domain. The shapes of the filters in the spatial domain are shown in FIGS. 13(a)–13(f).

For each of the "true" microcalcifications, three features were determined, namely, area, contrast and effective volume, in order to examine whether a difference image created by one filter provides signal candidates of microcalcifications that are different from those created by another filter. Non-uniform background trend was corrected in 99×99 region of interest (ROI) centered on a microcalcification. Pixel values in the ROI were thresholded at the level of one half of the local maximum pixel value. The area of the microcalcification was measured as the number of the pixels above the threshold level in the area including the local maximum pixel. Contrast of the microcalcification was defined as the difference between the average pixel value in the area of the microcalcification and the background. Volume of microcalcification was defined as the product of the area and the thickness of the microcalcification. Thickness of the microcalcification was determined by correcting the measured contrast in optical density by using the characteristic curve of the screen-film system that was employed to produce the mammograms used in this study.

Figure 14:
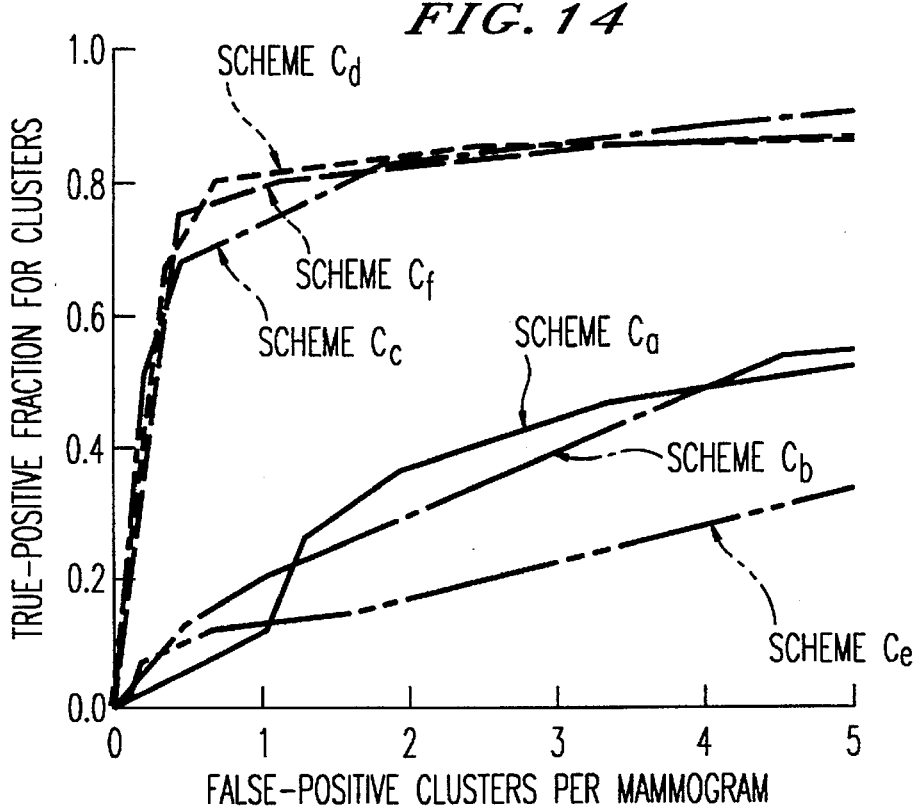
FIG. 14 is a graph illustrating free response receiver operating characteristics (FROC) curves in the detection of clusters using the method illustrated in FIG. 11(a), in which the filters $D_a$, $D_b$, $D_c$, $D_d$, $D_e$, or $D_f$ were used.

FIG. 14 illustrates Free Response Receiver Operating Characteristic (FROC) curves in the detection of clusters in 39 mammograms using six C schemes, in each of which one of the filters $D_a$, $D_b$, $D_c$, $D_d$, $D_e$ or $D_f$ was used. The C scheme using filter $D_a$ is denoted as scheme $C_a$ and other five schemes are denoted in the same manner. Schemes $C_c$, $C_d$ and $C_f$ provided performances similar to each other. Scheme $C_c$ reached the highest sensitivity (93%) while the average false-positive clusters per mammogram was 6.3. On the other hand, the performances of schemes $C_a$, $C_b$ and $C_e$ demonstrated low sensitivity.

Figure 15A:
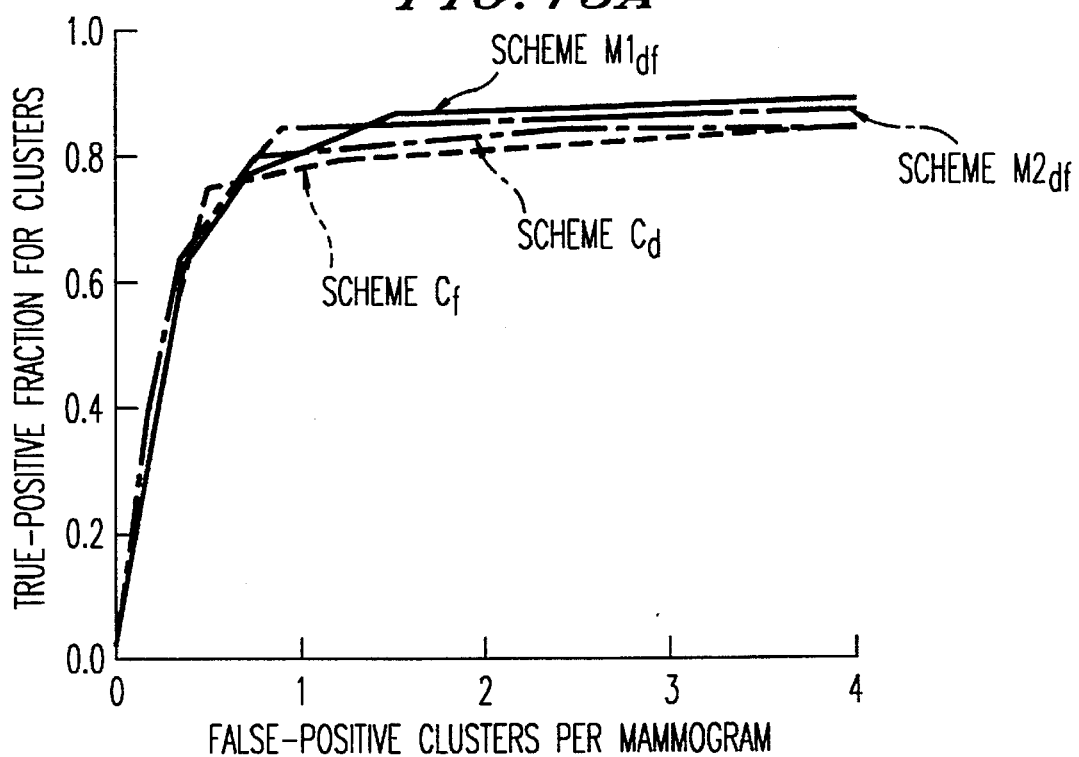
FIGS. 15(a), 15(b) and 15(c) are graphs illustrating FROC curves illustrating the relative performance of the processing technique shown in FIGS. 11(a), 11(b) and 11(c) employing different filtering schemes.
Figure 15B:
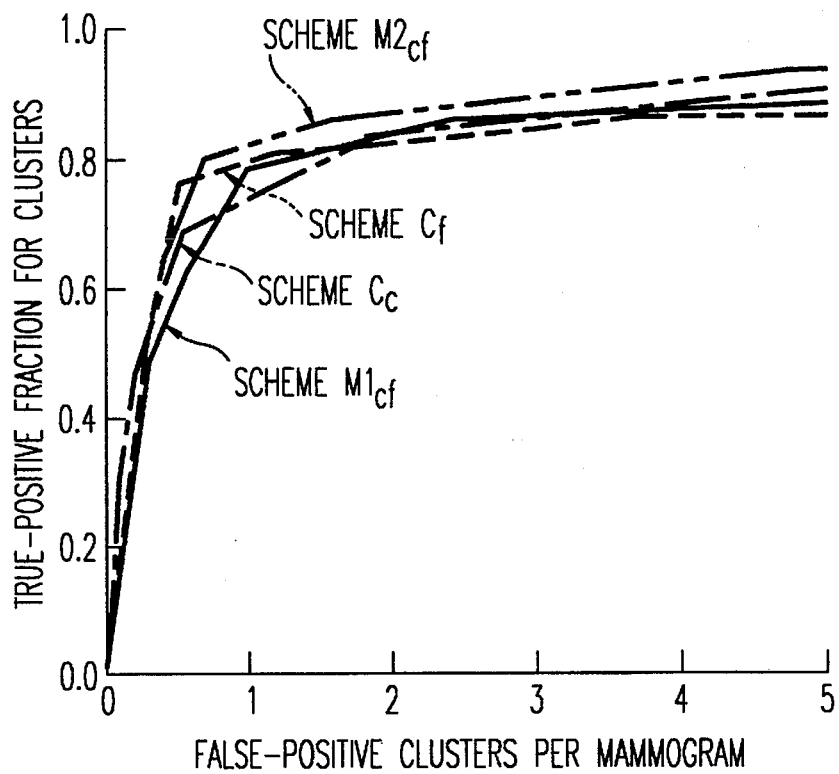
Figure 15C:
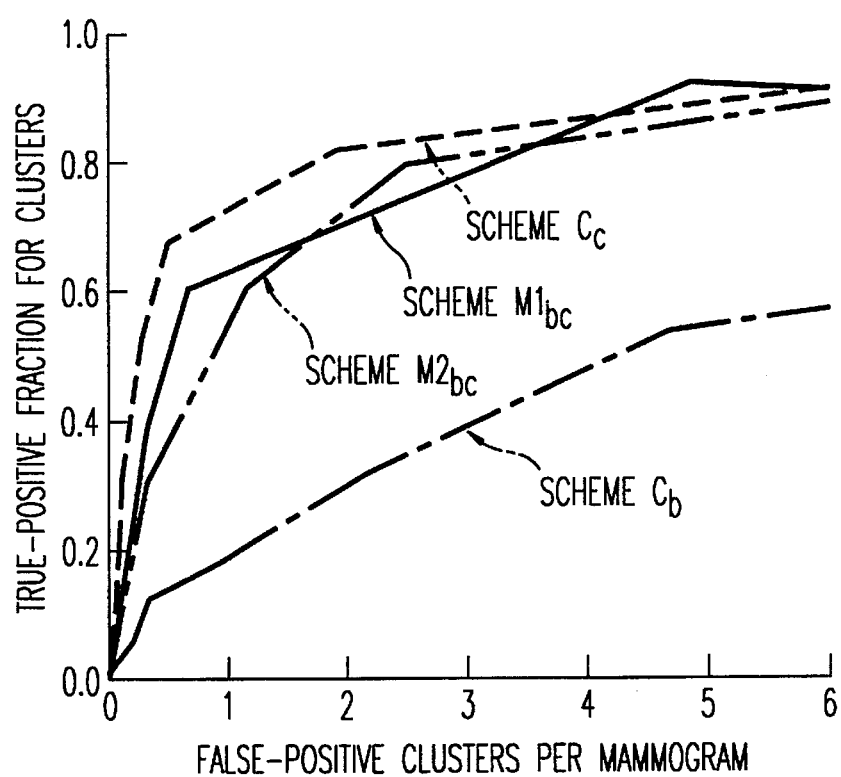

Three combinations of filters, which consist of filters $D_d$ and $D_f$, filters $D_c$ and $D_f$, and filters $D_b$ and $D_c$, were used to examine M1 and M2 schemes. The M1 scheme using filters $D_d$ and $D_f$ is called scheme M1$_{df}$ and other M1 and M2 schemes are also denoted in this manner. FIGS. 15(a), (b) and (c) illustrate FROC curves of the M1 and M2 schemes and type C schemes that use either one of two filters used in M1 or M2 scheme for comparison. Scheme M1$_{df}$ provided higher sensitivities than schemes $C_d$ or $C_f$ at 1.5 or greater false-positive detection rate. Scheme M2$_{df}$ also indicated higher sensitivities than these current schemes at 0.9 or greater false-positive detection rate. The sensitivities and the numbers of false-positive clusters per mammogram at 3.6 and 3.8 of LTF were 90% and 4.0, and 88% and 1.5, respectively, for scheme M1$_{df}$, 88% and 3.0, and 85% and 0.9, respectively, for scheme M2$_{df}$, 85% and 2.4, and 80% and 0.7, level respectively, for scheme $C_d$, and 80% and 1.2, and 76% and 0.5, respectively, for scheme $C_f$. As shown in FIG. 15(b), for combination of filter $D_c$ and filter $D_f$, scheme M2$_{cf}$ indicated a slight improvement in the sensitivity, whereas scheme M1$_{cf}$ did not improve the sensitivity. For the combination of filter $D_b$ and $D_c$, the sensitivity of scheme M1$_{bc}$ is the highest at about five false-positive clusters per mammogram as illustrated in FIG. 15(c). However, this improvement may not be significant. In the range from zero to four false-positive clusters per mammogram, one of the current schemes, scheme $C_c$ indicated the best performance in the four schemes.

The improvement of the performances by using schemes M1$_{df}$, M2$_{df}$ and M2$_{cf}$ occurred at 3.6 or 3.8 of LTF. Table IV shows the result of the detection of the clusters in 39 mammograms at (LTF) of 3.6 for schemes $C_d$, $C_f$, M1$_{df}$ and M2$_{df}$.

TABLE IV

| Cluster number | Detection in scheme $C_d$ | Detection in scheme $C_f$ | Detection in scheme M1$_{df}$ | Detection in scheme M2$_{df}$ |
| --- | --- | --- | --- | --- |
| 1 | | | | |
| 2 | | | | |
| 3 | Missed | Missed | Missed | Missed |
| 4 | | | | |
| 5 | | Missed | | |
| 6 | | | | |
| 7 | | | | |
| 8 | | | | |
| 9 | | | | |
| 10 | | | | |
| 11 | | | | |
| 12 | Missed | | | |
| 13 | | | | |
| 14 | | | | |
| 15 | | | | |
| 16 | | | | |
| 17 | | | | |
| 18 | | | | |
| 19 | | | | |
| 20 | | | | |
| 21 | | | | |
| 22 | | | | |
| 23 | Missed | Missed | Missed | Missed |
| 24 | Missed | Missed | Missed | Missed |
| 25 | | | | |
| 26 | | Missed | | |
| 27 | Missed | Missed | | Missed |

TABLE IV-continued

| Cluster number | Detection in scheme $C_d$ | Detection in scheme $C_f$ | Detection in scheme $M1_{df}$ | Detection in scheme $M2_{df}$ |
|---|---|---|---|---|
| 28 | | | | |
| 29 | | | | |
| 30 | | Missed | | |
| 31 | | | | |
| 32 | | | | |
| 33 | | | | |
| 34 | | | | |
| 35 | | | | |
| 36 | | | | |
| 37 | | | | |
| 38 | | | | |
| 39 | | | | |
| 40 | Missed | Missed | Missed | Missed |
| 41 | | | | |
| Total number of detected clusters | 35 | 33 | 37 | 39 |

Since some clusters detected in scheme $C_d$ were different from those detected in scheme $C_f$, scheme $M2_{df}$ detected more true-positive clusters than either one of schemes $C_d$ and $C_f$. Scheme $C_d$ and $C_f$ detected 94 and 46 false-positive clusters, respectively, in 39 mammograms at 3.6 of LTF. Twenty-four clusters were identified as the same in these 94 and 46 clusters. The ratio of overlapped false-positive clusters is 50% or less, although that of overlapped true-positive clusters is approximately 90%. In addition, scheme $M1_{df}$ detected a cluster (cluster 27 in Table V) that were missed in those two current schemes. For this cluster, true-positive microcalcification signals before clustering operation are shown in Table V.

TABLE V

| Microcalcification number in the cluster | Detection in scheme $C_d$ | Detection in scheme $C_f$ | Detection in scheme $M1_{df}$ |
|---|---|---|---|
| 1 | | detected | detected |
| 2 | detected | | detected |
| 3 | | | |
| 4 | | | |
| 5 | | | |
| 6 | | | |
| 7 | detected | detected | detected |
| Total number of detected microcalcifications | 2 | 2 | 3 |

Figure 16:
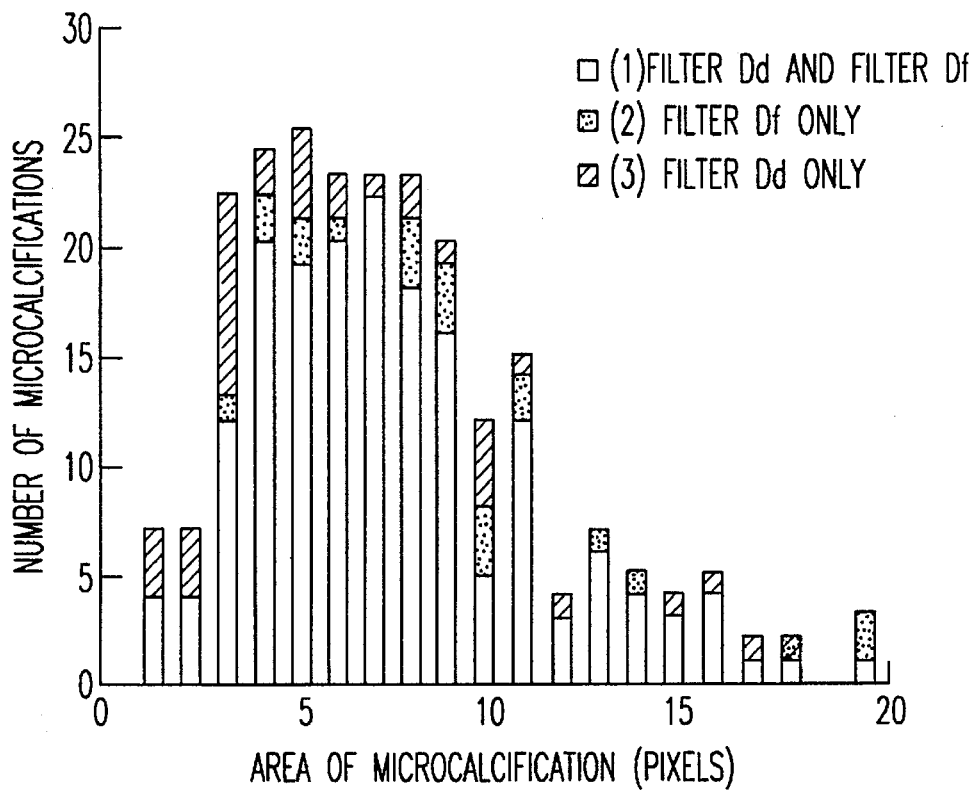
FIGS. 16 and 17 are histograms of areas and volumes, respectively, or three groups of "true" microcalcification signals obtained with filters $D_d$ and $D_f$, $D_f$ only, and $D_d$ only.
Figure 17:
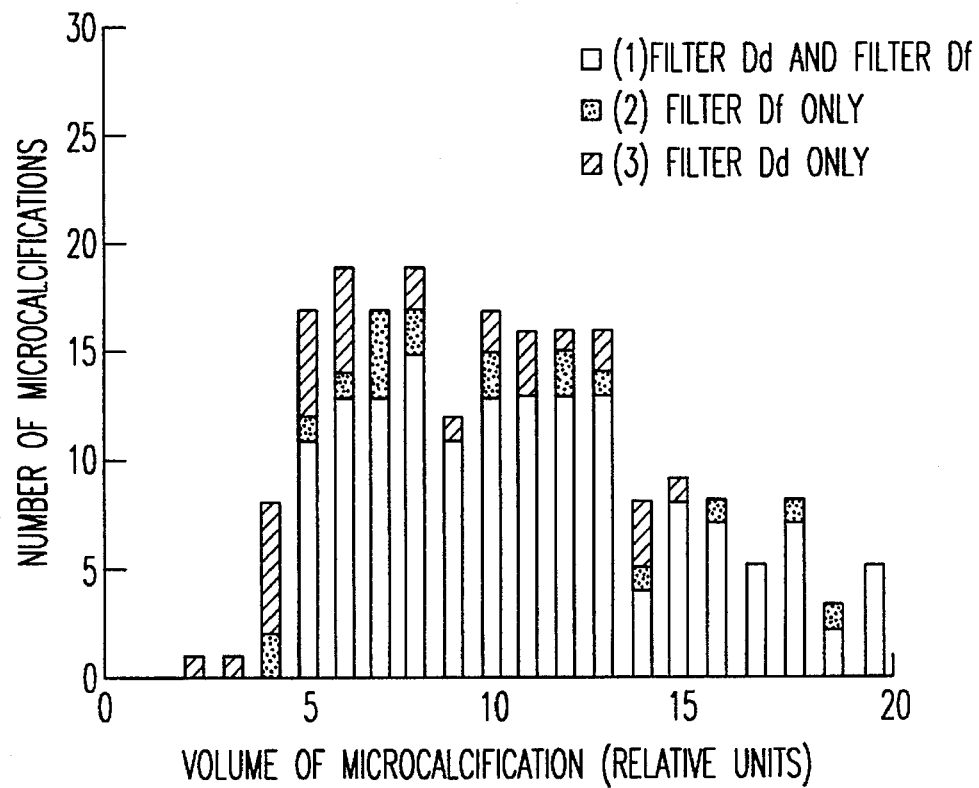

In either one of two current schemes, only two true-positive signals were detected, and one of these two signals was different in the two current schemes. However, three true-positive signals were detected and regarded as a cluster in clustering operation in scheme $M1_{df}$. This indicates that the two filters ($D_d$ and $D_f$) enhanced different microcalcifications in separate difference images. To understand this phenomena further, the histograms of areas and volumes for three groups of "true" microcalcification signals were examined, namely, (1) true-positive signals commonly detected with filters $D_d$ and $D_f$, (2) true-positive signals detected with filter $D_f$ alone, (3) true-positive signals detected with filter $D_d$ alone. As shown in FIGS. 16 and 17, it appears that smaller microcalcifications in area or volume were detected in difference images that were created with filter $D_f$ than with filter $D_d$.

As discerned from FIGS. 15(a), 15(b) and 15(c), all of M1 and M2 schemes did not improve the sensitivity. Filters that provided similar performances in C schemes improved the sensitivity in M1 and M2 schemes. In contrast, filters that provided different performances did not improve the performance when the two filters are combined. The detection rate of individual microcalcifications from the difference images created with filter $D_a$, $D_b$ or $D_e$ were also much lower than that from those images created with filter $D_c$, $D_d$ or $D_f$ at a certain level of local thresholding. As shown in FIG. 14, it is visually clear that filters $D_a$, $D_b$ or $D_e$ do not clearly enhance microcalcifications. This indicates that an appropriate linear filter for creating difference images should have large optical transfer factors in the frequency range between 1.0 and 1.5 cycles/mm. This range of the frequency corresponds to possible major frequency components of "true" microcalcifications included in 39 mammograms, because the average diameter of the microcalcifications is 0.31 mm. FROC curves indicate that filters to be used in their combination must be sensitive to most microcalcifications, but their sensitivities must be slightly different for different size microcalcifications. If such a condition is satisfied, many of clusters would be commonly detected by two current schemes but some clusters would be detected only by one of the schemes. For example, if 10% of clusters detected in two current schemes are different at a performance level, and if the performance of the current schemes is 80% with 2.5 false-positive clusters per mammogram, scheme M2 will provide a performance level of 88% sensitivity with 2.75 false-positive clusters per mammogram. This level can be higher than another performance level of the scheme of FIG. 11(a). Since the ratio of overlap of false-positive clusters from two schemes was smaller than that of true-positive clusters, the average number of false-positive clusters per mammogram was greater than expected. It is more difficult to estimate a performance of the M1 scheme than that of the M2 scheme because the "OR" operation is performed on locations of candidates of microcalcification signals instead of those of clusters in the scheme M1 and clustering affects non-linearly the identification of clusters. However, FIGS. 16 and 17 indicate that a condition similar to that mentioned above for clusters is satisfied for microcalcification signals. The scheme $M1_{df}$ provided 90% sensitivity and approximately 4.0 false-positive clusters per mammogram at the same local threshold level. Scheme $M1_{df}$ detected greater numbers of true-positive and false-positive clusters than scheme $M2_{df}$. However, if more false-positive microcalcification signals are eliminated, scheme $M1_{df}$ might provide a better performance. Another advantage of scheme M1 is that the scheme can improve further the sensitivity. As shown in Tables IV and V, it is possible that scheme M1 detects a cluster that is missed in two current schemes with different filters. Tables IV and V also clearly indicate that the two filters $D_d$ and $D_f$ can enhance microcalcifications with different sizes.

It is likely that the multiple difference image technique tends to increase false-positive detection rate whereas the sensitivity is expected to be improved. However, the edge-gradient and linearity thresholding eliminating false positives while maintaining most of true positives as above discussed are useful and to be applied in connection with the multiple difference image technique. Therefore, if the multiple-difference image technique is used together with these methods for eliminating false positives, the performance of our CAD scheme is improved.

The multiple-difference image technique allows us to employ two or more difference images prior to the local thresholding. However, it requires at least two-times the computation time compared with single difference image technique, which is a disadvantage of this technique. However, this method enables one to apply any kind of filters such as linear filters and morphological filters to create signal-enhanced and signal-suppressed images. For example, two different linear filters and two different morphological filters can be used to create difference image Da and difference image Db, respectively. That will provide flexibility in CAD schemes.

Thus, the multiple-difference image technique investigated in the second study increases the CAD sensitivity scheme for detection of clustered microcalcifications in mammograms, if filters are chosen to have large optical transfer factors in the range between 1.0 and 1.5 cycles/mm, so that processing is focused on microcalcifications having an average diameter of 0.31 mm.

In a further study performed by the inventors, a new noise reduction filter that eliminates high frequency noise without corrupting structures of clinical interest was developed. The filter combines the results of morphological erosion and dilation operators using multiple structuring elements. Under the assumption that any single or pair of connected pixels that are either higher or lower than their surrounding pixels is caused by noise, then compared to median filtering, the noise reduction filter of this invention does not effect small structures while eliminating high frequency noise. Furthermore, it does not reduce the contrast of structures as much as a median filter. The noise reduction filter was applied as a preprocessing technique in an automated scheme for detecting clustered microcalcifications on digital mammograms. Using the noise reduction filter, the performance of the scheme was improved by reducing the false-positive rate by as much as a factor of 3 without compromising the true-positive detection rate.

Morphological operators have been used to filter medical images. (See J. Barba, et al, "Edge detection in cytology using morphological filters," Proc. SPIE 1075, 311–318 (1989); G. T. Bartoo, et al, "Mathematical morphology techniques for image processing applications in biomedical imaging," Proc. SPIE 914, 446–475 (1988); and H. Yoshimura, et al, "Computerized scheme for the detection of pulmonary nodules: Nonlinear filtering technique," Invest. Radiol. 27, (1992)). There are two basic operators: erosion and dilation. For grey scale images, erosion is defined by taking the minimum pixel value within a local neighborhood around the pixel of interest (the operating point). Conversely, dilation is performed by taking the maximum pixel value within a local neighborhood. The local neighborhood is defined by one or more structuring elements. When multiple structuring elements are used, erosion is defined as the maximum of the minima of each of the structuring element. Dilation, then, is the minimum of the maxima.

Figure 18:
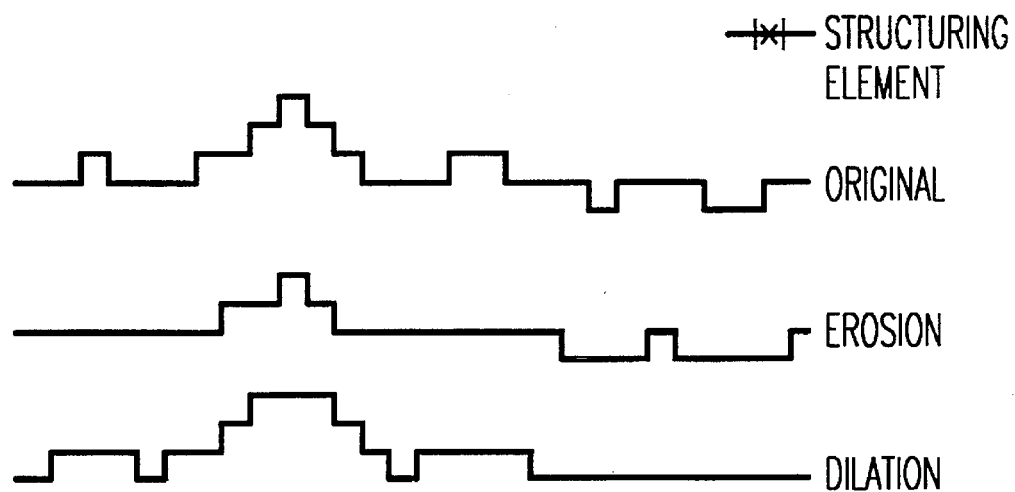
FIGS. 18 and 19 are schematic illustrations illustrating how erosion operators can eliminate "spikes" in an image and dilation operators can fill in "pits"
Figure 19:
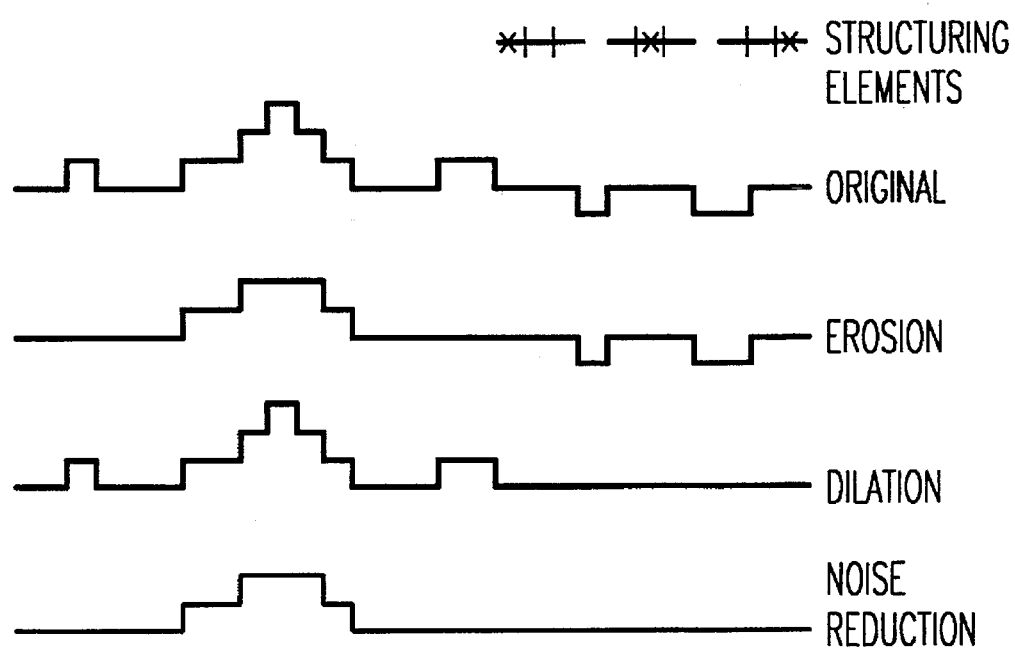

Erosion operators can eliminate "spikes" in an image and dilation operators can fill in "pits", as illustrated in FIGS. 18 and 19. Unavoidably, with a single structuring element, larger structures in the image will be modified. Previous studies above identified have all employed single structuring elements, and therefore, altered the appearance, both shape and contrast, of important structures in the image. With the proper choice of multiple structuring elements, however, it is possible to eliminate high frequency noise, both spikes (using erosion) and pits (using dilation), while preserving larger structures. This is illustrated in FIGS. 18 and 19, where three structuring elements are used. Each structuring element has in common the operating pixel, indicated by the x in FIGS. 18 and 19. As can be seen in FIG. 19, erosion will eliminate "spikes" that are one or two pixels in size without changing any other pixels. Similarly, dilation will eliminate "pits" without changing any other pixels.

Figure 20:
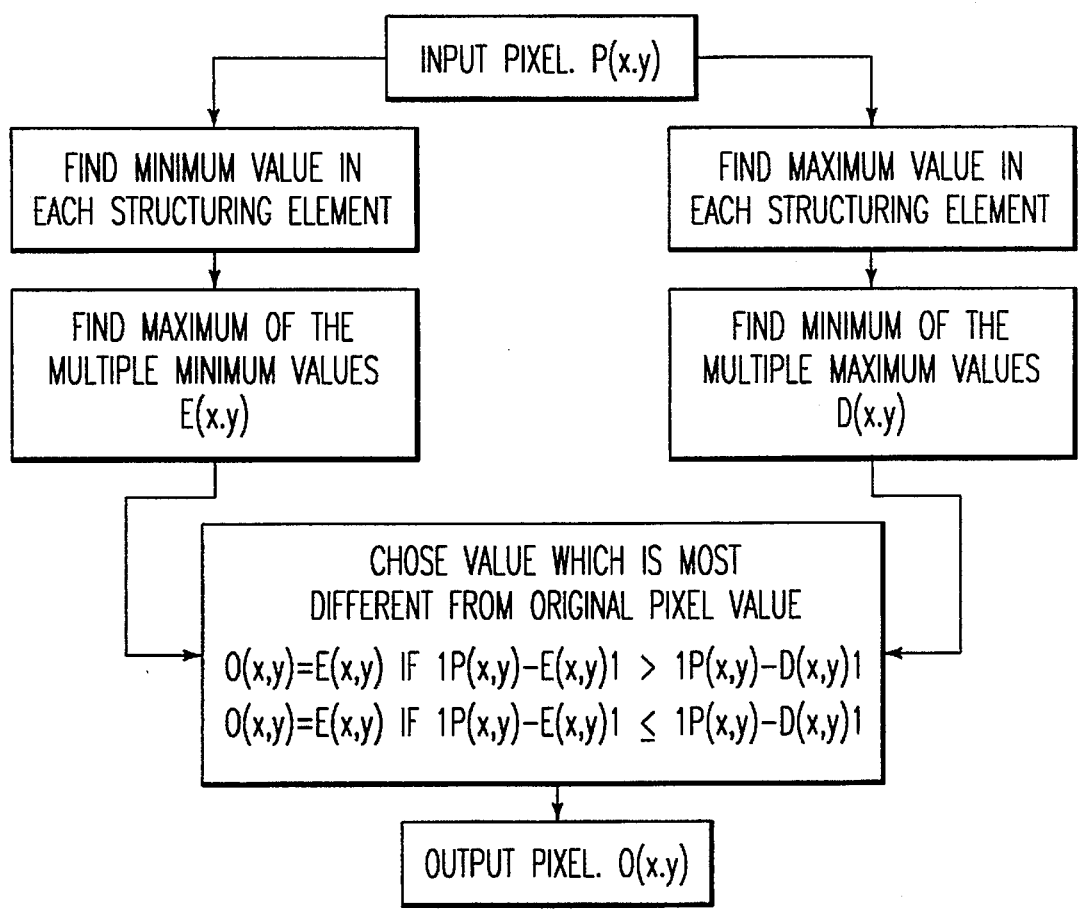
FIG. 20 is a schematic flow chart illustrating preprocessing steps performed on the pixel input digital image data utilizing morphological erosion and dilation operators according to an embodiment of the present invention.

By combining the results of erosion and dilation operations in the appropriate manner, high frequency noise can be preferentially removed from an image. In the present invention, the noise reduction filter uses the result of either erosion or dilation operators using multiple structuring elements. The result of the operation that produces the largest absolute difference from the original pixel value is used. This is performed by subjecting the digital image to separate morphological erosion and dilation operators using plural structuring elements to produce an eroded image and a dilated image, determining a first absolute difference between the digital image and the eroded image and a second absolute difference between the digital image and the dilated image on a pixel by pixel basis, substituting for values of pixels in the digital image with values of corresponding pixels in the eroded image when the first absolute difference is greater than the second absolute difference on a pixel by pixel basis, and substituting for values of pixels in the digital image with values of corresponding pixels in the dilated image when the second absolute difference is greater than the first absolute difference on a pixel by pixel basis, thereby producing a noise filtered image. A schematic outline of the noise reduction filter is shown in FIG. 20. As illustrated in FIG. 19, the noise filter can remove noise spikes and pits while leaving larger structures unchanged. Note that even spikes or pits that are contained within larger structures will be removed.

Figure 21:
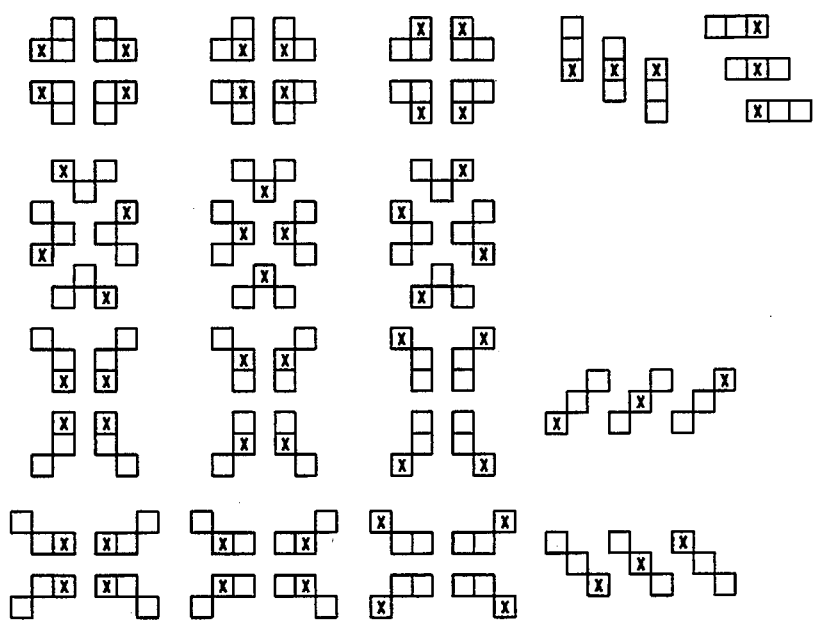
FIG. 21 is an illustration of multiple structural elements used in the morphological erosion and dilation processing of the present invention.

For two-dimensional images, the noise filter produces a similar result as in the one-dimensional case, if the appropriate structuring elements are chosen. What is required is a set of structuring elements that contains all possible combinations of three connected pixels. There are 60 such combinations and they are shown in FIG. 21. The number of required structuring elements can be reduced to 18 if only combinations that have four-point connectivity (as opposed to eight-point connectivity) are used. These 18 structuring elements, which are a subset of the 60 elements, are shown in upper part of FIG. 21. The effect of using the smaller number of structuring elements will be discussed later. Note that only flat structuring elements are used here (i.e., they have a value 1 inside the element and 0 outside). Also, all structuring elements include the operating pixel. With the 60 structuring elements, only structures that 1 or 2 connected pixels that are higher or lower than all their immediate surrounding pixels will be removed. With the 18 structuring elements, all structures 1 or 2 pixels and all structures 3 pixels with at least one diagonal connection (there are 42 such 3-pixel combination and are the ones that are not in common between the 60 and 18 structuring elements sets). Basically for a given structure in the image, if any of the structuring elements fits completely in the structure, then the size and shape of that structure will remain unchanged. More specifically, the value of every pixel in that structure will remain unchanged, unless there is a noise spike or pit on top of the structure.

For reference, the new noise reduction filter was compared to conventional median filtering. The median filter used a kernel consisting of a 3×3 cross. A 3×3 cross was chosen, since a 3×3 box will corrupt the corners of structures.

In the application of the noise reduction filter to digital mammography, it is assumed that any pixel or any pair of connected pixels (pixel size of 0.1 mm) that is higher or lower than its surrounding pixels is caused by random fluctuations in the image. That is, it is not caused by any real structure in the breast. The validity of this assumption is supported by examining radiographs of mammographic phantoms that contain simulated microcalcifications ($Al_2O_3$ specks) of different sizes. It is "difficult" to see 0.24 mm (linear dimension) specks and it is not possible to 0.20 mm specks in conventional mammograms. A 0.2 mm speck would appear ideally as a 2×2 pixel area in one of the digitized images being processed.

To illustrate the potential of the noise reduction filter, one image was chosen from a database of 110 digitized mammograms, which contain clustered microcalcifications. The mammogram was digitized using a sampling distance and a sampling aperture of 0.1 mm with 10-bit grey-scale resolution. The original digitized image contains two clusters of microcalcifications.

The potential of the noise reduction filter for improving the performance of the inventors' automated scheme for the detection of clustered microcalcification was investigated. The basic scheme is shown schematically in FIG. 22(a) and has been described elsewhere. (See R. M. Nishikawa, et al, "Computer-aided detection of clustered microcalcifications: An improved method for grouping detected signals," Med. Phys. (1993)). The most straight forward application of the noise reduction filter is as a preprocessing step to eliminate high frequency noise as shown in FIG. 22(b), in comparison to the basic scheme of FIG. 22(a).

FIGS. 23(a) and 23(b) compare the actually pixel values for two areas centered on microcalcifications for the noise reduction filter of the present invention and conventional median filtering. The pixels belonging to the microcalcifications are outlined in black. The shaded areas indicate pixels whose values have changed after filtering. Most of the pixels remain unchanged after filtration using the noise reduction filter with 60 structuring elements, whereas most pixels are changed upon using a median filter. In fact for the particular microcalcification shown in FIG. 23(b), three pixels at the periphery have been set to values comparable to the background pixels after median filtering. Thus, the median filter has changed the shape of the microcalcification. This does not occur with the noise reduction filter. Furthermore, the median filter reduces the contrast of the microcalcification to a greater extent than does the noise reduction filter. After median filtering the contrast of the microcalcification is reduced by 20–39%, while after the noise reduction filter the contrast is decreased by only 6–22%.

The median filter is actually more effective at reducing the standard deviation in pixel values in the background. In terms of reducing the "noise" in the background of the microcalcification, this is a desirable feature. However, the smoothing of the background may in fact be corrupting actual breast structure. If the goal is to reduce noise to enhance actual breast structure, and not just the microcalcification, then the noise reduction filter has more desirable properties than the median filter.

Figure 22B:
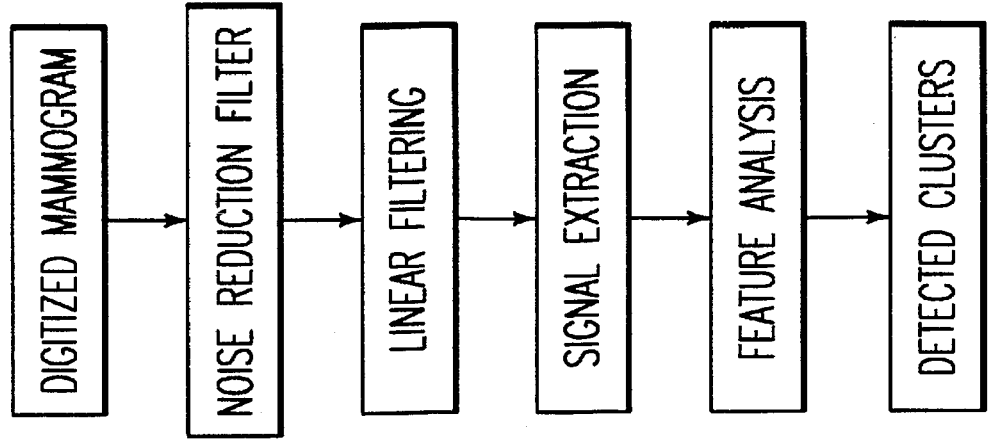
FIGS. 22(a) and 22(b) are schematic flow charts illustrating processing without and with the noise reduction filter shown in FIG. 20, respectively.
Figure 22A:
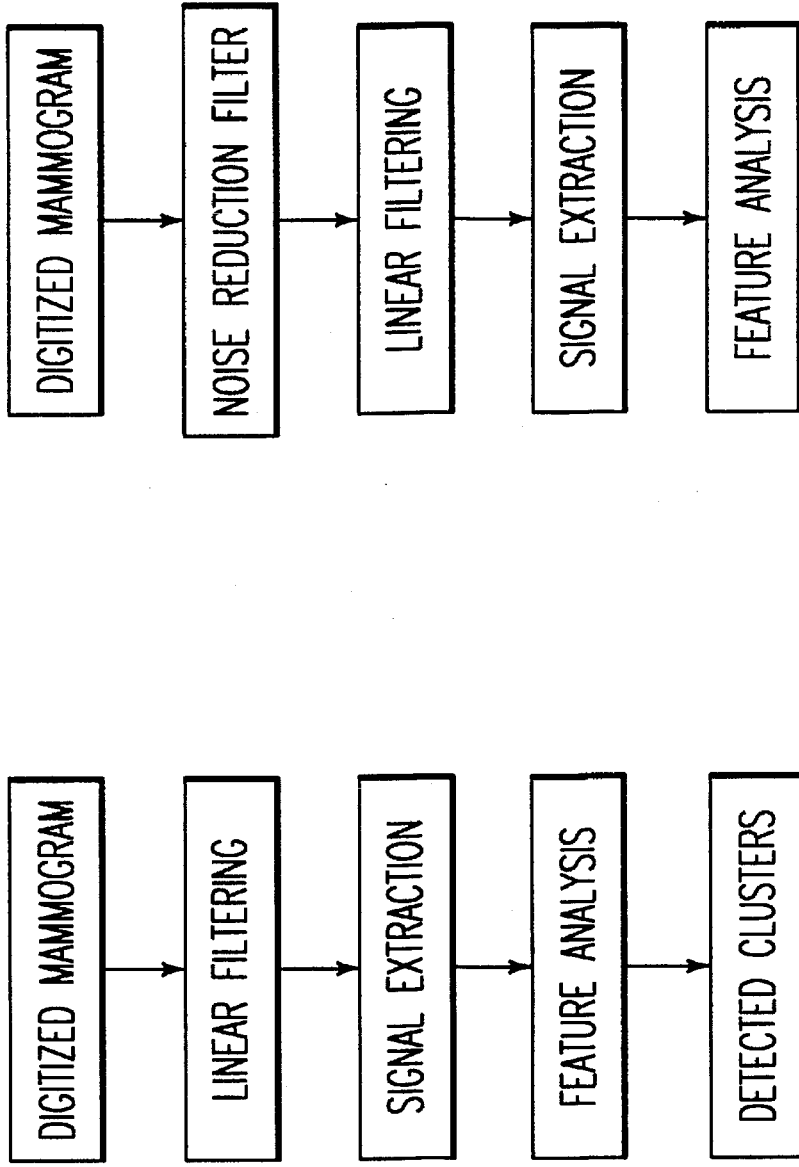
Figure 24:
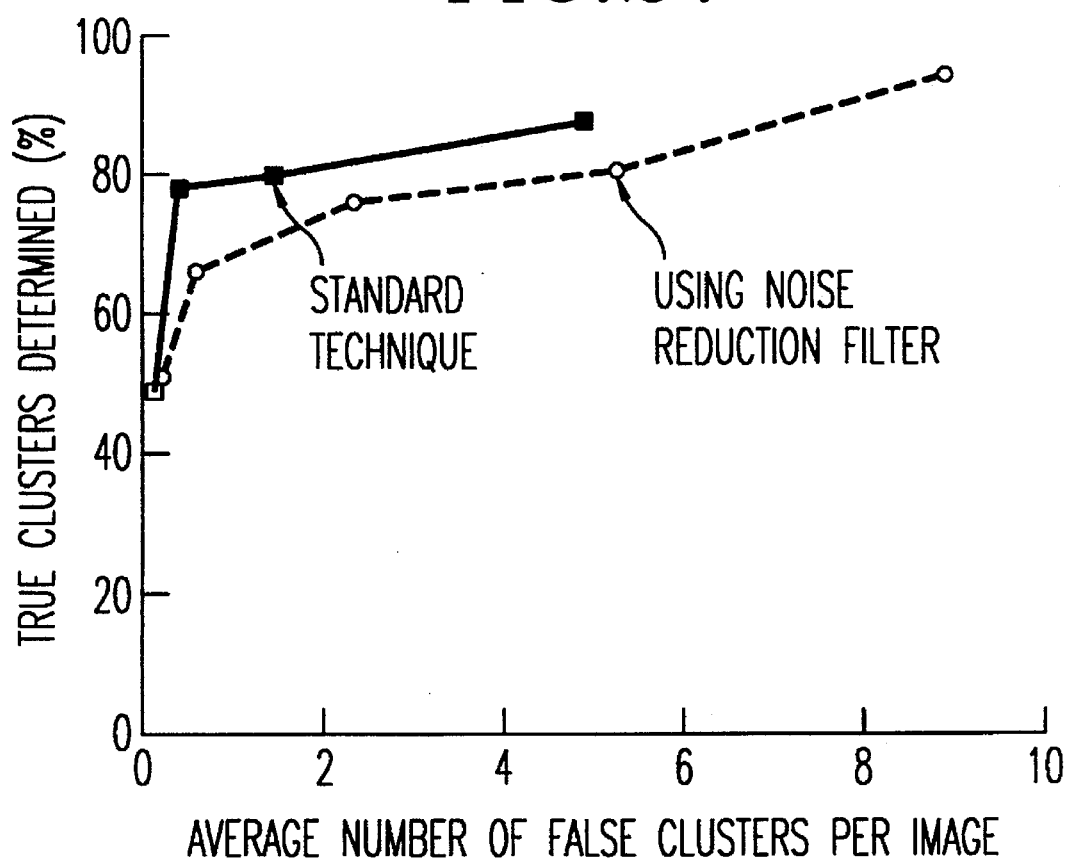
FIG. 24 is a graph of a FROC curve illustrating the effect of the noise reduction filter of the present invention.

FIG. 24 compares the performance of the microcalcification detection scheme of FIG. 22(b) with the noise reduction filter to the basic scheme of FIG. 22(a). Surprisingly, the modified scheme using the noise reduction, filter performs worse than the basic scheme (no noise reduction filter). However, the modified technique reaches a higher sensitivity than does the standard technique, although at a high false-positive rate. Though not seen in FIG. 24, the false positives detected by the standard and modified techniques differ quite substantially. Because the true positives overlap significantly, but the false positives do not, it is beneficial to combine the results of the two methods.

Figure 25:
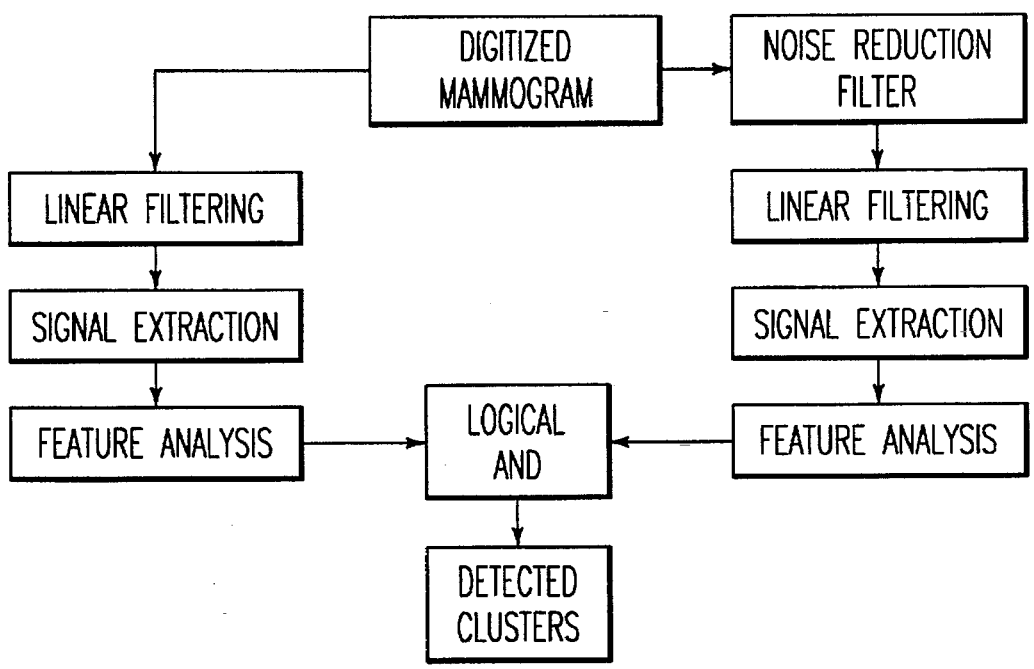
FIG. 25 is a schematic flow chart of processing steps performed according to an embodiment of the present invention in which the noise reduction filter of the present invention is employed to improve sensitivity of true microcalcification cluster detection.
Figure 26:
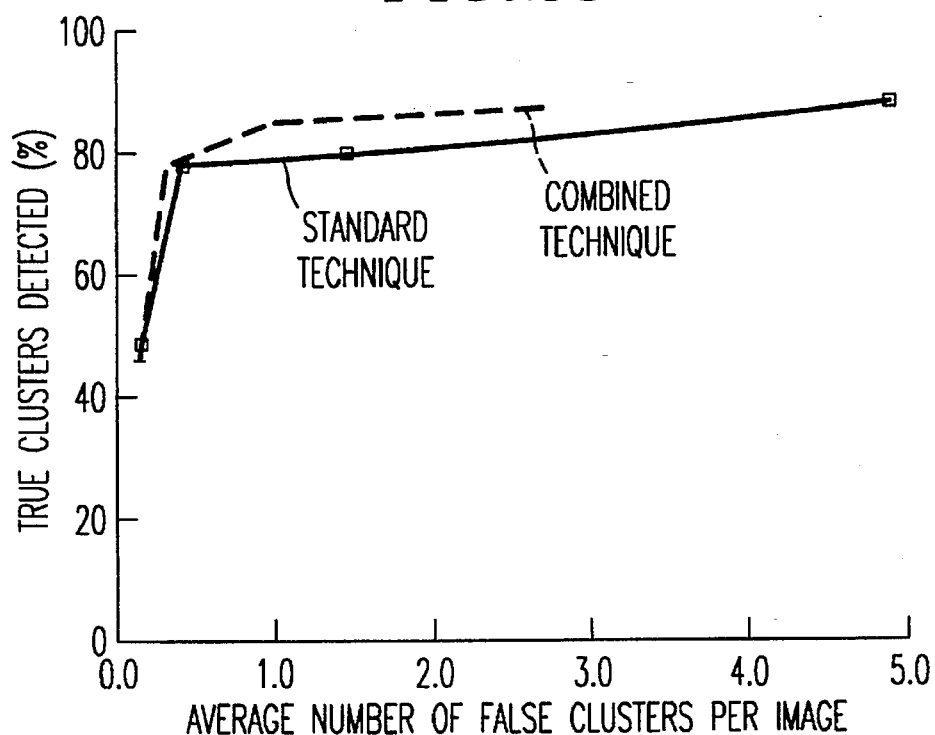
FIG. 26 is a FROC curve illustrating performance of the method of FIG. 25.

FIG. 25 is a schematic flow chart of an embodiment of the invention combining the two methods by means of a logical AND function. That is, if a cluster is detected by both methods, then it is kept, otherwise the cluster is discarded. Using this combined method the performance of the scheme is improved over using the standard technique, as is evident from the FROC curve shown in FIG. 26.

Thus, the third study performed by the inventors indicates that the above described noise reduction filter is capable of removing high frequency noise without corrupting structures of interest. Other types of noise reduction filters, such as median filters, are also effective in removing noise, but they cause some image distortion or degradation. By selecting multiple structuring elements, the disclosed noise filter is guaranteed to leave structures of interest intact. Basically, if any of the structuring elements can "fit" completely within a structure, then that structure is preserved.

It is possible to generate other sets of structuring elements to eliminate larger size noise spikes and pits. In theory, if the size of the smallest structure of interest is known, then a set of structuring elements can be selected to eliminate all smaller structures, under the assumption that smaller structures are noise. Practically, however, the number of structuring elements needed to eliminate noise more than a few pixels in size becomes very large. Table VI summarizes the number of structuring elements for different size (number of pixels) composing one element. Computation time becomes prohibitive quickly as the size of the structuring element increases. It may be possible, however, to implement a subset of the require number in a clever way so that a reasonable number of structuring elements can simulate the total number required.

TABLE VI

| Number of Pixels per Element | Number of Structuring Elements | |
|---|---|---|
| | 4-Point Connectivity | 8-Point Connectivity |
| 2 | 4 | 8 |
| 3 | 18 | 60 |
| 4 | 76 | 440 |
| 5 | 315 | 3190 |
| 6 | 1296 | 22992 |

The difference between using the two sets containing 18 and 60 structuring elements is small. This is because the single pixels that are only connected diagonally to other groups of pixels is not common in medical images. That is, the contrast of any real structure that is small enough to appear as a diagonal line, one pixel "wide" is too low to be imaged reliably. Therefore, it will be lost in noise. The set containing 18 structuring elements is thus considered the appropriate set to use since single pixels that are connected only diagonally to a group of pixels is mostly likely caused by random chance (i.e. noise).

The noise reduction filter is useful as a preprocessing technique both for computer and human vision applications. Careful visual comparison of the unfiltered and filtered images gives the impression that the filtered image appears less sharp and slightly contoured. The amount of high frequency information in the digitized mammogram is low due to the modulation transfer function roll off of both the screen-film system and the digitizer. As a result, noise dominates at high frequency. When the high frequency noise is removed by the noise reduction filter, the filtered image appears to have a lower high frequency component, even though high frequency information may be more reliable extracted. This apparent loss of resolution and the grey-level contouring may make the filtered image less acceptable to human observers.

The noise reduction filter is ideally suited for reducing false positive detections and increasing the accuracy of feature-extraction techniques in computer-aided diagnosis. In computer-vision applications, insufficient signal-to-noise ratio, and not insufficient contrast (signal), will be the limiting factor to the accurate extraction of information. In cases where the detective quantum efficiency of the detector used to acquire the image is low at high spatial frequencies that are included in the image, then the information at these high frequencies is severely corrupted by noise. In such situations, the noise can be removed without a loss of information by preferentially removing noise spikes and pits—a situation ideally suited for the noise reduction filter described here.

In this study, using the noise reduction filter actually degraded performance of our microcalcification detection scheme. The different techniques used were developed and optimized for images containing high frequency noise. By removing the high frequency noise, the various techniques may not have been operating with their optimum parameters, as evidenced by the fact that different false positives were found with and without the noise reduction filter. Combining the results from two differently filtered images is an approach that other investigators have found useful—Yoshimura et al for the detection of lung nodules on chest radiographs, and Mascio et al, "Automated analysis of microcalcifications in high-resolution digital mammograms," Proc. SPIE 1895, 472–479 (1993), for detection breast calcifications.

In addition to the morphological erosion and dilation filter above-described, the inventors have determined that preprocessing using a pit-filling filter and a spike-removal filter to remove pit noise and spike noise, respectively, is also effective. Technically, these filters are averaging filters with some conditions, as described below, in relation to a filter kernel centered around an operating point.

FIG. 27(a) illustrates an example of the filter kernel used in pit removal filtering. The filter kernel is shown by hatched pixels and the pixel marked by "+" is the operating point. The filter kernel is passed over the entire area of an image in operation. If the pixel value at an operating point in an input image is smaller than all of the pixel values in the filter kernel, the average pixel value of the pixels in the filter kernel is provided to the pixel in the output image, which corresponds to the operating point in the input image. Otherwise, the pixel value of the operating point in the input image is copied to the pixel in the output image. FIGS. 27(a) and 27(b), show examples of profiles in the input image and the output image in a pit-filling operation. One dimensional profiles are shown for simplicity.

The spike-removal filter also works for spike-like noise patterns in a way similar to the pit-filling filter. If the pixel value at an opening point in the input image is greater than all of the pixel values in the filter kernel, the average value of the pixels in the filter kernel is provided to the pixel in the output image, which corresponds to the operating point in the input image. Otherwise, the pixel value of the operating point in the input image is copied to the pixel in the output image. FIG. 27(d) shows examples of one dimensional profiles in the input image and the output image in a spike-removal operation. One dimensional profiles are again shown for simplicity.

There are two parameters for each of the pit-filling filter and the spike-removal filter. They are (1) the shape of the filter kernel and
(2) the number of operations (the same operation can be applied repeatedly).

FIG. 27(b)shows another example of the filter kernel. Note that filtering with the kernel shown in FIG. 27(a) can remove more noise than that with the filter kernel shown in FIG. 27(b). Filtering may be performed more than once. The greater the number of filtering is applied, the greater the number of removed noise patterns. In addition, a different filter can be used in the second or later time. For example, a pit-filling filter with the kernel shown in FIG. 27(a) may be used at the first time, and a spike-removal filter with the kernel shown in FIG. 27(b)at the second time.

The pit-filling and spike removal filters were applied as a pre-processing to original digitized mammograms prior to creating a difference image in our CAD scheme for detection of clustered microcalcifications. When the wavelet transform technique, discussed hereinafter, was used to create difference images, the results indicated that the CAD scheme with application of the pit-filling and spike removal filters described above provided an improved sensitivity compared with that without the filters.

In a fourth study performed by the inventors, wavelet transform techniques were used in the automated detection of clustered microcalcifications in digital mammograms. In this study, the goal was once again to increase the signal-to-noise ratio of microcalcifications by suppressing the background structure of the breast image in order to increase sensitivity and/or to reduce the false-positive rate. To that end, the wavelet transform was used to decompose the digitized mammogram into the transform space. Then, the digital mammograms were reconstructed from transform coefficients modified at several levels in the transform space. Various types of wavelets were examined, and the Least Asymmetric Daubechies' wavelets were chosen to detect clustered microcalcifications in mammograms. The images reconstructed from several different scales were subjected to the CAD scheme in substitution for the difference image technique above discussed, and their performances were evaluated using the 39 mammograms database above noted. Preliminary results show a sensitivity of approximately 85% with a false-positive rate of 5 clusters per image. Results obtained using the wavelet transform were logically OR'ed with results obtained using the difference image technique to improve sensitivity to as high as 90%, as described in more detail hereinafter.

The wavelet transform is a scale-space feature analysis tool that has been investigated extensively for the last several years. The representation obtained by appropriate wavelets provides a simple hierarchical framework for interpreting the image at different resolutions, namely, the information of an image is characterized by different structures in the image. The framework can separate small objects such as microcalcifications from large objects such as large background structures. The present invention emphasizes preserving image detail during each processing step in order to increase the sensitivity and/or to reduce the high false-positive rate observed with current CAD schemes. To accomplish this, digitized mammograms are decomposed by using the wavelet transform and then reconstructed rom transform coefficients modified at several levels in the transform space, as above indicated. Various types of wavelets are examined, and one family of orthogonal wavelets, known as the Least Asymmetric Daubechies' wavelets, is chosen to detect clustered microcalcifications in mammograms. Also, the images reconstructed from several different scales are examined, and their performances are compared using free-response receiver operating characteristic (FROC) curves.

Next provided is an overview of the wavelet theory to assist in understanding some of the basic concepts involved in the wavelet transform. Then, the use of wavelet as a preprocessing step for the automated detection of clustered microcalcification is described. The mathematical discussions concerning the wavelet transform are presented concisely without rigorous mathematical derivations and proofs.

Overview of the Wavelet Transform

The wavelet transform is a tool that decomposes profiles or images into different frequency components, and then each component can be studied with a resolution matched to its scale. The wavelet transform is in some way similar to the Fourier transform. For a given profile $f(x)$ with a continuous variable x, the profile can be expanded in terms of orthonormal basis functions. For the Fourier transform, the basis functions are sine and cosine functions at different frequencies, thus yielding a representation of the frequency content of $f(x)$. These basis functions have infinite lengths ranging from negative infinity to positive infinity. Therefore, information concerning a localized high-frequency signal such as microcalcifications cannot be extracted easily from the resulting Fourier spectrum.

In many applications, however, the frequency content of the original signal localized in space is of interest. The major advantage of using the wavelet transform is that it provides a tool for space-frequency localization. With this feature, the wavelet transform is much more efficient in characterizing abrupt changes such as microcalcifications than the Fourier transform. Another advantage of the wavelet transform is that it provides a hierarchical representation of an image called multiresolution analysis. The scale of the multiresolution basis varies logarithmically rather than linearly. It is important to note that human sensory systems, including the visual system, process information in the same logarithmic manner. These advantages along with some examples using mammograms are described in detail in the following.

The Wavelet transform

The mother wavelet

The wavelet transform of a profile, e.g., the variation of pixel values with position, depends on two variables: scale (or frequency) and space (or location). In the wavelet transform, therefore, all of the basis functions are derived from scaling and translation of a single function. This function, often denoted by $\psi$, is usually called the mother wavelet (or analyzing function). There exist many types of mother wavelets that, by definition, must satisfy a certain mathematical constraint called the admissibility condition. Namely, a mother wavelet must satisfy the following three conditions; (1) it must be oscillatory (wave-like); (2) amplitudes decrease quickly to zero in both the positive and negative directions; and (3) there is no zero-frequency component ($\int \psi(x)dx=0$).

Orthogonal wavelets

Generally, the wavelet transform can be divided into two categories, i.e., the redundant wavelet transform and the orthogonal wavelet transform. Orthogonality allows an input profile to be decomposed into a set of independent coefficients corresponding to each orthogonal basis. In other words, orthogonality implies that there is no redundancy in the information represented by the wavelet coefficients. This leads to efficient representations and many other desirable properties.

Figure 28:
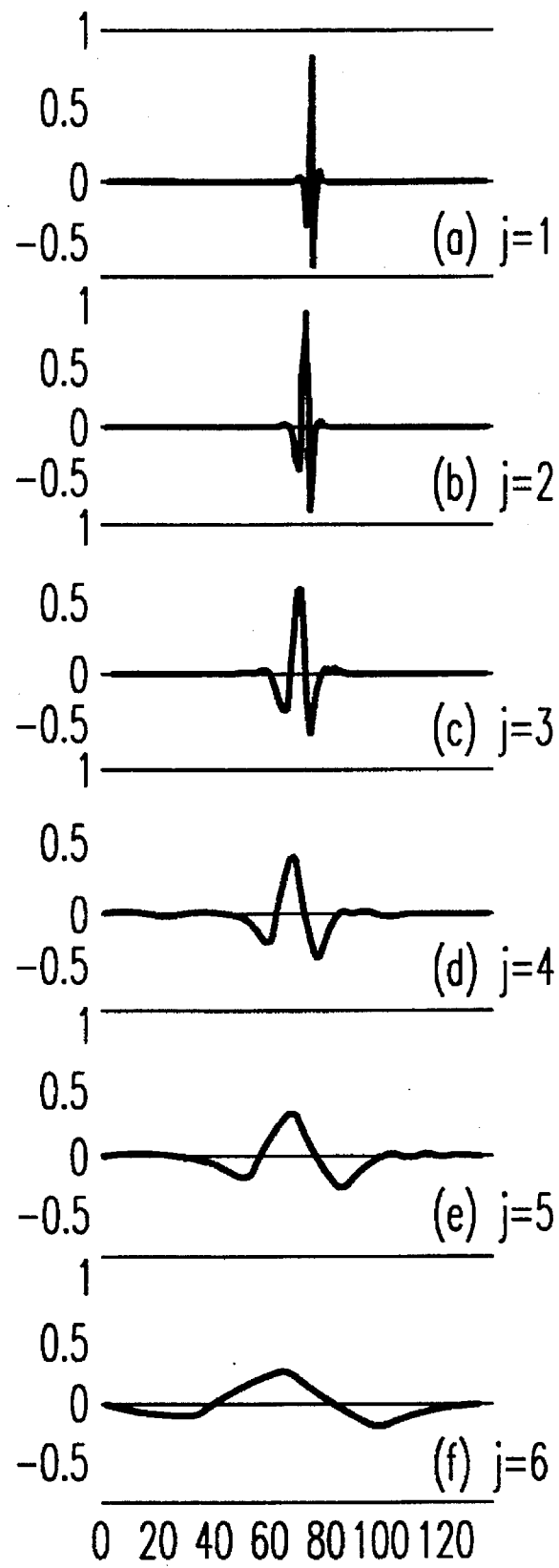
FIG. 28 is an illustration of examples of wavelets (Least Asymmetric Daubechies)

To construct the orthogonal basis, we choose the scale factor to be powers of 2. Then the scaling and translation of the mother wavelet $\psi$ are given by $$\psi_k^j(x) = \frac{1}{\sqrt{2^j}} \psi\left(\frac{x}{2^j} - k\right) \quad (1)$$

where j and k indicate integers representing a scale (or level) and translation (or location), respectively. These functions $\psi_k^j$ are called wavelets, literally meaning "little wave." Since the scaling factor $2^j$ varies as a power of 2, they are also called dyadic wavelets. FIG. 28 shows several examples. Note that the higher the level of the wavelet, the wider the distribution of the wavelet. The mother wavelet used is one family of the Daubechies' wavelets called Least Asymmetric Daubechies' wavelet with length 8 (hereinafter designated as LAD8). FIGS. 28(a)–28(f) show the wavelets at several different scales. Since the wavelets are derived by the scaling and translation of the mother wavelet, one of the wavelets in FIGS. 28(a)–(f) can be regarded as the mother wavelet. For example, if we consider FIG. 28(d) as the mother wavelet, then (a), (b), and (c) are eighth, fourth, and half scaled wavelets, while (e) and (f) are twice and four times enlarged wavelets, respectively.

The set of wavelets $\psi_k^j$ in eq. (1) forms a smooth, compactly supported (finite length), and orthogonal ($\int \psi_k^j(x) \psi_m^l(x)dx = \delta_{jl}\delta_{km}$) basis for a certain choice of the mother function $\Psi$. In this paper, we assume that $\psi_k^j$ are orthonormal wavelets. It should be noted that the scaled wavelets include an energy normalization factor $2^{-j/2}$ that keep, the energy ($\int |\psi_k^j(x)|^2 dx$) of the scaled wavelets the same as the energy in the original mother wavelet. These wavelets $\psi_k^j$ have different space-widths depending upon the frequency. For example, $\psi_o^j(x)=2^{-j/2}\psi(x/2^j)$ cover different frequency ranges as j changes. Large values of the scaling parameter j (or large scale $\psi_k^j$) correspond to low frequencies. On the other hand, small values of j (or fine scale $\psi_k^j$) correspond to high frequencies. Also, changing the parameter k allows us to move the center of wavelets, since each $\psi_k^j(x)$ is localized around $x=2^j k$. As a result, the wavelet transform can "zoom in" on very narrow, high-frequency, localized signals such as microcalcifications.

Wavelet decomposition and reconstruction

The formulation of the discrete wavelet transform is similar to that of the Fourier transform. Instead of sines and cosines, we use the wavelets $\psi_k^j(x)$ defined in eq. (1) as basis functions, namely, $$\omega_k^j = \int f(x)\psi_k^j(x)dx = \frac{1}{\sqrt{2^j}} \int f(x)\psi\left(\frac{x}{2^j} - k\right)dx \quad (2)$$

Here, $\omega_k^j$ are called wavelet coefficients. The process utilizing this equation is called the wavelet decomposition of the profile $f(x)$ by means of the set of wavelets $\psi_k^j$.

In eq. (2), each wavelet coefficient $\omega_k^j$ represents how well the profile $f(x)$ and the wavelet with scale (level) j and translation k match. If the profile $f(x)$ is similar to the wavelet at a particular scale and translation, then the coefficient has a large value. A wavelet coefficient, therefore, represents the "degree of correlation" (or similarity) between the profile and the mother wavelet at the particular scale and translation. Thus, the set of all wavelet coefficients $\omega_k^j$ gives the wavelet domain representation of the profile $f(x)$. Note that the wavelet coefficients exist only over scale and translation parameters j, k, instead of the variable x.

The inverse wavelet transform is performed in a manner similar to the inverse Fourier transform. Since the set of wavelets $\psi_k^j$ is assumed to form an orthogonal basis, the inverse wavelet transform is given by the wavelet series expansion of the original profile $f(x)$ by the same wavelets $\psi_k^j$, namely, $$f(x) = \sum_{j,k} \omega_k^j \psi_k^j(x) = \sum_{j,k} \frac{1}{\sqrt{2^j}} \omega_k^j \psi\left(\frac{x}{2^j} - k\right) \quad (3)$$

This indicates that the inverse transform expressed by eq. (3) sums over the two-dimensional scale-translation domain. This reverse process is also called wavelet reconstruction, since the original profile can be reconstructed from its wavelet coefficients. The inverse formula indicates that the profile $f(x)$ is represented as a superposition of wavelets $\psi_k^j$, and the coefficients in this superposition are given exactly by the wavelet coefficients. This feature is very useful in extracting a specific scale pattern from the original profile, as will be demonstrated below.

Figure 29H:
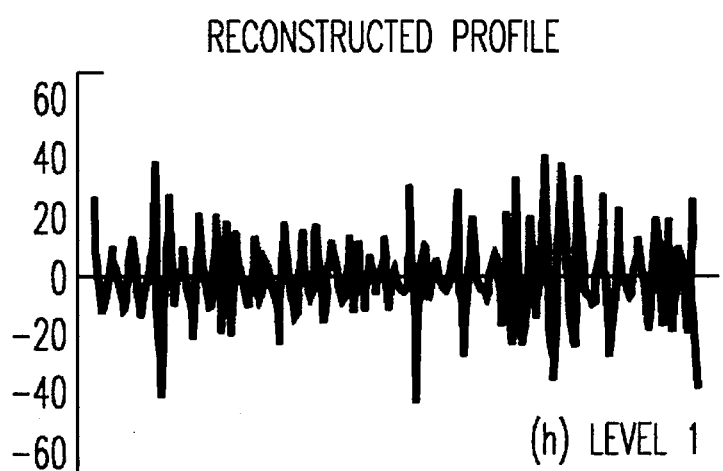
FIG. 29 is an illustration of wavelet decomposition and reconstruction of an image profile including a microcalcification (small arrow) and a simulated mass (large arrow)
Figure 29I:
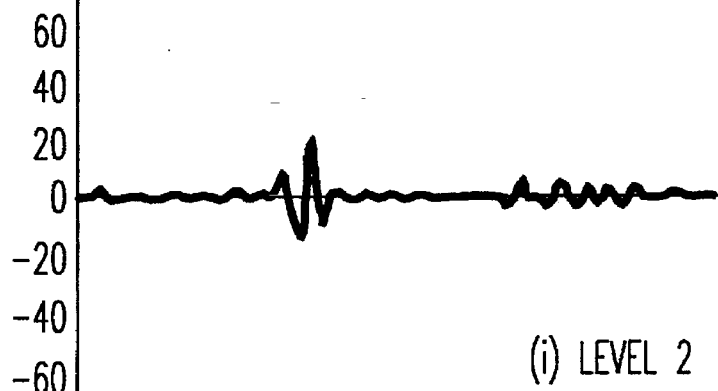
Figure 29J:
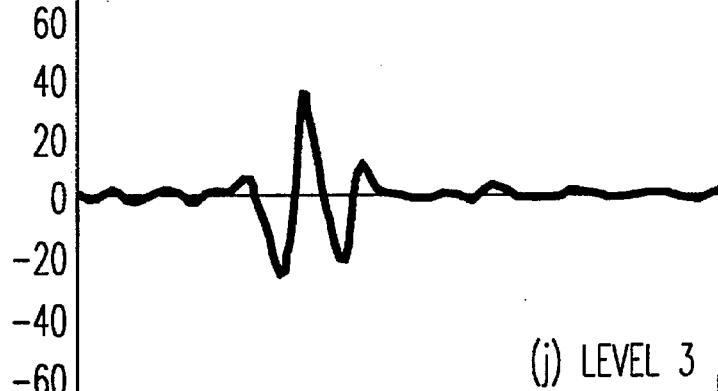

The wavelet decomposition and reconstruction of a signal are illustrated in FIG. 29 to demonstrate the characteristics of the wavelet representation and of the reconstructed signal. FIG. 29(a) shows the original profile (128 pixels in length) that includes a microcalcification indicated by a small arrow. The profile is obtained from a mammogram that was digitized to 10 bits with a pixel size of 0.1×0.1 mm using a Fuji drum scanner. The profile is modified, for demonstration purposes, by adding some noise and a simulated mass (large arrow) represented by a hump on the right side of the profile.

FIGS. 2(b)–(g) show the wavelet decomposition of the original profile up to the level 6, using the wavelets in LAD8 shown in FIG. 28. The horizontal axis of these figures roughly corresponds to the spatial position along the original profile in FIG. 29(a). The vertical axis represents the magnitude of the wavelet coefficients. It is apparent that the decomposition at level 1 extracts mainly the high-frequency noise included in the original profile. This is because the wavelet at this level is the narrowest wavelet and thus corresponds to the highest frequencies. Levels 2 and 3 extract the microcalcification effectively, since they correspond to wider wavelets or lower frequency components which appear to match the pattern of the microcalcification. Decompositions at levels 4 and 5 do not show appreciable components. However, the wavelet coefficients at level 6 indicate a large component due to the simulated mass.

FIGS. 29(h)–(m) show the reconstructed profiles from the wavelet coefficients at each level shown in FIGS. 29(b)–(g), respectively. The profile reconstructed from level 1 shows mainly noise components included in the original profile. The microcalcification becomes obvious in the profiles reconstructed from level 2 or 3. At levels 4 and 5, there are no apparent patterns. However, the reconstructed profile at level 6 indicates clearly a relatively large pattern corresponding to the simulated mass. Usually, the wavelet coefficients can be modified and then inverse-transformed through eq. (3) to extract useful information. For example, a low-pass, high-pass, or band-pass filter may be used to extract or emphasize desired patterns in the original profile. In addition, all the wavelet coefficients except for those at a particular level may be eliminated. In this way, the specific image feature that is represented by the wavelet coefficients at the specified level can be reconstructed. FIGS. 29(n) and (o) show the reconstructed profiles from the wavelet coefficients at levels 2 and 3, and levels 2, 3, 6, respectively. The microcalcification in FIG. 29(n) is demonstrated more clearly than that in FIGS. 29(i) and (j). The simulated mass in FIG. 29(o) becomes apparent by adding the wavelet coefficients at level 6. If the wavelet coefficients at six levels are utilized, the reconstructed profile in FIG. 2(p) matches the original profile. Note that the original profile can be reconstructed completely by adding the wavelet coefficients at level 7, which represent the mean value of the original profile.

Interpretation of wavelets as filters

The wavelet representation and its properties can be derived from basic features of a mother wavelet. If a function is an admissible mother wavelet, then it is equivalent to a band-pass filter, since the function has neither a zero frequency component nor infinite frequency components due to finite energy. The same features also apply to the wavelets derived by the scaling and translation of the mother wavelet. Also, the wavelet transform defined in eq. (2) can be regarded as a convolution integral, since eq. (2) can be rewritten as $$\omega_k^j = \frac{1}{\sqrt{2^j}} \int f(x)\psi\left(-\frac{1}{2^j}(2^j k - x)\right) dx \quad (4)$$

Therefore, the wavelet transform can be interpreted as a band-pass filtering of $f(x)$ by the mother function $\psi$. It should be noted that the sampling distance for the profile and mother function, shown by $2^j k$ in eq. (4), increases two-fold as the level increases one step. For example, if the sampling distance is 2 at level 1, then it becomes 4 at level 2.

Figure 30:
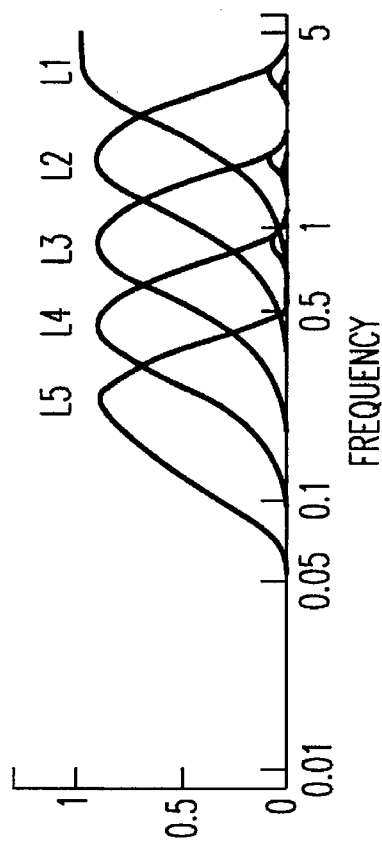
FIG. 30 is an illustration of power spectra for wavelets at levels 1–5.
Figure 31B:
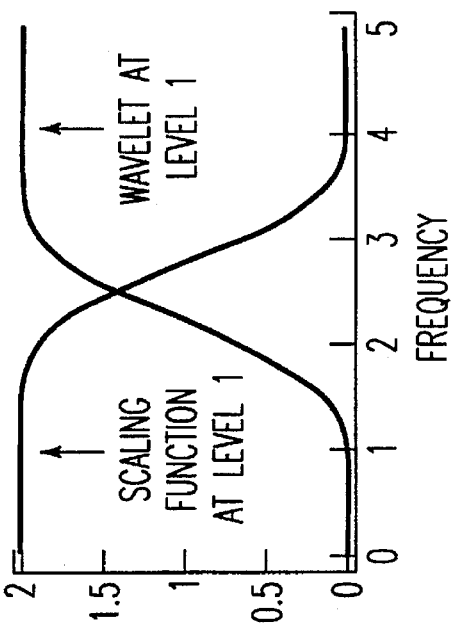
FIGS. 31(a) and 31(b) are illustrations of a scaling function at level 4 and a power spectra for the wavelet and a scaling function at level 1, respectively.
Figure 31A:
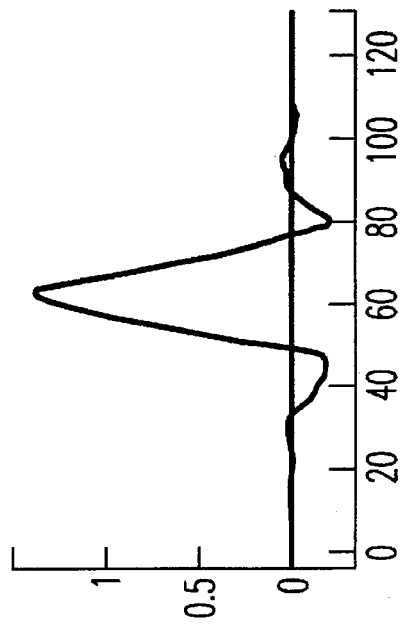

This feature of wavelets as band-pass filters is illustrated in FIG. 30, where the power spectra of the wavelets shown in FIG. 1 are demonstrated. It is apparent that a large-scale wavelet (corresponding to a large value of the scaling parameter) has the center of the frequency band located at low frequency, while a fine-scale wavelet (corresponding to a small value of the scaling parameter) has the center located at high frequency. These power spectra clearly indicate that we can extract different frequency components from the original profile by applying the wavelet transform with different scale parameters. However, it should be noted that characterizing a mother wavelet as a "band-pass" filter can be misleading, because a mother wavelet can be broad-band. The power spectrum of a mother wavelet, as shown in FIG. 29, can have many side lobes that contain a certain limited amount of energy. Therefore, the "band-pass" feature of the wavelet should be interpreted cautiously.

To understand further the features of the frequency domain decomposition by the wavelet transform, the level 1 decomposition is considered by setting j=1 in eq. (2). The components in the original profile that may be extracted by the frequency band of $\psi_k^1$ are represented as wavelet coefficients at high-frequencies, as illustrated in FIG. 29. Therefore, the remaining components include mostly low-frequency components that can be extracted by a certain low-pass filter. This low-pass filter can be considered as a "complementary filter" to the band-pass filter represented by the wavelet $\psi_k^1$.

In general, for a given mother wavelet $\psi(x)$, the complementary low-pass filter is called the scaling function or father function that is denoted by $\phi(x)$. In a manner similar to the construction of the wavelets in eq. (1), the scaling and translation of the scaling function $\phi(x)$ are defined as follows:

$$\phi_k^j(x) = \frac{1}{\sqrt{2^j}} \phi\left(\frac{x}{2^j} - k\right), \quad (5)$$

where j and k indicate integers. The function $\phi_k^j$ at level j and translation k is the low-pass filter associated with the wavelet $\psi_k^j$. It is thus called a scaling function at level j. FIG. 30(a) shows the scaling function associated with the wavelet at level 4 illustrated in FIG. 27(d). FIG. 30(b) shows the power spectra of the scaling function at level 1 and the wavelet at level 1 which roughly split the frequency domain into low- and high-frequency domains. This indicates that the set $\{\psi_k^1, \phi_k^1\}$ can form a set of basis functions, and thus a profile $f(x)$ can be represented by a linear combination of $\psi_k^1$ and $\phi_k^1$ as follows:

$$f(x) = \sum_k \omega_k^1 \psi_k^1 + \sum_k s_k^1 \phi_k^1 \qquad (6)$$

Here, the coefficients $\omega_k^1$ in the first term are obtained by setting j=1 in eq. (2). The coefficients $s_k^1$ (or, in general, $s_k^j$) in the second term can be obtained by applying the scaling function to the original profile in the same manner as the wavelet transform in eq. (2), namely, $$s_k^j = \int f(x) \phi_k^j(x) dx \qquad (7)$$

The coefficients $s_k^j$ obtained in eq. 7 are called smoothed components at level j that represent "smoothed" profiles as a result of the low-pass filtering. On the other hand, wavelet coefficients $\omega_k^j$ are called detail components at level j that represent the fine pattern or high-frequency components in the original profile.

Multiresolution analysis and two-scale relations

It is apparent in eq. (6) that the original profile $f(x)$ is separated into high-frequency components (first term) and the remaining low-frequency components (second term). It is important to note that the second term can further be split into high- and low-frequency components in a manner similar to eq. (6). This repetitive application of low-pass and high-pass filters in providing a "sharp" and "blurred" profiles is known as the multiresolution analysis in wavelet literature. A similar procedure has been studied in the field of image analysis which is called a pyramid algorithm.

To achieve this algorithm, the scaling functions at level j and level j+1 must be related. In fact, the multiresolution analysis requires the scaling function to satisfy a constraint called the two-scale relation, refinement equation, or two-scale difference that is accompanied by certain coefficients h(k) as follows:

$$\phi(x) = \sum_k h(k) \phi(2x - k), \qquad (8)$$

or, equivalently, $$\phi_l^{j+1}(x) = \sum_k h(k - 2l) \phi_k^j(x) \qquad (9)$$

Figure 32B:
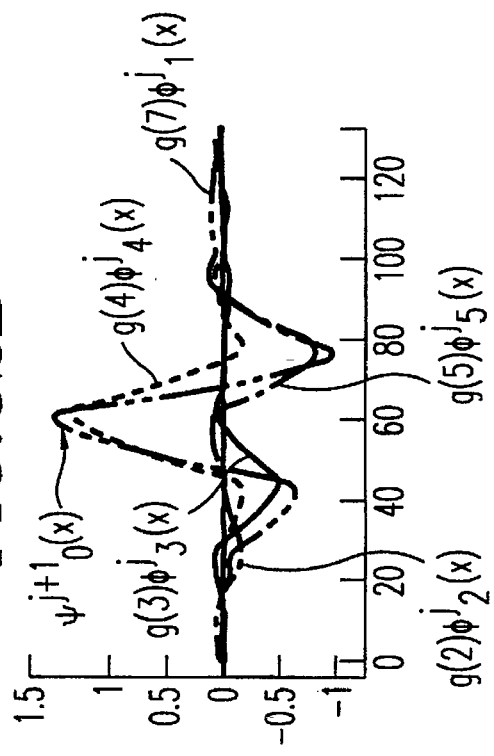
FIGS. 32(a) and 32(b) are illustrations of a construction of a scaling function at level j+1 by a linear combination of scaling functions at level j, and a construction of a wavelet at level j+1 by a linear combination of the scaling functions at level j, respectively.
Figure 32A:
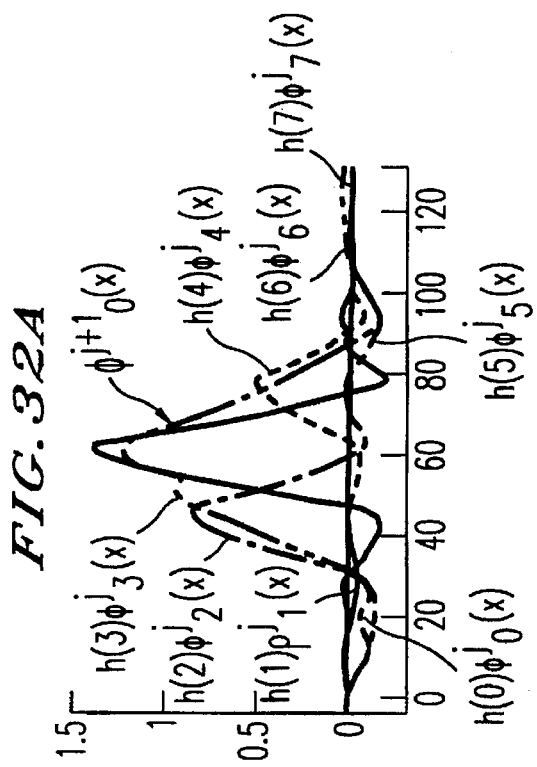

The function on the left of these equations represents the "double-sized" scaling function compared to the scaling function on the right. Therefore, the above two-scale relation indicates that the scaling functions at level j+1 can be represented by a linear combination of the translated scaling functions at the previous level j as illustrated in FIG. 32(a). The features of the coefficients h(k) will be discussed later.

By multiplying both sides of eq. (9) by $f(x)$, integrating, and by substituting eq. (7), one can show that the smoothed components $s_k^j$ and $s_k^{j+1}$ at levels j and j+1 are related as follows:

$$s_l^{j+1} = \Sigma h(k - 2l) s_k^j \qquad (10)$$

In the case of j=1, it is apparent that the smoothed components at level 2 are derived from a linear combination of those at level 1.

Similarly, the mother wavelet $\psi(x)$ is related to the scaling function by $$\psi(x) = \sum_k g(k) \phi(2x - k), \qquad (11)$$

or equivalently, $$\psi_l^{j+1}(x) = \sum_k g(k - 2l) \phi_k^j(x). \qquad (12)$$

These equations are also called two-scale relations. The double-sized wavelet on the left is represented by a weighted sum of the half-sized scaling function as illustrated in FIG. 32(b) where only the scaling functions at level j with large amplitudes are shown. The weights 61 g(k) are related to h(k) as will be shown below in eq. (14). The detail components $\omega_k^{j+1}$ at level j+1 are related to the smoothed components $s_k^j$ at level j. Their relationship can be obtained from eq. (12) in a manner similar to the derivation of eq. (10):

$$\omega_l^{j+1} = \sum_k g(k - 2l) s_k^j. \qquad (13)$$

In the case of j=1, the detail components at level 2 can be derived from a linear combination of the smoothed components at level 1. The smoothed and detail components at level 3 can also be obtained by setting j=2 in eqs. (10) and (13). The same procedure can be repeated, until the most smoothed component, that is the mean value of the profile, is obtained. The set of eqs. (10) and (13) that recursively splits the profile into high- and low-frequency channels is called the splitting algorithm or cascade algorithm in wavelet literature.

It should be noted that the coefficients h(k) and g(k) introduced in eqs. (8) and (11) perform the same role to the scaling function $\phi(x)$ and the mother wavelet $\psi(x)$. In fact, performing the discrete wavelet transform does not require the explicit forms of the scaling function or mother wavelet. Calculating the smoothed and detail components requires only h(k) and g(k), as indicated in eqs. (10) and (13). Thus, h(k) and g(k) are called the low-pass filter and the high-pass filter, respectively. The low-pass filter h(k) in eq. (8) has to meet several conditions in order for the mother wavelet in eq. (11) to be admissible and orthogonal. Usually, the high-pass filter g(k) is derived from h(k) by $$g(k) = (-1)^k h(N - 1 - k), \qquad (14)$$

where N is the number of nonzero components in the filter h(k). The filters h(k) and g(k) satisfying eq. (14) are known as quadrature mirror filters, and the splitting algorithm are known as one of the subband coding techniques in signal processing. Several different sets of filters h(k) satisfying the above conditions can be found in the wavelet literature. For example, Table VII lists the values of h(k) for the Least Asymmetric Daubechies' wavelet with length 8 (LAD8).

TABLE VII

| h(0) | h(1) | h(2) | h(3) | h(4) | h(5) | h(6) | h(7) |
| --- | --- | --- | --- | --- | --- | --- | --- |
| −0.1071 | −0.0419 | 0.7037 | 1.1367 | 0.4212 | −0.1403 | −0.0178 | 0.0456 |

Computing the wavelet decomposition and reconstruction

The computational details of the splitting algorithm using h(k) and g(k) are described below. We start with the original profile $\{s_0^0, \ldots, s_{127}^0\}$ consisting of 128 pixel locations, where the superscript denotes the level (or scale), and the subscript represents the translation (or location) at that level. The superscript 0 indicates the original data at the highest resolution level. In the following computational method, the number of sampling points N for a profile needs to be given by a power of 2. For the low-pass filter h(k), the inventors employ LAD8, as listed in Table VII, that has only eight nonzero coefficients from h(0) to h(7).

The low-pass filtering indicated in eq. (10) can be rewritten as $$s_l^{j+1} = \sum_{k=0}^{7} h(k) s_{2l+k}^j = h(0) s_{2l+1}^j + h(1) s_{2l+1}^j + \ldots + h(7) s_{2l+7}^j. \tag{15}$$

Here, the number of the smoothed components at level j+1 is one-half the number of components at level j. For example, l ranges from 0 to 63 at level 1 and from 0 to 31 at level 2. If the number of sampling points of the original profile is 128, then l ranges from 0 to $128/2^j - 1 = 2^{7-j} - 1$ at level j in eq. (15).

For calculation by computers, it may be convenient to express the decomposition process in eq. (5) by a matrix multiplication. In the matrix notation, the above equation can be expressed as $$[s_0^{j+1}, \ldots, s_{2^{6-j}-1}^{j+1}]^T = H^j [s_0^j, \ldots, s_{2^{7-j}-1}^j]^T, \tag{16}$$

where $$Hj = \tag{17}$$

$$\begin{bmatrix} h(0) & h(1) & h(2) & h(3) & \cdots & h(7) & & & \\ & & h(0) & h(1) & \cdots & h(5) & h(6) & h(7) & \\ \cdot & \cdot & & & & & & & \\ \cdot & \cdot & & & & & & & \\ \cdot & \cdot & & & & & & & \\ h(2) & h(3) & \cdots & h(7) & & & & h(0) & h(1) \end{bmatrix}$$

Here, $H^j$ is a $2^{6-j} \times 2^{7-j}$ matrix and its blank entries correspond to zeros. In a similar manner, the detail components (or wavelet coefficients) $\omega_l^j$ can be calculated by substituting eq. (14) into eq. (14) into eq. 13) as follows:

$$\omega_l^{j+1} = \tag{18}$$

$$\sum_{n=0}^{7} (-1)^n h(7-n) s_{2l+n}^j = h(7) s_{2l}^j - h(6) s_{2l+1}^j + \ldots - h(0) s_{2l+7}^j,$$

where the number of detail components at level j is $2^{7-j}$ as in the case of the smoothed components $s_k^j$. Also, the above high-pass filtering can be represented by the following matrix multiplication:

$$[\omega_0^{j+1}, \ldots, \omega_{2^{6-j}-1}^{j+1}]^T = G^j [s_0^j, \ldots, s_{2^{7-j}-1}^j]^T, \tag{19}$$

where $$G^j = \tag{20}$$

$$\begin{bmatrix} h(7) & -h(6) & h(5) & \cdots & -h(1) & h(0) & & & \\ & & h(7) & -h(6) & \cdots & & h(0) & & \\ \cdot & \cdot & & & & & & & \\ \cdot & \cdot & & & & & & & \\ \cdot & \cdot & & & & & & & \\ h(5) & -h(4) & \cdots & h(0) & & & & h(7) & -h(6) \end{bmatrix}$$

This matrix $G^j$ has the same size $2^{6-j} \times 2^{7-j}$ as the matrix $H^j$.

The splitting algorithm is performed by calculating eqs. (15) and (18) [or, equivalently, eqs. (16) and (19)] for the original profile $\{s_0^0, \ldots, s_{127}^0\}$. For example, by setting j=0 in eqs. (15) and (18), the smoothed and detail components at level is obtained. The level 1 smoothed components can be further decomposed to obtain the level 2 smoothed and detail components by setting j=1 in the same equation. This process is repeated up to the seventh level, and to obtain at the end of the algorithm, $$\{\omega_0^1, \ldots, \omega_{63}^1\} \quad \text{at level 1} \tag{21}$$

$$\{\omega_0^2, \ldots, \omega_{31}^2\} \quad \text{at level 2}$$

$$\cdot$$

$$\cdot$$

$$\cdot$$

$$\{\omega_0^6, \omega_1^6\} \quad \text{at level 6}$$

$$\{\omega_0^7, s_0^7\} \quad \text{at level 7}$$

Here, most of the coefficients are detail components except for the most smoothed component $s^7$ that is the result of many smoothing filters. It should be noted that if the original profile has $N=2^n$ sampling points, then the splitting algorithm consists of $\log_2 N$ steps (or n levels). In FIG. 33(a), this recursive wavelet decomposition process is illustrated up to the third level.

The reconstruction process can be implemented by reversing the decomposition process. Therefore, to perform the wavelet reconstruction, we begin with the lowest resolution (highest level) coefficients and work up towards the higher resolution (lower level). For example, if the wavelet decomposition coefficients in eq. (21) are given, we can initiate the reconstruction using smoothed and detail components $S_0^7$ and $\omega_0^7$ at level 7 to produce the smoothed components $s_0^6$ and $s_1^6$ at level 6 These smoothed components are then used together with wavelet coefficients $\omega_0^6$ and $\omega_0^6$ at level 6 to produce the smoothed components the next lower level (level 5). This process can be repeated until the original profile (or the smoothed components at the desired level) is obtained. This process for obtaining the smoothed components from the previous level is given by $$s_n^{j-1} = \sum_k h(n-2k) s_k^j + \sum_k g(n-2k) \omega_k^j, \tag{22}$$

where h(k) and g(k) are the low-pass and high-pass filter coefficients described in eqs. (9), (13), and (14), and listed in Table 1. In the case of orthogonal wavelets, this reconstruction process can be obtained by multiplying the transpose of matrices $H^j$ and $G^j$ in eq. (17) and (20) by the smoothed and detail components at the previous level, respectively, namely:

$$[s_0^{j-1}, \ldots, s_{2^{8-j}-1}^{j-1}]^T = (H^j)^T [s_0^j, \ldots, s_{2^{7-j}-1}^j]^T + (G^j)^T [\omega_0^j, \ldots, \omega_{2^{7-j}-1}^j]^T \tag{23}$$

Figure 33B:
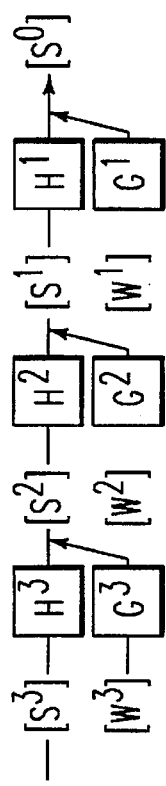
FIG. 33 is an illustration of the splitting algorithm for wavelet decomposition from level 0 to 3 and wavelet reconstruction from level 3 to 0.
Figure 33A:
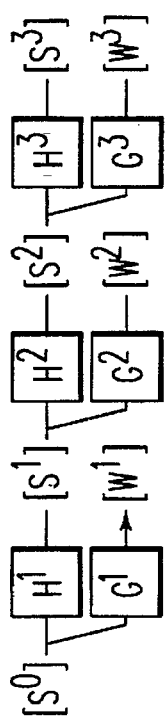

Since the wavelet reconstruction corresponds to the reversed process to the decomposition process, it can be illustrated in FIG. 33(b) by reversing the diagram in FIG. 33(a).

Wavelet transform of images
Two-dimensional wavelet transform

The one-dimensional wavelet transform above described can be easily extended to the two-dimensional wavelet transform. The two-dimensional wavelet transform is found to be very useful for image analysis. This multiresolution wavelet transform needs to be extended from operating on one-dimensional profiles to operating on two-dimensional images. The basic approach is the same as that used for the 2-dimensional Fourier transform. First, the one-dimensional wavelet transform is applied to each row of an image. Then the same transform is applied to each column. However, the one-dimensional wavelet transform is performed sequentially level by level. This procedure is described in detail in the following discussion.

The first one-dimensional sequence (or the horizontal sequence) is formed by taking the first (top) row of the image. Scanning along this top horizontal row of the image creates a one-dimensional sequence, and then repeated for the next rows of the image to create a series of one-dimensional sequences. These one-dimensional sequences are then wavelet-transformed to compute the (horizontal) wavelet coefficients. The horizontal wavelet coefficients are placed back into two-dimensional images (sub-images). These images are then scanned to create the vertical sequences. These vertical sequences are then wavelet-transformed, and the resulting sequences are rearranged to the two-dimensional image format.

In view of filtering operation, this two-dimensional wavelet transform can be regarded as applying the one-dimensional splitting algorithm to the horizontal and vertical sequences, successively. FIG. 34(a) illustrates the two-dimensional wavelet transform from level 0 (original image) to level 1, where the wavelet representation at level 1 consists of four sub-images. The first sub-image $S_S^1$ is obtained by applying the horizontal low-pass filter and the vertical low-pass filter successively. The second sub-image $W_H^1$ is obtained by applying the horizontal low-pass filter followed by the vertical high-pass filter. The third sub-image $W_V^1$ is obtained by applying the horizontal high-pass filter followed by the vertical low-pass filter. The fourth sub-image $W_D^1$ is obtained by applying the horizontal and vertical high-pass filters successively. This operation is repeated to higher levels, as in the one-dimensional case, until the most smoothed component is obtained.

To understand the unique features of these four sub-images, it would be useful to consider the wavelet representation of an image that consists of single horizontal, vertical, and diagonal lines as illustrated in FIG. 35(a). The horizontal line is a low-frequency signal for the horizontal wavelet transform, since it is a sequence of the same pixel value in the horizontal direction. However, the same horizontal line is a high-frequency signal for the vertical wavelet transform, because the line yields a delta-function like signal in the vertical direction. In a similar way, the vertical line is a high-frequency signal for the horizontal wavelet transform as well as a low-frequency signal for the vertical wavelet transform. The diagonal line appears as a series of impulses for both the horizontal and vertical wavelet transforms, and thus a high-frequency signal for both wavelet transforms. With the wavelet transform at level 1, as is shown in FIG. 35(b), the horizontal line can be extracted in the sub-image $W_H^1$ that is called the horizontal sub-image. Similarly, the vertical line is extracted in the vertical sub-image $W_V^1$. Also the diagonal line is extracted in the diagonal sub-image $W_D^1$.

It is often convenient for the computer calculation to describe the filtering process discussed above by matrix notation. First, the smoothed sub-image $S_S^{j+1}$ at level j+1 is derived by multiplying the smoothed sub-image $S_S^j$ at at the previous level j by $H^j$ transposing the resulting sub-image, and then multiplying the same matrix $H^j$ as follows:

$$S_S^{j+1} = H^j S_S^j (H^j)^T, \qquad (24)$$

where $S_S^j$ shows the matrix of the smoothed sub-image at level j, namely ($S_S^j$. As in the one-dimensional case, the sub-image $S_S^j$ has one-half of the side length (or one-quarter of the area) of the sub-image $S_S^j$ at the previous level. Similarly, the horizontal (vertical) sub-image is obtained by multiplying $H^j$ ($G^j$) and $G^j$ ($H^j$) by the sub-image at the previous level, namely, $$W_H^{j+1} = G^j S_S^j (H^j)^T, \qquad (25)$$

and $$W_V^{j+1} = H^j S_S^j (G^j)^T, \qquad (26)$$

where $W_H^j$ and $W_V^j$ represent the matrix for the horizontal and vertical sub-images, respectively. Finally, the diagonal sub-image is obtained by multiplying low-pass filter $G^j$ by the sub-image at the previous level from the left and right as follows:

$$W_D^{j+1} = G^j S_S^j (G^j)^T, \qquad (27)$$

As in the case of one-dimensional reconstruction, the two-dimensional reconstruction can be implemented by reversing the decomposition process. To perform the two-dimensional reconstruction, smoothed and detail components at a certain level are synthesized to form the smoothed components at the next lower level as indicated in FIG. 33(b). This process for the reconstruction of the smoothed components at level j is given by $$S_S^{j-1} = (H^j)^T S_S^j H^j + (G^j)^T W_H^j H^j + (H^j)^T W_V^j G^j + (G^j)^T W_D^j G^j \qquad (28)$$

For example, we can reconstruct the smoothed components $S_S^2$ at level 2 by setting j in eq. (28), where $S_S^3$, $W_H^3$, $W_V^3$, and $W_D^3$ are given by the corresponding sub-images at level 3. We can reconstruct further the smoothed components $S_S^1$ at level 1 by setting j in eq. (28), and using sub-images at level 2 for $W_H^2$, $W_V^2$, and $W_D^2$. Finally, the original image can be reconstructed by setting j in eq. (28) where $W_H^1$, $W_V^1$, and $W_D^1$ are given by the corresponding sub-images at level 1.

Wavelet decomposition and reconstruction of mammograms

To demonstrate the two-dimensional wavelet transform for image analysis, a small region of interest (ROI) of a mammogram is decomposed up to the third level. The mammogram was digitized to 10 bits with a pixel size of 0.1×0.1 mm using a Fuji drum scanner. The mother function used is LAD8. All of the sub-images at level 1 appear to show mainly the high-frequency noise included in the mammogram. It should be noted, however, that the horizontal sub-image at level 2 and horizontal/vertical sub-images at level 3 appear to provide some indications of microcalcifications. The smoothed sub-image at level 3 (or the composite from levels 4 to 10) shows the low-frequency background structure of the mammogram.

Although the decomposed sub-images may be useful for extracting microcalcifications, they may not be efficient for detection by computer or human because of their low resolution. For example, the sub-images at level 3 have only one-quarter of the original image size. Therefore, small structures such as microcalcifications may be viewed more clearly in the reconstructed images that can retain the same resolution as that of the original image. In addition, each of the decomposed sub-images has a directionality (horizontal, vertical, or diagonal). The microcalcifications, however, are not considered to have a strong directionality. Therefore, the reconstructed images from all directions may be useful to avoiding the orientation problem. The image reconstructed from level 1 shows mainly high-frequency noise components included in the mammogram. The clustered microcalcifications indicated by an arrow become obvious in the images reconstructed from level 2 or 3. Some of the microcalcifications become more obvious in the images reconstructed from levels 2 and 3.

In this study, we attempt to incorporate the wavelet transform technique was incorporated in the first step of the program, in substitution for the difference image filtering technique used to enhance the signal-to-noise ratio of microcalcifications. Instead of using the difference image filtering technique, the wavelet transform was employed to reconstruct the mammogram from lower levels (higher resolution) to enhance small signals and to suppress the low-frequency background structure.

In the wavelet processing step in new CAD scheme of the present invention, first a mammogram is decomposed using the two-dimensional wavelet transform. As above described, the two-dimensional wavelet transform can be performed by matrix multiplications shown in eqs. (24)–(27). In these equations, the matrix $H^j$ for the low-pass filtering and the matrix $G^j$ for the high-pass filtering are given by eqs. (17) and (20), respectively. To perform the decomposition, we start with the original mammogram $S_s^0$ which typically has a matrix size of 1024×1024 pixels. For this size of image, the size of the matrices $H^j$ and $G^j$ in eqs. (24)–(27) is given by $2^{9-j} \times 2^{10-j}$. At the highest resolution (j=0), therefore, the matrix size of $H^0$ and $G^0$ becomes 512×1024. Starting from the original mammogram $S_s^0$, we can obtain the four sub-images $S_s^1$, $W_H^1$, $W_V^1$, and $W_D^1$ which consists of level 1 decomposition of the original mammogram $S_s^0$ by setting j=0 in eqs (24)–(27) as follows:

$$S_s^1 = H^0 S_s^0 (H^0)^T, \quad W_H^1 = G^0 S_s^0 (H^0)^T, \quad (29)$$

$$W_V^1 = H^0 S_s^0 (G^0)^T, \quad W_D^1 = H^0 S_s^0 (G^0)^T. \quad (30)$$

Each one of these sub-images has the one-half of the side length of the original mammogram. The level 2 decomposition is performed by further decomposing the smoothed components $S_s^1$ at level 1 obtained in eq. (29). To perform this decomposition, $S_s^1$ is multiplied by the low-pass filtering matrix $H^1$ and the high-pass filtering matrix $G^1$ at level 12 as shown below.

$$S_s^2 = H^1 S_s^1 (H^1)^T, \quad W_H^2 = G^1 S_s^1 (H^1)^T \quad (31)$$

$$W_V^2 = H^1 S_s^1 (G^1)^T, \quad W_D^2 = G^1 S_s^1 (G^1) \quad (32)$$

Each of these matrices has the size 256×512, which is one-half of the size of $H^0$ and $G_0$; therefore, the sub-images $S_s^2$, $W_H^2$, $W_V^2$, $W_D^2$ at level 2 have the size of one-quarter in area of the original mammogram. By repeating the same process, the wavelet decomposition of a mammogram is obtained to an arbitrary level up to the highest level $10 = \log_2(1024)$ in case of a mammogram with matrix size of 1024×1024.

The two dimensional reconstruction can be implemented by reversing the above decomposition process as shown in eq. (28). However, to obtain the reconstructed image from particular levels, some unnecessary sub-images should be removed from the reconstruction process. For example, to obtain the reconstructed image $S_s^{0'}$ from level 1 only, all sub-images at level 1, except for the smoothed sub-image $S_s^1$, are combined using eq. (28) by setting j=1. Namely, $S_s^{0'}$ is obtained only from the detail sub-images $W_H^1$, $W_V^1$, and $W_D^1$ at level 1 as follows.

$$S_s^{0'} = (G^0)^T W_H^1 H^0 + (H^0)^T W_V^1 G^0 + (G^0)^T W_D^1 G^0 \quad (33)$$

In a similar manner, the reconstructed image $S_s^0$ from levels 2 and 3 can be obtained as follows. First, the smoothed image $S_s^{2'}$ at level 2 is obtained from detail sub-images $W_H^3$, $W_V^3$, and $W_D^3$ at level 3 as follows.

$$S_s^{2'} = (G^2)^T W_H^3 H^2 + (H^2)^T W_V^3 G^2 + (G^2)^T W_D^3 G^2. \quad (34)$$

Then this smoothed image $S_s^{2'}$ is combined with detail sub-images $W_H^2$, $W_V^2$, and $W_D^2$ at level 2 to obtain the smoothed sub-image $S_s^{1'}$ at level 1 as shown below.

$$S_s^{1'} = (H^1)^T S_s^{2'} H^1 + (G^1)^T W_H^2 H^1 + (H^1)^T W_V^2 G^1 + (G^1)^T W_D^2 G^1 \quad (35)$$

Finally, the reconstructed image $S_s^0$ from levels 2 and 3 is obtained from the thus smoothed sub image $S^{S1'}$ only as follows as shown in the following equation.

$$S_s^{0''} = (H^0)^T S_s^{1'} H^0 \quad (36)$$

The inventors have observed that reconstructed mammograms with microcalcifications using wavelet components obtained at the different levels and reconstructed from levels 2 and 3 showed clear patterns of microcalcifications relative to reconstructed images obtained from other levels in the wavelet domain. Therefore, the combination of levels 2 and 3 are preferably employed for computerized detection of microcalcifications based on the wavelet transform technique according to the present invention.

The major steps involved in the modified CAD scheme after the wavelet transform are as shown in FIG. 1 are briefly summarized as follows. A global grey-level thresholding is applied to the reconstructed images in order to extract possible microcalcifications. Area filtering by means of morphological erosion is then used to eliminate very small signals caused by image noise. Local grey-level thresholding is employed to reduce further the number of false signals. The thresholding is based on the local statistics (mean and standard deviation) of the pixel values (grey levels) in a 5.1×5.1 mm area in the image. The threshold level is set equal to a multiple of the standard deviation plus the mean pixel value. Typically, multiples ranging from 2.0 to 3.8 are used. Next, a texture analysis is performed on the mammogram to reduce the number of falsely detected signals in the reconstructed images. Finally, the remaining signals are grouped or clustered to examine whether clustered microcalcifications that include three or more microcalcifications in a given size area can be identified.

To evaluate the performance of the wavelet transform, the above-described database consisting of 39 screen-film mammograms was used. Various types of wavelets were examined to increase the signal-to-noise ratio of clustered microcalcifications, and the Least Asymmetric Daubechies' wavelets were chosen to be one of the most promising wavelets in enhancing the signals of microcalcifications while suppressing the background structure of the mammograms. Also, images reconstructed from several different levels were examined and their performances were compared based on FROC curves.

FIG. 36(a) shows the comparison of FROC curves obtained with three different wavelets having different lengths. Here, LADS, LAD12, and LAD20 show the Least Asymmetric Daubechies' wavelets with length 8, 12, and 20, respectively. All of the evaluations were made using the reconstructed images from levels 1–3. It appears in FIG. 36(a) that the maximum sensitivity obtainable at a relatively large number of false positives increases as the length of the wavelet decreases. This result seems to indicate that, at levels 1–3, the shorter wavelets in this family may have larger degree of correlation with microcalcifications included in our mammograms. Our scheme with the wavelet transform approach can identify approximately 85% of the "true" clusters with about 5 false detections per mammogram. FIG. 36(b) shows the performance of our scheme for images reconstructed from several different levels obtained with the wavelets in LADS. The reconstructed images obtained from levels 2–3 and 1–3 are comparable, and indicate the highest performance among various combinations of different levels. The image reconstructed from levels 1–2 shows a lower performance, because the microcalcifications are less obvious in this image due to the absence of level 3. The image reconstructed from levels 1–4 also produces a lower performance, because it contains many background structures that tend to yield a large number of false positives.

FIG. 37 shows the comparison of FROC curves obtained by performing a logical OR operation between two different schemes. Two curves marked by STD and LAD 20 are obtained by our rule-based, difference image technique shown in FIG. 1 and the new method based on the wavelet transform technique, respectively. Two curves marked by LT3.4 and LT3.6 are obtained by combining the two different techniques through a logical OR operation. In this OR operation, all clusters obtained from two different schemes are combined together to provide a set of detected clusters. If the distance between two clusters detected by the two schemes is less than 60 pixels, then they are identical as the same cluster. If either one of these two clusters is a true positive, then the identified cluster is marked as a true positive cluster. Otherwise, the identified cluster is marked as a false positive cluster. For a cluster that has no corresponding cluster in the other scheme, its true or false classification is not changed.

The curve labeled by LT3.4 is obtained by performing a logical OR between the clusters detected by LAD20 with a local thresholding value of 3.6 and the clusters detected by the standard rule-based difference image method indicated as STD at several different levels. The curve labeled by LT3.6 is obtained by the same procedure with the local thresholding value 3.6 for LAD20. As this figure shows, the curve with LT3.4 demonstrates the best performance with a sensitivity of 90% in detecting clustered microcalcifications in mammograms. This result indicates that the performance of a computerized scheme in detecting clustered microcalcifications can be improved by combining the rule-based, difference image technique and the wavelet based scheme.

Figure 38:
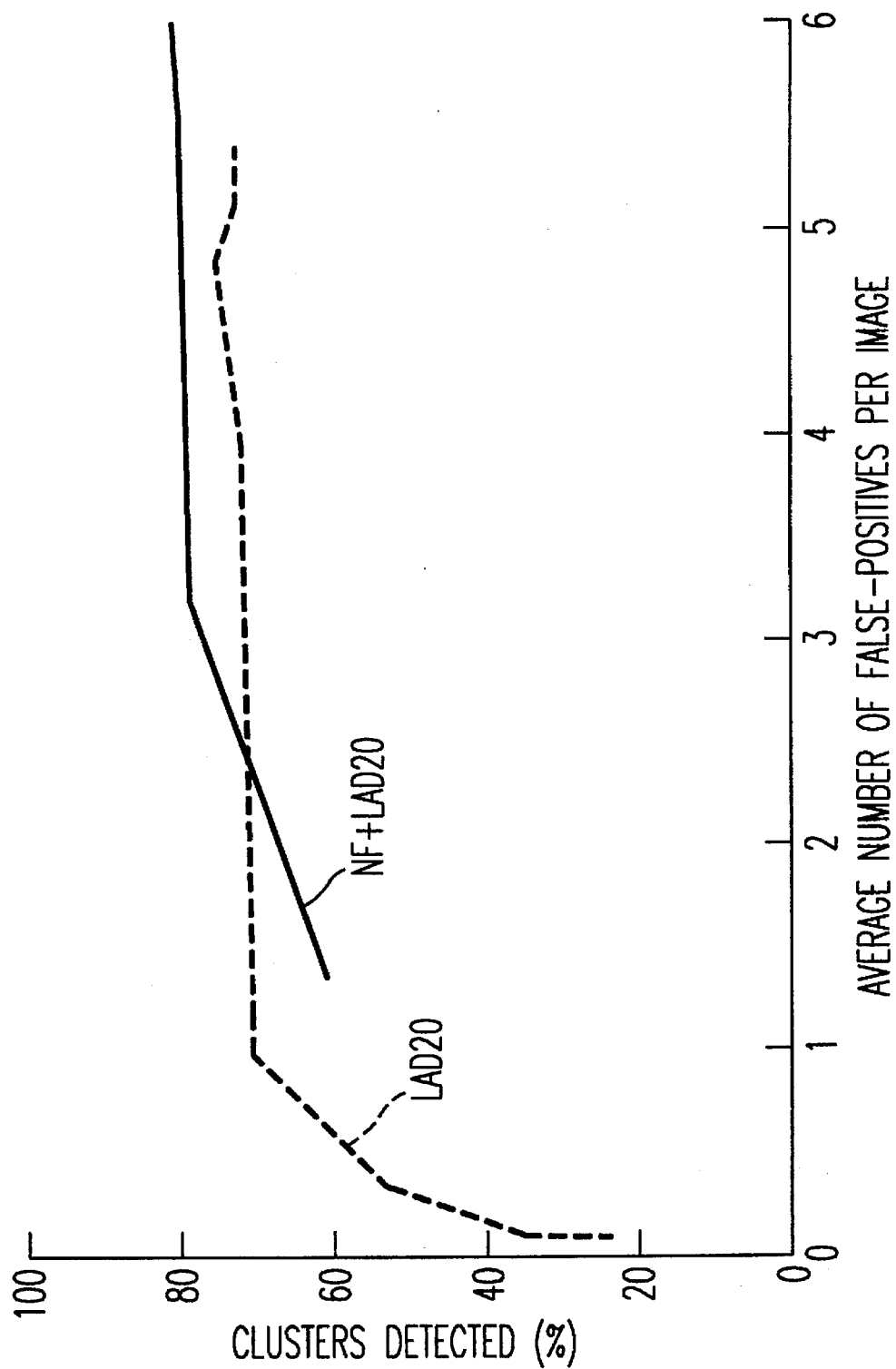
FIG. 38 is a FROC chart illustrating the effect of a non-linear noise reduction filter on the performance of a CAD scheme with the wavelet transformed in detecting clustered microcalcifications.

FIG. 38 shows the comparison of FROC curves obtained by applying a nonlinear filter to the original mammogram to reduce the noise in the mammogram. The curve labeled NF+LAD20 is obtained by using a nonlinear filter as a preprocessing step prior to the application of the wavelet transform. As this figure shows, NF+LAD20 demonstrates a better performance in terms of detection of clustered microcalcifications than LAD20 at the high false-positive region.

The wavelet transformation can be used in substitution for the difference image technique shown in FIG. 11(a).

Figure 39:
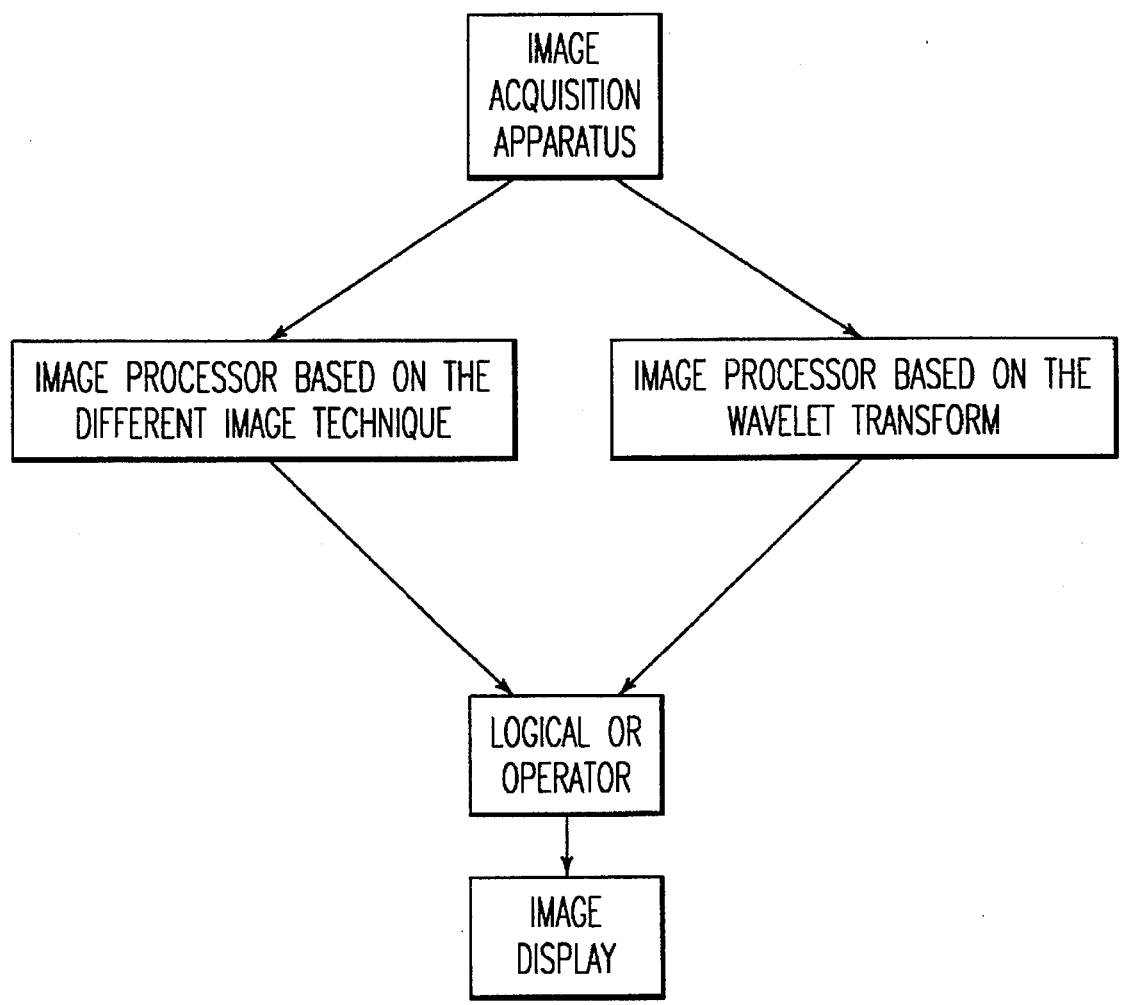
FIG. 39 is a schematic flow chart illustrating an embodiment to the invention in which the results of processing using the difference technique and processing using the wavelet transform are logically OR'ed to produce a result into image for display.

Similarly, in the multiple difference imaging technique of FIG. 11(c), the wavelet transformation can be substituted for the difference image processor in one arm of the technique, as schematically shown in FIG. 39.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for automated detection of an abnormal anatomic region, comprising:

obtaining a digital image of an object including said anatomic region;

subjecting said digital image to noise reduction filtering, comprising, subjecting said digital image to separate morphological erosion and dilation operators using plural structuring elements to produce an eroded image and a dilated image, determining a first absolute difference between said digital image and said eroded image and a second absolute difference between said digital image and said dilated image on a pixel by pixel basis, substituting for values of pixels in the digital image with values of corresponding pixels in the eroded image when the first absolute difference is greater than the second absolute difference on a pixel by pixel basis, and substituting for values of pixels in the digital image with values of corresponding pixels in the dilated image when the second absolute difference is greater than the first absolute difference on a pixel by pixel basis, said substituting steps producing a noise filtered image;

performing linear filtering on said noise filtered image; and performing predetermined signal extraction and feature analysis routines on the linear filtered image to identify first locations of candidate abnormal regions.

2. The method according to claim 1, further comprising:

performing linear filtering and predetermined signal extraction and feature analysis routines on said digital image to identify second locations of candidate abnormal regions;

logically AND'ing the first and second locations of candidate abnormal regions to identify the product of said AND'ing as locations of remaining candidate abnormal regions.

3. The method of claim 2, comprising:

determining an edge gradient for each of the AND'ed remaining candidate abnormal regions;

comparing each edge gradient determined in said determining step with at least one threshold; and eliminating candidate abnormal regions in said remaining candidate abnormal regions from consideration as abnormal regions based on a result of said comparing step.

4. The method of claim 3, wherein:

said comparing step comprises comparing each edge gradient with a predetermined number; and said eliminating step comprises eliminating those candidate abnormal regions having an edge gradient exceeding said predetermined number.

5. The method of claim 4, wherein:

said comparing step comprises comparing each edge gradient with a varying threshold which varies inversely as a function of the average pixel value of the pixels of the respective candidate abnormal region; and said eliminating step comprises eliminating those candidate abnormal regions having an edge gradient less than said varying threshold.

6. The method of claim 5, wherein the AND'ed candidate abnormal regions are locations of microcalcifications and locations of microcalcification clusters, comprising:

determining edge gradients for the locations of said microcalcifications and for the locations of said microcalcification clusters; and comparing the edge gradients determined for said microcalcification locations and for said microcalcification cluster locations with respective thresholds; and eliminating locations based on the comparing of microcalcification location edge gradients with respective thresholds and based on the comparing of microcalcification cluster edge gradients with respective thresholds.

7. The method according to claim 6, comprising:

determining a degree of linearity for each of said locations of said remaining candidate abnormal regions;

comparing the degree of linearity determined for each location with a predetermined linearity threshold; and eliminating from consideration as abnormal regions candidate abnormal regions having a linearity factor exceeding said predetermined linearity threshold.

8. The method according to claim 2, comprising:

determining a degree of linearity for each of said locations of said remaining candidate abnormal regions;

comparing the degree of linearity determined for each location with a predetermined linearity threshold; and eliminating from consideration as abnormal regions candidate abnormal regions having a linearity factor exceeding said predetermined linearity threshold.

9. The method of claim 3, wherein:

said comparing step comprises comparing each edge gradient with a varying threshold which varies inversely as a function of the average pixel value of the pixels of the respective candidate abnormal region; and said eliminating step comprises eliminating those candidate abnormal regions having an edge gradient less than said varying threshold.

10. The method according to claim 9, comprising:

determining a degree of linearity for each of said locations of said remaining candidate abnormal regions;

comparing the degree of linearity determined for each location with a predetermined linearity threshold; and eliminating from consideration as abnormal regions candidate abnormal regions having a linearity factor exceeding said predetermined linearity threshold.

11. The method according to claim 3, comprising:

determining a degree of linearity for each of said locations of said remaining candidate abnormal regions;

comparing the degree of linearity determined for each location with a predetermined linearity threshold; and eliminating from consideration as abnormal regions candidate abnormal regions having a linearity factor exceeding said predetermined linearity threshold.

12. The method according to claim 4, comprising:

determining a degree of linearity for each of said locations of said remaining candidate abnormal regions;

comparing the degree of linearity determined for each location with a predetermined linearity threshold; and eliminating from consideration as abnormal regions candidate abnormal regions having a linearity factor exceeding said predetermined linearity threshold.

13. The method according to claim 5, comprising:

determining a degree of linearity for each of said locations of said remaining candidate abnormal regions;

comparing the degree of linearity determined for each location with a predetermined linearity threshold; and eliminating from consideration as abnormal regions candidate abnormal regions having a linearity factor exceeding said predetermined linearity threshold.

14. The method according to claim 1, comprising:

determining a degree of linearity for each of said first locations;

comparing the degree of linearity determined for each first location with a predetermined linearity threshold; and eliminating from consideration as abnormal regions candidate abnormal regions having a linearity factor exceeding said predetermined linearity threshold.

15. A filtering method for reducing noise in a digital image, comprising:

subjecting said digital image to separate morphological erosion and dilation operators using plural structuring elements to produce an eroded image and a dilated image, determining a first absolute difference between said digital image and said eroded image and a second absolute difference between said digital image and said dilated image on a pixel by pixel basis;

substituting for values of pixels in the digital image with values of corresponding pixels in the eroded image when the first absolute difference is greater than the second absolute difference on a pixel by pixel basis; and substituting for values of pixels in the digital image with values of corresponding pixels in the dilated image when the second absolute difference is greater than the first absolute difference on a pixel by pixel basis, said substituting steps producing a noise filtered image.

* * * * *